(12) United States Patent
Lassner et al.

(10) Patent No.: US 6,541,259 B1
(45) Date of Patent: Apr. 1, 2003

(54) NUCLEIC ACID SEQUENCES TO PROTEINS INVOLVED IN ISOPRENOID SYNTHESIS

(75) Inventors: Michael W. Lassner, Foster City, CA (US); Beth Savidge, Davis, CA (US); Timothy Mitsky, Maryland Heights, MO (US); James Weiss, Kirkwood, MO (US); Martha Ann Post-Beittenmiller, Manchester, MO (US)

(73) Assignee: Calgene LLC, Davis, CA (US)

( * ) Notice: Subject to any disclaimer, the term of this patent is extended or adjusted under 35 U.S.C. 154(b) by 0 days.

(21) Appl. No.: 09/549,848

(22) Filed: Apr. 14, 2000

Related U.S. Application Data

(60) Provisional application No. 60/129,899, filed on Apr. 15, 1999, and provisional application No. 60/146,461, filed on Jul. 30, 1999.

(51) Int. Cl.$^7$ .......................... C07H 21/04; C12N 5/14; C12N 15/74; C12N 15/82

(52) U.S. Cl. .................... 435/468; 435/320.1; 435/419; 435/471; 536/23.6

(58) Field of Search .............................. 435/320.1, 419, 435/468, 471; 536/23.6; 800/278, 298

(56) References Cited

U.S. PATENT DOCUMENTS

| | | |
|---|---|---|
| 5,545,816 A | 8/1996 | Ausich et al. |
| 5,693,507 A | 12/1997 | Daniell et al. |
| 5,876,964 A | 3/1999 | Gershenzon et al. |

FOREIGN PATENT DOCUMENTS

| | | | |
|---|---|---|---|
| EP | 531639 A2 | * | 3/1993 |
| EP | 1033405 | | 9/2000 |
| GB | 560529 | * | 4/1944 |
| WO | WO 97/27285 | | 7/1997 |
| WO | WO 98/06862 | | 2/1998 |
| WO | WO 99/04622 | | 2/1999 |
| WO | 00/63391 | * | 10/2000 |
| WO | WO 00/68393 | | 11/2000 |

OTHER PUBLICATIONS

Shewmaker et al, "Seed–specific overexpression of phytoene synthase: increase in carotenoids and other metabolic effects", 1999, The Plant Journal vol. 20, No. 4, pp. 401–412.*

Burkhardt et al., Transgenic rice (*Oryza sativa*) endosperm expressing daffodil (*Narcissus pseudonarcissus*) . . . A biosynthesis, 1997, The Plant Journal vol. 11, No. 5, pp. 1071–1078.*

Li et al., "Identification of a maize endosperm–specific cDNA encoding farnesyl pyrophosphate synthetase", *Gene* 171:193–196 (1996).

Murata et al., EMBL Sequence Database Accession No. D13960, Mar. 28, 1996.

International Search Report, PCT/US01/12334 (Apr. 2002).*

Bevan et al., Trembl Database Accession No. O65524, Aug. 01, 1998.*

Kaneko et al., Embl Sequence Database Accession No. D90909, Oct. 31, 1996.*

Kaneko et al., Trembl Database Accession No. P73727; Feb. 01, 1997.*

Chen et al., Embl Sequence Database Accession No. AI995392, Mar. 09, 1999.*

Stocker et al., "Identification of the Tocopherol–Cyclase in the Blue–Green Algae *Anabaena variabilis*" 76:1729–1738 (1993).*

Arango et al., "Tocopherol synthesis from homogentisate in *Capsicum anuum* L. (yellow pepper) chromoplast membranes: evidence for tocopherol cyclase", *Biochem J.* 336:531–533 (1998).*

Stocker et al., "The Substrate Specificity of Tocopherol Cyclase", *Bioorganic & Medicinal Chemistry* 4(7):1129–1134 (1996).*

Spurgeon et al., *Biosynthesis of Isoprenoid Compounds*, (1981), vol. 1, pp. 1–46.

Fiedler et al., 1982, *Planta*, 155:511–515.

Soll et al., 1980, *Arch. Biochem. Biophys.* 204: 544–550.

Marshall et al., 1985, *Phytochem*, 24: 1705–1711.

Svab et al., (1990) *Proc. Natl. Acad. Sci. USA* 87:8526–8530.

Svab et al., (1993) *Proc. Natl. Acad. Sci. USA* 90:913–917.

Database Embl Accession No. AC003673, *Arabidopsis thaliana* chromosome II section 110 of 255 of the complete sequence. Sequence from clones MSF3, F19F24, (Dec. 11, 1997).

Database Embl Accession No: AL035394, *Arabidopsis thaliana* DNA chromosome 4, BAC clone F9D16 (ESSAII project), (Feb. 9, 1999).

Database Embl Accession No. B24116, *F18L14TF IGF Arabidopsis thaliana genomic clone F18L14, genomic survey sequence*, (Oct. 13, 1997).

Database Embl Accession No: AC003672, *Arabidopsis thaliana* chromosome II section 239 of 255 of the complete sequence. Sequences from clones F4II, FI6B22, (Dec. 11, 1997).

Database Embl Accession No: B29398, *F16B22TRC IGF Arabidopsis thaliana genomic clone F16B22, genomic survey sequence*, (Oct. 13, 1997).

(List continued on next page.)

*Primary Examiner*—Elizabeth F. McElwain
*Assistant Examiner*—Cynthia Collins
(74) *Attorney, Agent, or Firm*—Brian K. Stierwalt; Arnold & Porter

(57) ABSTRACT

Nucleic acid sequences and methods are provided for producing plants and seeds having altered tocopherol content and compositions. The methods find particular use in increasing the tocopherol levels in plants, and in providing desirable tocopherol compositions in a host plant cell.

15 Claims, 26 Drawing Sheets

OTHER PUBLICATIONS

Database Embl Accession No: R30625, 13230 Lambda–PRL2 Arabidopsis thaliana cDNA clone 166L10T7, mRNA sequence, (Aug. 11, 1995).

Gaubier Pascale et al., *A chlorophyll sythetase gene from Arabidopsis thaliana*, Molecular and General Genetics, vol. 249, No. 1, pp. 58–64.

Database Biosis, Oster U et al., *The G4 gene Arabidopsis thaliana encodes a chlorophyll sythase of etiolated plants*, Botanica Acta, vol. 110, No. 5, pp. 420–423 (10/97).

Zhu Xufen et al., *Geranylgeranyl pyrophosphate synthase encoded by the newly isolated gene GGPS6 from Arabidopsis thaliana is localized in mitochondria*, Plant Molecular. Biology, vol. 35, No. 3, pp. 331–341, (1997).

Database Embl Accession No: L40577, Scolink, P. A. et al., *Arabidopsis thaliana geranylgeranyl pyrophosphate synthase–related protein mRNA, complete cds*, (Apr. 15, 1995).

Lopez, J. et al., *Sequence of the bchG gene from Chloroflexus aurantiacus: Relationship between chlorophyll synthase and other polyprenyl transferases*, Journal of Bacteriology, (1996), vol. 178, No. 11, pp. 3369–3373.

Kuntz, M. et al., *Identification of a cDNA for the plastid-–located geranylgeranyl pyrophosphate synthase from Capsicum annuum: correlative increase in enzyme activity and transcript level during fruit ripening*, The Plant Journal, (1992), vol. 2, No. 1.

Norris, R. et al., *Genetic dissection of carotenoid synthesis on arabidopsis defines plastoquinone as essential component of phytoene society of plant physiologists*, Plant Cell, (Dec. 1, 1995), vol. 7.

* cited by examiner

```
           *         280         *         300         *         320         *         340         *
ATPT2    : WKR-FALVAAMCILAVRAIIVQIAFYLH-IQTHVFGRPII-FTRPEL-FATAFMSFFSVVIALFKDIPDIEGDKI-FETRSFSVTLG-QKR  : 313
SLR1736  : LKR-FSLLAALCILTVRGIVVNLGLFLF-FRIGLGYPPTI-ITPIW--LTLFILVFTVALAIFKDVPDMEGDRQ-FKIQLTQIG-KQN  : 218
ATPT3    : SYP-LMKRFTFWPQAFLGLTINWGAILG--WT--AVKGSIAPSIVPLYLSGVCWTIVDTIYAHQDKEDDVK-VEVKSTAIRFG-DNT  : 328
SLR0926  : AYP-GAKRVFPVPQLVLSIAWGFAVEIS--WS--AVTGDITDATWMLWGATVFWTIGFDTVYAMADREDDRR-ICVNSSAIFFG-QYV  : 213
ATPT4    : VXT-PLKQLHPINTWVGAVVGAIPPFLG--WA--AASGQISYNSMWISLPAALYFWQLIPHFWALAHLCRNDYAA-GEYKMLSIFDP--S  : 294
SLL1899  : VYTHWLKRHTAQNIVIGGAAGSIPPEVG--WA--AVTGDISWTPWVILFALIFLWTPPHFWALALMIKDDYAQ-VNVPMLPVIAGEEKT  : 220
ATPT12   : IYS-APPLKLKQNGWVGNFALGASYESLPWWAGQALFGTETPDVVIITLLYSIAGIGIAIVNDFKSVEGDRA-LGLQSLPVAFG-TET  : 308
SLR0056  : IYS-APPLKLKQNGWIGNYALGASYEALPWWAGHALFGTENPTIMVILTLIYSLAGIGIAVVNDFKSVEGDRQ-LCLKSLPUMFE-IGT  : 242
ATPT8    : EITSSTEQRYSMDYYLQKTYYKTASIISNSCKAVAVLTGQTAEVALAFEYGRNLGIAFQLIDDILDFTGTSASLCKGLSDIRH--GV  : 231
SLR1518  : TYQGPPFRLGYLGLGELICLITFGPIAI-AAAYYSQSQSFSWNLET-PSVFVGISTAIILFCSHFHQVEDDLA-ACKKSPIVRLG-TKL  : 223
                                                                                              g

*         360         *         380         *         400         *         420         *         440
ATPT2    : VFWTCYTLTQMAYAVAILVGATSPFIWSKVISVVGHVILATTIWARAKSVDLSSKTEITS---CYMFIWKLFYAEYLLLPFLK---  : 393
SLR1736  : VFRGTLILITGCYLAMAIWGLWAAMPLNTAFLIVSHLCLLALIWWRSRDVHLESKTEIAS---FYQFIWKLFFLEYLLYPIAIWLPNFS  : 304
ATPT3    : KLWITGFGTASIGFIALSGFSADLGWQYYASLAAASGQLGWQESTADLSSGADCS---GTADLSSGADCS-----VLGRSFQ---  : 407
SLR0926  : GEAVGIFFALTIGCLFYLGMILMLNPLYWLSLAIAI--VGMWIQYIQLSAPTPEP-KLY---GQIFGQNVIIGFVLLAGLLGWL--  : 292
ATPT4    : GKRIAAVAIRNCFYMIPEGFIAYDWGLTSSWFCLESTLLTLAIAATAFSFYRDRTMHKA---RKMFHASLLFLPVFMSGLLHRVSND  : 379
SLL1899  : VSQIWYYSLLVVPFSLLVYPLHQLGLILYLATAIIL--GGQFIVKAWQLKQAPGRDLA----RGLFKFSIFYLMLICLAVIDSLPVT  : 303
ATPT12   : AKWICYGAIDITQLSVAGYLIASGKPYYALALWALI--IPQIFQFKYFLKDPVKYDVK----YQASAQPFLVLGIFVTAIASQH---  : 387
SLR0056  : AAWICVIMIDVFQAGIAGYLIYHQQLYATIVILL--IPQITFQDMYFLRNPLENDVK----YQASAQPFLVFGMEATGIALGHAGI-  : 324
ATPT8    : ITAPILFAMEEFPQLREVDQVEKDPRNVDIAIEYLGKSKGIQRARELAMEHANLAAAAIGSLPETDNEDVKRSRRALIDETHRVITRN  : 320
SLR1518  : GSQVLTLSVVSLYLITAIGVLCHQAPWQTLLILASLPWAVQLERHVGQYHDQPEQVSNCK---FIAVNLHFFSGMLMAAGYGWAGLG--  : 307
                                                                    g

*         460         *         480         *
ATPT2    : -----------------------------------------------  :   -
SLR1736  : NTIF-------------------------------------------  :   -
ATPT3    : -----------------------------------------------  :   -
SLR0926  : -----------------------------------------------  :   -
ATPT4    : NQQQLVEEAGLTNSVSGEVKTQRRKKRVAQPPVAYASAAPFPFLPAPSFYSP  : 431
SLL1899  : --HQLVAQMGTLLLG--------------------------------  : 316
ATPT12   : -----------------------------------------------  : 308
SLR0056  : -----------------------------------------------  :   -
ATPT8    : K----------------------------------------------  : 321
SLR1518  : -----------------------------------------------  :   -
```

Figure 22 2/2

NUCLEIC ACID SEQUENCES TO PROTEINS INVOLVED IN ISOPRENOID SYNTHESIS

This application claims the benefit of the filing date of the provisional Application U.S. Ser. No. 60/129,899, filed Apr. 15, 1999, and the provisional Application, U.S. Ser. No. 60/146,461, filed Jul. 30, 1999.

TECHNICAL FIELD

The present invention is directed to nucleic acid and amino acid sequences and constructs, and methods related thereto.

BACKGROUND

Isoprenoids are ubiquitous compounds found in all living organisms. Plants synthesize a diverse array of greater than 22,000 isoprenoids (Connolly and Hill (1992) *Dictionary of Terpenoids*, Chapman and Hall, New York, N.Y.). In plants, isoprenoids play essential roles in particular cell functions such as production of sterols, contributing to eukaryotic membrane architecture, acyclic polyprenoids found in the side chain of ubiquinone and plastoquinone, growth regulators like abscisic acid, gibberellins, brassinosteroids or the photosynthetic pigments chlorophylls and carotenoids. Although the physiological role of other plant isoprenoids is less evident, like that of the vast array of secondary metabolites, some are known to play key roles mediating the adaptative responses to different environmental challenges. In spite of the remarkable diversity of structure and function, all isoprenoids originate from a single metabolic precursor, isopentenyl diphosphate (IPP) (Wright, (1961) *Annu. Rev. Biochem.* 20: 525–548; and Spurgeon and Porter, (1981) in *Biosynthesis of Isoprenoid Compounds.*, Porter and Spurgeon eds (John Wiley, New York) Vol. 1, pp1–46).

A number of unique and interconnected biochemical pathways derived from the isoprenoid pathway leading to secondary metabolites, including tocopherols, exist in chloroplasts of higher plants. Tocopherols not only perform vital functions in plants, but are also important from mammalian nutritional perspectives. In plastids, tocopherols account for up to 40% of the total quinone pool.

Tocopherols and tocotrienols (unsaturated tocopherol derivatives) are well known antioxidants, and play an important role in protecting cells from free radical damage, and in the prevention of many diseases, including cardiac disease, cancer, cataracts, retinopathy, Alzheimer's disease, andneurodegeneration, and have been shown to have beneficial effects on symptoms of arthritis, and in anti-aging. .Vitamin E is used in chicken feed for improving the shelf life, appearance, flavor, and oxidative stability of meat, and to transfer tocols from feed to eggs. Vitamin E has been shown to be essential for normal reproduction, improves overall performance, and enhances immunocompetence in livestock animals. Vitamin E supplement in animal feed also imparts oxidative stability to milk products.

The demand for natural tocopherols as supplements has been steadily growing at a rate of 10–20% for the past three years. At present, the demand exceeds the supply for natural tocopherols, which are known to be more biopotent than racemic mixtures of synthetically produced tocopherols. Naturally occurring tocopherols are all d-stereomers, whereas synthetic α-tocopherol is a mixture of eight d,l-α-tocopherol isomers, only one of which (12.5%) is identical to the natural d-α-tocopherol. Natural d-α-tocopherol has the highest vitamin E activity (1.49 IU/mg) when compared to other natural tocopherols or tocotrienols. The synthetic α-tocopherol has a vitamin E activity of 1.1 IU/mg. In 1995, the worldwide market for raw refined tocopherols was $1020 million; synthetic materials comprised 85–88% of the market, the remaining 12–15% being natural materials. The best sources of natural tocopherols and tocotrienols are vegetable oils and grain products. Currently, most of the natural Vitamin E is produced from γ-tocopherol derived from soy oil processing, which is subsequently converted to α-tocopherol by chemical modification (α-tocopherol exhibits the greatest biological activity).

Methods of enhancing the levels of tocopherols and tocotrienols in plants, especially levels of the more desirable compounds that can be used directly, without chemical modification, would be useful to the art as such molecules exhibit better functionality and biovailability.

In addition, methods for the increased production of other isoprenoid derived compounds in a host plant cell is desirable. Furthermore, methods for the production of particular isoprenoid compounds in a host plant cell is also needed.

SUMMARY OF THE INVENTION

The present invention is directed to prenyltransferase (PT), and in particular to PT polynucleotides and polypeptides. The polynucleotides and polypeptides of the present invention include those derived from prokaryotic and eukaryotic sources.

Thus, one aspect of the present invention relates to isolated polynucleotide sequences encoding prenyltransferase proteins. In particular, isolated nucleic acid sequences encoding PT proteins from bacterial and plant sources are provided.

Another aspect of the present invention relates to oligonucleotides which include partial or complete PT encoding sequences.

It is also an aspect of the present invention to provide recombinant DNA constructs which can be used for transcription or transcription and translation (expression) of prenyltransferase. In particular, constructs are provided which are capable of transcription or transcription and translation in host cells.

In another aspect of the present invention, methods are provided for production of prenyltransferase in a host cell or progeny thereof. In particular, host cells are transformed or transfected with a DNA construct which can be used for transcription or transcription and translation of prenyltransferase. The recombinant cells which contain prenyltransferase are also part of the present invention.

In a further aspect, the present invention relates to methods of using polynucleotide and polypeptide sequences to modify the tocopherol content of host cells, particularly in host plant cells. Plant cells having such a modified tocopherol content are also contemplated herein.

The modified plants, seeds and oils obtained by the expression of the prenyltransferases are also considered part of the invention.

BRIEF DESCRIPTION OF THE DRAWINGS

FIG. 1 provides an amino acid sequence alignment between ATPT2, ATPT3, ATPT4, ATPT8, and ATPT12 (SEQ ID NOs: 2, 4, 6, 12 and 17, respectively), performed using ClustalW.

FIG. 21 provides an amino acid sequence alignment using ClustalW between the Synechocystis sequence knockouts slr1736, slr0926, sll1899, slr0056, and slr1518 (SEQ ID NOs: 37, 32, 33, 34 and 35, respectively).

FIG. 22 provides an amino acid sequence of the ATPT2, ATPT3, ATPT4, ATPT8 and ATPT12 protein sequences from Arabidopsis (SEQ ID NOs: 2, 4, 6, 12 and 17, respectively) and the slr736, slr0926, sll1899, slr0056, and the slr1518 amino acid sequences from Synechocystis (SEQ ID NOs: 37, 32, 33, 34 and 35, respectively).

DETAILED DESCRIPTION OF THE INVENTION

Figure 2:
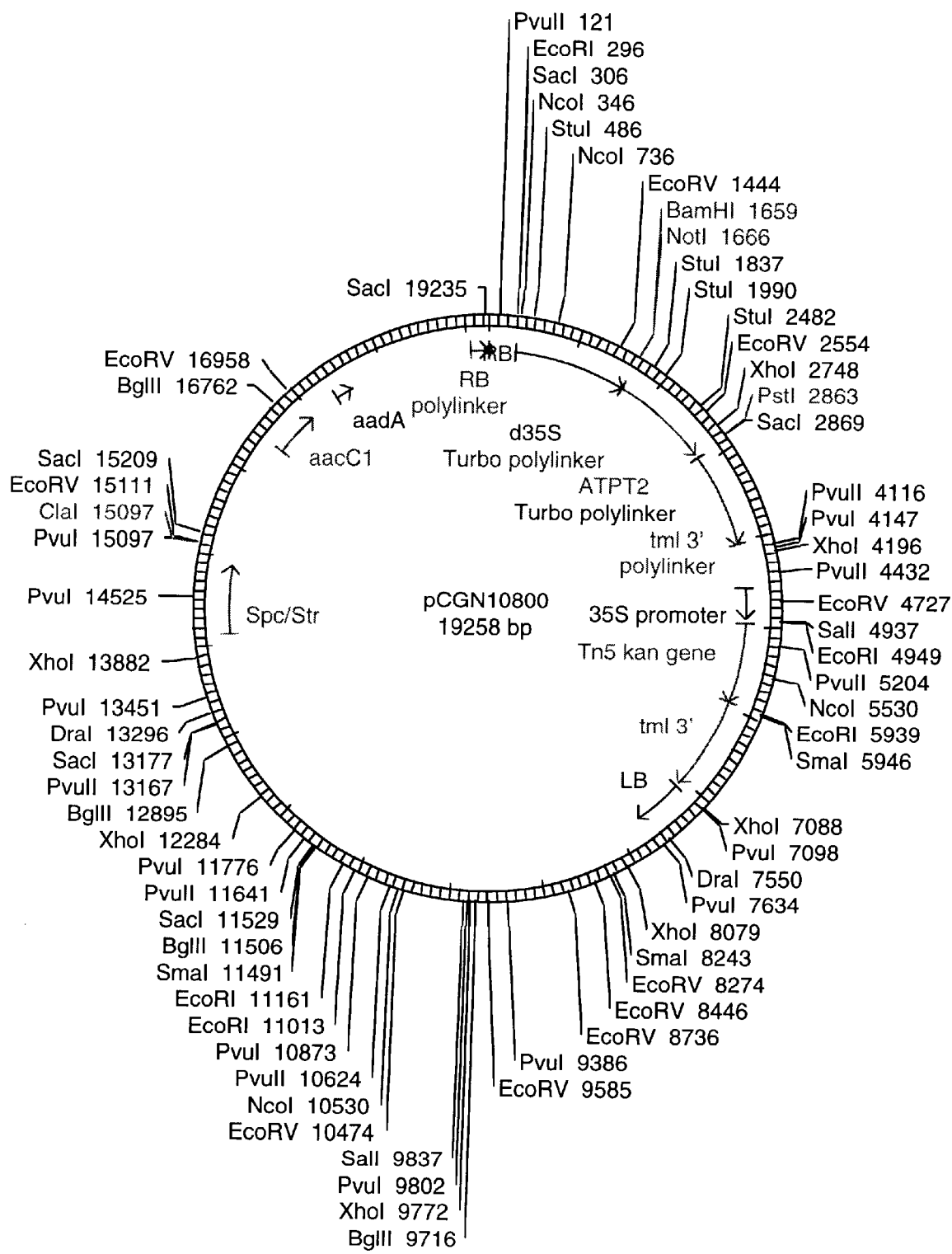
FIG. 2 provides a schematic picture of the expression construct pCGN10800.

The present invention provides, inter alia, compositions and methods for altering (for example, increasing and decreasing) the tocopherol levels and/or modulating their ratios in host cells. In particular, the present invention provides polynucleotides, polypeptides, and methods of use thereof for the modulation of tocopherol content in host plant cells.

The present invention provides polynucleotide and polypeptide sequences involved in the prenylation of straight chain and aromatic compounds. Straight chain prenyl transferases as used herein comprises sequences which encode proteins involved in the prenylation of straight chain compounds, including, but not limited to, geranyl geranyl pyrophosphate and farnesyl pyrophosphate. Aromatic prenyl transferases, as used herein, comprises sequences which encode proteins involved in the prenylation of aromatic compounds, including, but not limited to, menaquinone, ubiquinone, chlorophyll, and homogentisic acid. The prenyl transferase of the present invention preferably prenylates homogentisic acid.

The biosynthesis of α-tocopherol in higher plants involves condensation of homogentisic acid and phytylpyrophosphate to form 2-methyl-6phytylbenzoquinol that can, by cyclization and subsequent methylations (Fiedler et al., 1982, Planta, 155: 511–515, Soll et al., 1980, Arch. Biochem. Biophys. 204: 544–550, Marshall et al., 1985 Phytochem., 24: 1705–1711, all of which are herein incorporated by reference in their entirety), form various tocopherols. The Arabidopsis pds2 mutant identified and characterized by Norris et al. (1995), is deficient in tocopherol and plastiquinone-9 accumulation. Further genetic and biochemical analysis suggests that the protein encoded by PDS2 may be responsible for the prenylation of homogentisic acid. This may be a rate limiting step in tocopherol biosynthesis, and this gene has yet to be isolated. Thus, it is an aspect of the present invention to provide polynucleotides and polypeptides involved in the prenylation of homogentisic acid.

Isolated Polynucleotides, Proteins, and Polypeptides

A first aspect of the present invention relates to isolated prenyltransferase polynucleotides. The polynucleotide sequences of the present invention include isolated polynucleotides that encode the polypeptides of the invention having a deduced amino acid sequence selected from the group of sequences set forth in the Sequence Listing and to other polynucleotide sequences closely related to such sequences and variants thereof.

The invention provides a polynucleotide sequence identical over its entire length to each coding sequence as set forth in the Sequence Listing. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro- protein sequence. The polynucleotide can also include non-coding sequences, including for example, but not limited to, non-coding 5' and 3' sequences, such as the transcribed, untranslated sequences, termination signals, ribosome binding sites, sequences. that stabilize MRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

The invention also includes polynucleotides of the formula:

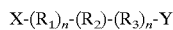

wherein, at the 5' end, X is hydrogen, and at the 3' end, Y is hydrogen or a metal, $R_1$ and $R_3$ are any nucleic acid residue, n is an integer between 1 and 3000, preferably between 1 and 1000 and $R_2$ is a nucleic acid sequence of the invention, particularly a nucleic acid sequence selected from the group set forth in the Sequence Listing and preferably those of SEQ ID NOs: 1, 3, 5, 7, 8, 10, 11, 13–16, 18, 23, 29, 36, and 38. In the formula, $R_2$ is oriented so that its 5' end residue is at the left, bound to $R_1$, and its 3' end residue is at the right, bound to $R_3$. Any stretch of nucleic acid residues denoted by either R group, where R is greater than 1, may be either aheteropolymer or a homopolymer, preferably aheteropolymer.

The invention also relates to variants of the polynucleotides described herein that encode for variants of the polypeptides of the invention. Variants that are fragments of the polynucleotides of the invention can be used to synthesize full-length polynucleotides of the invention. Preferred embodiments are polynucleotides encoding polypeptide variants wherein 5 to 10, 1 to 5, 1 to 3, 2, 1 or no amino acid residues of a polypeptide sequence of the invention are substituted, added or deleted, in any combination. Particularly preferred are substitutions, additions, and deletions that are silent such that they do not alter the properties or activities of the polynucleotide or polypeptide.

Further preferred embodiments of the invention that are at least 50%, 60%, or 70% identical over their entire length to a polynucleotide encoding a polypeptide of the invention, and polynucleotides that are complementary to such polynucleotides. More preferable are polynucleotides that comprise a region that is at least 80% identical over its entire length to a polynucleotide encoding a polypeptide of the invention and polynucleotides that are complementary thereto. In this regard, polynucleotides at least 90% identical over their entire length are particularly preferred, those at least 95% identical are especially preferred. Further, those with at least 97% identity are highly preferred and those with at least 98% and 99% identity are particularly highly preferred, with those at least 99% being the most highly preferred.

Preferred embodiments are polynucleotides that encode polypeptides that retain substantially the same biological function or activity as the mature polypeptides encoded by the polynucleotides set forth in the Sequence Listing.

The invention further relates to polynucleotides that hybridize to the above-described sequences. In particular, the invention relates to polynucleotides that hybridize under stringent conditions to the above-described polynucleotides. As used herein, the terms "stringent conditions" and "stringent hybridization conditions" mean that hybridization will generally occur if there is at least 95% and preferably at least 97% identity between the sequences. An example of stringent hybridization conditions is overnight incubation at 42° C. in a solution comprising 50% formamide, 5 x SSC (150 mM NaCl, 15 mM trisodium citrate), 50 mM sodium phosphate (pH 7.6), 5 x Denhardt's solution, 10% dextran sulfate, and 20 micrograms/milliliter denatured, sheared salmon sperm DNA, followed by washing the hybridization support in 0.1 x SSC at approximately 65° C. Other hybridization. and wash conditions are well known and are exemplified in Sambrook, et al., Molecular Cloning: A Laboratory Manual, Second Edition, cold Spring Harbor, NY (1989), particularly Chapter 11.

The invention also provides a polynucleotide consisting essentially of a polynucleotide sequence obtainable by screening an appropriate library containing the complete gene for a polynucleotide sequence set for in the Sequence Listing under stringent hybridization conditions with a probe having the sequence of said polynucleotide sequence or a fragment thereof; and isolating said polynucleotide sequence. Fragments useful for obtaining such a polynucleotide include, for example, probes and primers as described herein.

As discussed herein regarding polynucleotide assays of the invention, for example, polynucleotides of the invention can be used as a hybridization probe for RNA, cDNA, or genomic DNA to isolate full length cDNAs or genomic clones encoding a polypeptide and to isolate cDNA or genomic clones of other genes that have a high sequence similarity to a polynucleotide set forth in the Sequence Listing. Such probes will generally comprise at least 15 bases. Preferably such probes will have at least 30 bases and can have at least 50 bases. Particularly preferred probes will have between 30 bases and 50 bases, inclusive.

The coding region of each gene that comprises or is comprised by a polynucleotide sequence set forth in the Sequence Listing may be isolated by screening using a DNA sequence provided in the Sequence Listing to synthesize an oligonucleotide probe. A labeled oligonucleotide having a sequence complementary to that of a gene of the invention is then used to screen a library of cDNA, genomic DNA or mRNA to identify members of the library which hybridize to the probe. For example, synthetic oligonucleotides are prepared which correspond to the prenyltransferase EST sequences. The oligonucleotides are used as primers in polymerase chain reaction (PCR) techniques to obtain 5' and 3' terminal sequence of prenyl transferase genes. Alternatively, where oligonucleotides of low degeneracy can be prepared from particular prenyltransferase peptides, such probes may be used directly to screen gene libraries for prenyltransferase gene sequences. In particular, screening of cDNA libraries inphage vectors is useful in such methods due to lower levels of background hybridization.

Typically, a prenyltransferase sequence obtainable from the use of nucleic acid probes will show 60–70% sequence identity between the target prenyltransferase sequence and the encoding sequence used as a probe. However, lengthy sequences with as little as 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80% sequence homology) from the sequences used as probe. Oligonucleotide probes can be considerably shorter than the entire nucleic acid sequence encoding an prenyltransferase enzyme, but should be at least about 10, preferably at least about 15, and more preferably at least about 20 nucleotides. A higher degree of sequence identity is desired when shorter regions are used as opposed to longer regions. It may thus be desirable to identify regions of highly conserved amino acid sequence to design oligonucleotide probes for detecting and recovering other related prenyltransferase genes. Shorter probes are often particularly useful for polymerase chain reactions (PCR), especially when highly conserved sequences can be identified. (See, Gould, et al., *PNAS USA* (1989) 86: 1934–1938.).

Another aspect of the present invention relates to prenyltransferase polypeptides. Such polypeptides include isolated polypeptides set forth in the Sequence Listing, as well as polypeptides and fragments thereof, particularly those polypeptides which exhibit prenyltransferase activity and also those polypeptides which have at least 50%, 60% or 70% identity, preferably at least 80% identity, more preferably at least 90% identity, and most preferably at least 95% identity to a polypeptide sequence selected from the group of sequences set forth in the Sequence Listing, and also include portions of such polypeptides, wherein such portion of the polypeptide preferably includes at least 30 amino acids and more preferably includes at least 50 amino acids.

"Identity", as is well understood in the art, is a relationship between two or more polypeptide sequences or two or more polynucleotide sequences, as determined by comparing the sequences. In the art, "identity" also means the degree of sequence relatedness between polypeptide or polynucleotide sequences,, as determined by the.match between strings of such sequences. "Identity" can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., SIAM *J Applied Math*, 48: 1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1): 387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12: 76–80 (1994); Birren, et al., *Genome Analysis*, 1: 543–559 (1997)). The BLAST X program is publicly available from NCBI and other sources (*BLAST Manual*, Altschul, S., et al., NCBI NLM NIH, Bethesda, Md. 20894; Altschul, S., et al., *J. Mol. Biol.*, 215: 403–410 (1990)). The well known Smith Waterman algorithm can also be used to determine identity.

Parameters for polypeptide sequence comparison typically include the following:

Algorithm: Needleman and Wunsch, *J. Mol. Biol.* 48: 443–453 (1970)

Comparison matrix: BLOSSUM62 from Hentikoff and Hentikoff, *Proc. Natl. Acad. Sci USA* 89: 10915–10919 (1992)

Gap Penalty: 12

Gap Length Penalty: 4

A program which can be used with these parameters is publicly available as the "gap" program from Genetics Computer Group, Madison Wis. The above parameters along with no penalty for end gap are the default parameters for peptide comparisons.

Parameters for polynucleotide sequence comparison include the following:

Algorithm: Needleman and Wunsch, J. Mol. Biol. 48: 443–453 (1970)

Comparison matrix: matches=+10; mismatches=0

Gap Penalty: 50

Gap Length Penalty: 3

A program which can be used with these parameters is publicly available as the "gap" program from Genetics Computer Group, Madison Wis. The above parameters are the default parameters for nucleic acid comparisons.

The invention also includes polypeptides of the formula:

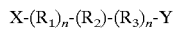

$$X\text{-}(R_1)_n\text{-}(R_2)\text{-}(R_3)_n\text{-}Y$$

wherein, at the amino terminus, X is hydrogen, and at the carboxyl terminus, Y is hydrogen or a metal, $R_1$ and $R_3$ are any amino acid residue, n is an integer between 1 and 1000, and $R_2$ is an amino acid sequence of the invention, particularly an amino acid sequence selected from the group set forth in the Sequence Listing and preferably those encoded by the sequences provided in SEQ ID NOs: 2, 4, 6, 9, 12, 17, 19–22, 24–28, 30, 32–35, 37, and 39. In the formula, $R_2$ is oriented so that its amino terminal residue: is at the left, bound to $R_1$, and its carboxy terminal residue is at the right, bound to $R_3$. Any stretch of amino acid residues denoted by either R group, where R is greater than 1, may be either a heteropolymer or a homopolymer, preferably a heteropolymer.

Polypeptides of the present invention include isolated polypeptides encoded by a polynucleotide comprising a sequence selected from the group of a sequence contained in the Sequence Listing set forth herein .

The polypeptides of the present invention can be mature protein or can be part of a fusion protein.

Fragments and variants of the polypeptides are also considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those fragments that antigenic or immunogenic in an animal, particularly a human.

Variants of the polypeptide also include polypeptides that vary from the sequences set forth in the Sequence Listing by conservative amino acid substitutions, substitution of a residue by another with like characteristics. In general, such substitutions are among Ala, Val, Leu and Ile; between Ser and Thr; between Asp and Glu; between Asn and Gln; between Lys and Arg; or between Phe and Tyr. Particularly preferred are variants in which 5 to 10; 1 to 5; 1 to 3 or one amino acid(s) are substituted, deleted, or added, in any combination.

Variants that are fragments of the polypeptides of the invention can be used to produce the corresponding full length polypeptide by peptide synthesis. Therefore, these variants can be used as intermediates for producing the full-length polypeptides of the invention.

The polynucleotides and polypeptides of the invention can be used, for example, in the transformation of host cells, such as plant host cells, as further discussed herein.

The invention also provides polynucleotides that encode a polypeptide that is a mature protein plus additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes can be used to remove any additional amino acids from the mature protein.

A precursor protein, having the mature form of the polypeptide fused to one or more prosequences may be an inactive form of the polypeptide. The inactive precursors generally are activated when the prosequences are removed. Some or all of the prosequences may be removed prior to activation. Such precursor protein are generally called pro-proteins.

Plant Constructs and Methods of Use

Of particular interest is the use of the nucleotide sequences in recombinant DNA constructs to direct the transcription or transcription and translation (expression) of the prenyltransferase sequences of the present invention in a host plant cell. The expression constructs generally comprise a promoter functional in a host plant cell operably linked to a nucleic acid sequence encoding a prenyltransferase of the present invention and a transcriptional termination region functional in a host plant cell.

A first nucleic acid sequence is "operably linked" or "operably associated" with a second nucleic acid sequence when the sequences are so arranged that the first nucleic acid sequence affects the function of the second nucleic-acid sequence. Preferably, the two sequences are part of a single contiguous nucleic acid molecule and more preferably are adjacent. For example, a promoter is operably linked to a gene if the promoter regulates or mediates transcription of the gene in a cell.

Those skilled in the art will recognize that there are a number of promoters which are functional in plant cells, and have been described in the literature. Chloroplast and plastid specific promoters, chloroplast or plastid functional promoters, and chloroplast or plastid operable promoters are also envisioned.

One set of plant functional promoters are constitutive promoters such as the CaMV35S or FMV35S promoters that yield high levels of expression in most plant organs. Enhanced or duplicated versions of the CaMV35S and FMV35S promoters are useful in the practice of this invention (Odell, et al. (1985) *Nature* 313: 810–812; Rogers, U.S. Pat. No. 5,378,619). In addition, it may also be preferred to bring about expression of the prenyltransferase gene in specific tissues of the plant, such as leaf, stem, root, tuber, seed, fruit, etc., and the promoter chosen should have the desired tissue and developmental specificity.

Of particular interest is the expression of the nucleic acid sequences of the present invention from transcription initiation regions which are preferentially expressed in a plant seed tissue. Examples of such seed preferential transcription initiation sequences include those sequences derived from sequences encoding plant storage protein genes or from genes involved in fatty acid biosynthesis in oilseeds. Examples of such promoters include the 5' regulatory regions from such genes as napin (Kridl et al., *Seed Sci. Res.* 1:209:219 (1991)), phaseolin, zein, soybean trypsin inhibitor, ACP, stearoyl-ACP desaturase, soybean $\alpha'$ subunit of $\beta$-conglycinin (soy 7s, (Chen et al., *Proc. Natl. Acad. Sci.*, 83: 8560–8564 (1986))) and oleosin.

It may be advantageous to direct the localization of proteins conferring prenyltransferase to a particular subcellular compartment, for example, to the mitochondrion, endoplasmic reticulum, vacuoles, chloroplast or other plastidic compartment. For example, where the genes of interest of the present invention will be targeted to plastids, such as chloroplasts, for expression, the constructs will also employ the use of sequences to direct the gene to the plastid. Such sequences are referred to herein as chloroplast transit peptides (CTP) or plastid transit peptides (PTP). In this manner, where the gene of interest is not directly inserted into the plastid, the expression construct will additionally contain a gene encoding a transit peptide to direct the gene of interest to the plastid. The chloroplast transit peptides may be derived from the gene of interest, or may be derived from a heterologous sequence having a CTP. Such transit peptides are known in the art. See, for example, Von Heijne et al. (1991) *Plant Mol. Biol. Rep.* 9: 104–126; Clark et al. (1989) *J. Biol. Chem.* 264: 17544–17550; della-Cioppa et al. (1987) *Plant Physiol.* 84: 965–968; Romer et al. (1993) *Biochem. Biophys. Res Commun.* 196: 1414–1421; and, Shah et al. (1986) *Science* 233: 478–481.

Depending upon the intended use, the constructs may contain the nucleic acid sequence which encodes the entire prenyltransferase protein, or a portion thereof. For example, where antisense inhibition of a given prenyltransferase protein is desired, the entire prenyltransferase sequence is not required. Furthermore, where prenyltransferase sequences used in constructs are intended for use as probes, it may be advantageous to prepare constructs containing only a particular portion of a prenyltransferase encoding sequence, for example a sequence which is discovered to encode a highly conserved prenyltransferase region.

The skilled artisan will recognize that there are various methods for the inhibition of expression of endogenous sequences in a host cell. Such methods include, but are not limited to, antisense suppression (Smith, et al. (1988) *Nature* 334: 724–726) , co-suppression (Napoli, et al. (1989) *Plant Cell* 2: 279–289), ribozymes (PCT Publication WO 97/10328), and combinations of sense and antisense Waterhouse, et al. (1998) *Proc. Natl. Acad. Sci. USA* 95: 13959–13964. Methods for the suppression of endogenous sequences in a host cell typically employ the transcription or transcription and translation of at least a portion of the sequence to be suppressed. Such sequences may be homologous to coding as well as non-coding regions of the endogenous sequence.

Regulatory transcript termination regions may be provided in plant expression constructs of this invention as well. Transcript termination regions may be provided by the DNA sequence encoding the prenyltransferase or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention.

Alternatively, constructs may be prepared to direct the expression of the prenyltransferase sequences directly from the host plant cell plastid. Such constructs and methods are known in the art and are generally described, for example, in Svab, et al. (1990) *Proc. Natl. Acad. Sci. USA* 87: 8526–8530 and Svab and Maliga (1993) *Proc. Natl. Acad. Sci. USA* 90: 913–917 and in U.S. Pat. No. 5,693,507.

The prenyltransferase constructs of the present invention can be used in transformation methods with additional constructs providing for the expression of other nucleic acid sequences encoding proteins involved in the production of tocopherols, or tocopherol precursors such as homogentisic acid and/or phytylpyrophosphate. Nucleic acid sequences encoding proteins involved in the production of homogentisic acid are known in the art, and include but not are limited to, 4-hydroxyphenylpyruvate dioxygenase (HPPD, EC 1.13.11.27) described for example, by Garcia, et al. ((1999) *Plant Physiol.* 119(4): 1507–1516), mono or bifunctional tyrA (described for example by Xia, et al. (1992) *J. Gen Microbiol.* 138: 1309–1316, and Hudson, et al. (1984) *J. Mol. Biol.* 180: 1023–1051), Oxygenase, 4-hydroxyphenylpyruvatedi- (9CI), 4-Hydroxyphenylpyruvate dioxygenase; p-Hydroxyphenylpyruvate dioxygenase; p-Hydroxyphenylpyruvate hydroxylase; p-Hydroxyphenylpyruvate oxidase; p-Hydroxyphenylpyruvic acid hydroxylase; p-Hydroxyphenylpyruvic hydroxylase; p-Hydroxyphenylpyruvic oxidase), 4-hydroxyphenylacetate, NAD(P)H: oxygen oxidoreductase (1-hydroxylating); 4-hydroxyphenylacetate 1-monooxygenase, and the like. In addition, constructs for the expression of nucleic acid sequences encoding proteins involved in the production of phytylpyrophosphate can also be employed with the prenyltransferase constructs of the present invention. Nucleic acid sequences encoding proteins involved in the production of phytylpyrophosphate are known in the art, and include, but are not limited to geranylgeranylpyrophosphate synthase (GGPPS), geranylgeranylpyrophosphatereductase (GGH), 1-deoxyxylulose-5-phosphate synthase, 1-deoxy-D-xylolose-5-phosphate reductoisomerase, 4-diphosphocytidyl-2-C-methylerythritol synthase,isopentyl pyrophosphate isomerase.

The prenyltransferase sequences of the present invention find use in the preparation of transformation constructs having a second expression cassette for the expression of additional sequences involved in tocopherol biosynthesis. Additional tocopherol biosynthesis sequences of interest in the present invention include, but are not limited to gamma-tocpherol methyltransferase (Shintani, et al. (1998) *Science* 282(5396): 2098–2100), tocopherol cyclase, and tocopherol methyltransferase.

A plant cell, tissue, organ, or plant into which the recombinant DNA constructs containing the expression constructs have been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of a prenyltransferase nucleic acid sequence.

Plant expression or transcription constructs having a prenyltransferase as the DNA sequence of interest for increased or decreased expression thereof may be employed with a wide variety of plant life, particularly, plant life involved in the production of vegetable oils for edible and industrial uses. Particularly preferred plants for use in the methods of the present invention include, but are not limnited to: Acacia, alfalfa, aneth, apple, apricot, artichoke, arugula, asparagus, avocado, banana, barley, beans, beet, blackberry, blueberry, broccoli,brussels sprouts, cabbage, canola, cantaloupe, carrot, cassava, cauliflower, celery, cherry, chicory, cilantro, citrus, clementines, coffee, corn, cotton, cucumber, Douglas fir, eggplant, endive, escarole, eucalyptus, fennel, figs, garlic, gourd, grape, grapefruit, honey dew,jicama, kiwifruit, lettuce, leeks, lemon, lime, Loblolly pine, mango, melon, mushroom, nectarine, nut, oat, oil palm, oil seed rape, okra, onion, orange, an ornamental plant, papaya, :parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. Most especially preferred are temperate oilseed crops. Temperate oilseed crops of interest include, but are not limited to, rapeseed (Canola and High Erucic Acid varieties), sunflower, safflower, cotton, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

Of particular interest, is the use of prenyltransferase constructs in plants to produce plants or plant parts, including, but not limited to leaves, stems, roots, reproductive, and seed, with a modified content of tocopherols in plant parts having transformed plant cells.

For immunological screening, antibodies to the protein can be prepared by injecting rabbits or mice with the purified protein or portion thereof, such methods of preparing antibodies being well known to those in the art. Either monoclonal or polyclonal antibodies can be produced, although typically polyclonal antibodies are more useful for gene isolation. Western analysis may be conducted to determine that a related protein is present in a crude extract of the desired plant species, as determined by cross-reaction with the antibodies to the encoded proteins. When cross-reactivity is observed, genes encoding the related proteins are isolated by screening expression libraries representing the desired plant species. Expression libraries can be constructed in a variety of commercially available vectors, including lambda gt11, as described in Sambrook, et al. (*Molecular Cloning: A Laboratory Manual*, Second Edition (1989) Cold Spring Harbor Laboratory, Cold Spring Harbor, N.Y.).

To confirm the activity and specificity of the proteins encoded by the identified nucleic acid sequences as prenyltransferase enzymes, in vitro assays are performed in insect cell cultures using baculovirus expression systems. Such baculovirus expression systems are known in the art and are described by Lee, et al. U.S. Pat. No. 5,348,886, the entirety of which is herein incorporated by reference.

In addition, other expression constructs may be prepared to assay for protein activity utilizing different expression systems. Such expression constructs are transformed into yeast or prokaryotic host and assayed for prenyltransferase activity. Such expression systems are known in the art and are readily available through commercial sources.

In addition to the sequences described in the present invention, DNA coding sequences useful in the present invention can be derived from algae, fungi, bacteria, mammalian sources, plants, etc. Homology searches in existing databases using signature sequences corresponding to conserved nucleotide and amino acid sequences of prenyltransferase can be employed to isolate equivalent, related genes from other sources such as plants and microorganisms. Searches in EST databases can also be employed. Furthermore, the use of DNA sequences encoding enzymes functionally enzymatically equivalent to those disclosed herein, wherein such DNA sequences are degenerate equivalents of the nucleic acid sequences disclosed herein in accordance with the degeneracy of the genetic code, is also encompassed by the present invention. Demonstration of the functionality of coding sequences identified by any of these methods can be carried out by complementation of mutants of appropriate organisms, such as Synechocystis, Shewanella, yeast, Pseudomonas, Rhodobacteria, etc., that lack specific biochemical reactions, or that have been mutated. The sequences of the DNA coding regions can be optimized by gene resynthesis, based on codon usage, for maximum expression in particular hosts.

For the alteration of tocopherol production in a host cell, a second expression construct can be used in accordance with the present invention. For example, the prenyltransferase expression construct can be introduced into a host cell in conjunction with a second expression construct having a nucleotide sequence for a protein involved in tocopherol biosynthesis.

The method of transformation in obtaining such transgenic plants is not critical to the instant invention, and various methods of plant transformation are currently available. Furthermore, as newer methods become available to transform crops, they may also be directly applied hereunder. For example, many plant species naturally susceptible toAgrobacterium infection may be successfully transformed via tripartite or binary vector methods of Agrobacterium mediated transformation. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation. In addition, techniques of microinjection, DNA particle bombardment, and electroporation have been developed which allow for the transformation of various monocot and dicot plant species.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall formation), the latter being permissible, so long as the vir genes are present in the transformed Agrobacterium host. The armed plasmid can give a mixture of normal plant cells and gall.

In some instances where Agrobacterium is used as the vehicle for transforming host plant cells, the expression or transcription construct bordered by the T-DNA border region (s) will be inserted into a broad host range vector capable of replication in *E. coli* and Agrobacterium, there being broad host range vectors described in the literature. Commonly used is pRK2 or derivatives thereof. See, for example, Ditta, et al., (*Proc. Nat. Acad. Sci., U.S.A.* (1980) 77: 7347–7351) and EPA 0 120 515, which are incorporated herein by reference. Alternatively, one may insert the sequences to be expressed in plant cells into a vector containing separate replication sequences, one of which stabilizes the vector in *E. coli*, and the other in Agrobacterium. See, for example, McBride, et al. (*Plant Mol. Biol.* (1990) 14: 269–276), wherein the pRiHRI (Jouanin, et al., *Mol. Gen. Genet.* (1985) 201: 370–374) origin of replication is utilized and provides for added stability of the plant expression vectors in host Agrobacterium cells.

Included with the expression construct and the T-DNA will be one or more markers, which allow for selection of transformed Agrobacterium and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

There are several possible ways to obtain the plant cells of this invention which contain multiple expression constructs. Any means for producing a plant comprising a construct having a DNA sequence encoding the expression construct of the present invention, and at least one other construct having another DNA sequence encoding an enzyme are encompassed by the present invention. For example, the expression construct can be used to transform a plant at the same time as the second construct either by inclusion of both expression constructs in a single transformation vector or by using separate vectors, each of which express desired genes. The second construct can be introduced into a plant which has already been transformed with the prenyltransferase expression construct, or alternatively, transformed plants, one expressing the prenyltransferase construct and one expressing the second construct, can be crossed to bring the constructs together in the same plant.

The nucleic acid sequences of the present invention can be used in constructs to provide for the expression of the sequence in a variety of host cells, both prokaryotic eukaryotic. Host cells of the present invention preferably include monocotyledenous and dicotyledenous plant cells.

In general, the skilled artisan is familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., *Molecular Cloning: A Laboratory Manual*, Cold Spring Harbor Press (1989); Maliga et al., *Methods in Plant Molecular Biology*, Cold Spring Harbor Press (1995), the entirety of which is herein incorporated by reference; Birren et al., *Genome Analysis: Analyzing DNA*, 1, Cold Spring Harbor, N.Y., the entirety of which is herein incorporated by reference).

Methods for the expression of sequences in insect host cells are known in the art. Baculovirus expression vectors are recombinant insect viruses in which the coding sequence for a chosen foreign gene has been inserted behind a baculovirus promoter in place of the viral gene, e.g., polyhedrin (Smith and Summers, U.S. Pat. No. , 4,745,051, the entirety of which is incorporated herein by reference). Baculovirus expression vectors are known in the art, and are described for example in Doerfler, *Curr. Top. Microbiol. Immunol.* 131: 51–68 (1968); Luckow and Summers, *Bio/Technology* 6: 47–55 (1988a); Miller, *Annual Review of Microbiol.* 42: 177–199 (1988); Summers, *Curr. Comm. Molecular Biology*, Cold Spring Harbor Press, Cold Spring Harbor, N.Y. (1988); Summers and Smith, *A Manual of*

*Methods for Baculovirus Vectors and Insect Cell Culture Procedures*, Texas Ag. Exper. Station Bulletin No. 1555 (1988), the entireties of which is herein incorporated by reference)

Methods for the expression of a nucleic acid sequence of interest in a fungal host cell are known in the art. The fungal host cell may, for example, be a yeast cell or a filamentous fungal cell. Methods for the expression of DNA sequences of interest in yeast cells are generally described in "Guide to yeast genetics and molecular biology", Guthrie and Fink, eds. Methods in enzymology, Academic Press, Inc. Vol 194 (1991) and Gene expression technology", Goeddel ed, Methods in Enzymology, Academic Press, Inc., Vol 185 (1991).

Mammalian cell lines available as hosts for expression are known in the art and include many immortalized cell lines available from the American Type Culture Collection (ATCC, Manassas, Va.), such as HeLa cells, Chinese hamster ovary (CHO) cells, baby hamster kidney (BHK) cells and a number of other cell lines. Suitable promoters for mammalian cells are also known in the art and include, but are not limited to, viral promoters such as that from Simian Virus 40 (SV40) (Fiers et al., *Nature* 273:113 (1978), the entirety of which is herein incorporated by reference), Rous sarcoma virus (RSV), adenovirus (ADV) and bovine papilloma virus (BPV). Mammalian cells may also require terminator sequences and poly-A addition sequences. Enhancer sequences which increase expression may also be included and sequences which promote amplification of the gene may also be desirable (for example methotrexate resistance genes).

Vectors suitable for replication in mammalian cells are well known in the art, and may include viral replicons, or sequences which insure integration of the appropriate sequences encoding epitopes into the host genome. Plasmid vectors that greatly facilitate the construction of recombinant viruses have been described (see, for example, Mackett et al, *J Virol.* 49:857 (1984); Chakrabarti et al., *Mol. Cell. Biol.* 5:3403 (1985); Moss, In: *Gene Transfer Vectors For Mammalian Cells* (Miller and Calos, eds., Cold Spring Harbor Laboratory, N.Y., p. 10, (1987); all of which are herein incorporated by reference in their entirety).

The invention now being generally described, it will be more readily understood by reference to the following examples which are included for purposes of illustration only and are not intended to limit the present invention.

EXAMPLES

EXAMPLE 1

Identification of Prenyltransferase Sequences

PSI-BLAST (Altschul, et al. (1997) *Nuc Acid Res* 25: 3389–3402) profiles were generated for both the straight chain and aromatic classes of prenyltransferases. To generate the straight chain profile, a prenyl-transferase from *Porphyra purpurea* (Genbank accession 1709766) was used as a query against the NCBI non-redundant protein database. The *E. coli* enzyme involved in the formation of ubiquinone, ubiA (genbank accession 1790473) was used as a starting sequence to generate the aromatic prenyltransferase profile. These profiles were used to search public and proprietary DNA and protein data bases. In Arabidopsis seven putative prenyltransferases of the straight-chain class were identified, ATPT1, (SEQ ID NO: 9), ATPT7 (SEQ ID NO: 10), ATPT8 (SEQ ID NO: 11), ATPT9 (SEQ ID NO: 13), ATPT10 (SEQ ID NO: 14), ATPT11 (SEQ ID NO: 15), and ATPT12 (SEQ ID NO: 16) and five were identified of the aromatic class, ATPT2 (SEQ ID NO: 1), ATPT3 (SEQ ID NO: 3), ATPT4 (SEQ ID NO: 5), ATPT5 (SEQ ID NO: 7), ATPT6 (SEQ ID NO: 8). Additional prenyltransferase sequences from other plants related to the aromatic class of prenyltransferases, such as soy (SEQ ID NOs: 19–23, the deduced amino acid sequence of SEQ ID NO: 23 is provided in SEQ ID NO: 24) and maize (SEQ ID NOs: 25–29, and 31) are also identified. The deduced amino acid sequence of ZMPT5 (SEQ ID NO: 29) is provided in SEQ ID NO: 30.

Searches are performed on a Silicon Graphics Unix computer using additional Bioaccellerator hardware and GenWeb software supplied by Compugen Ltd. This software and hardware enables the use of the Smith-Waterman algorithm in searching DNA and protein databases using profiles as queries. The program used to query protein databases is profilesearch. This is a search where the query is not a single sequence but a profile based on a multiple alignment of amino acid or nucleic acid sequences. The profile is used to query a sequence data set, i.e., a sequence database. The profile contains all the pertinent information for scoring each position in a sequence, in effect replacing the "scoring matrix" used for the standard query searches. The program used to query nucleotide databases with a protein profile is tprofilesearch. Tprofilesearch searches nucleic acid databases using an amino acid profile query. As the search is running, sequences in the database are translated to amino acid sequences in six reading frames. The output file for tprofilesearch is identical to the output file for profilesearch except for. an additional column that indicates the frame in which the best alignment occurred.

The Smith-Waterman algorithm, (Smith and Waterman (1981) supra), is used to search for similarities between one sequence from the query and a group of sequences contained in the database. E score values as well as other sequence information, such as conserved peptide sequences are used to identify related sequences.

To obtain the entire coding region corresponding to the Arabidopsis prenyltransferase sequences, synthetic oligonucleotide primers are designed to amplify the 5' and 3' ends of partial cDNA clones containing prenyltransferase sequences. Primers are designed according to the respective Arabidopsis prenyltransferase sequences and used in Rapid Amplification of cDNA Ends (RACE) reactions (Frohman et al. (1988) *Proc. Nati. Acad. Sci. USA* 85: 8998–9002) using the Marathon cDNA amplification kit (Clontech Laboratories Inc, Palo Alto, Calif.).

Additional BLAST searches are performed using the ATPT2 sequence, a sequence in the class of aromatic prenyl transferases. Additional sequences are identified in soybean libraries that are similar to the ATPT2 sequence. The additional soybean sequence demonstrates 80% identity and 91% similarity at the amino acid sequence.

Figure 1:
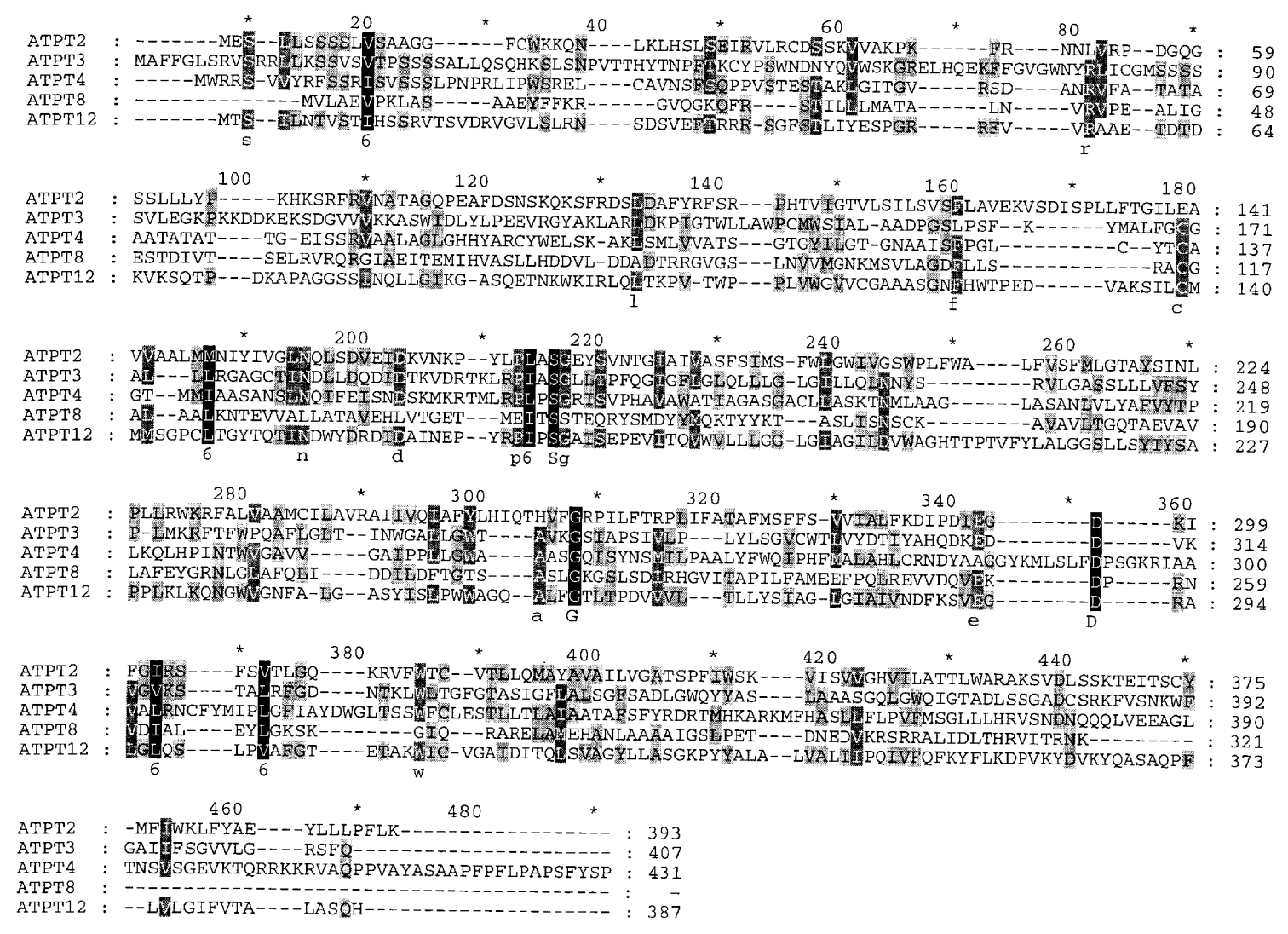

Amino acid sequence alignments between ATPT2 (SEQ ID NO: 2), ATPT3 (SEQ ID NO: 4), ATPT4 (SEQ ID NO: 6), ATPT8 (SEQ ID NO: 12), and ATPT12 (SEQ ID NO: 17) are performed using ClustalW (FIG. 1), and the percent identity and similarities are provided in Table 1 below.

TABLE 1

|       |            | ATPT2 | ATPT3 | ATPT4 | ATPT8 | ATPT12 |
|-------|------------|-------|-------|-------|-------|--------|
| ATPT2 | % Identity |       | 12    | 13    | 11    | 15     |
|       | % similar  |       | 25    | 25    | 22    | 32     |
|       | % Gap      |       | 17    | 20    | 20    | 9      |

TABLE 1-continued

|  |  | ATPT2 | ATPT3 | ATPT4 | ATPT8 | ATPT12 |
|---|---|---|---|---|---|---|
| ATPT3 | % Identity |  |  | 12 | 6 | 22 |
| % similar |  |  |  | 29 | 16 | 38 |
| % Gap |  |  |  | 20 | 24 | 14 |
| ATPT4 | % Identity |  |  |  | 9 | 14 |
| % similar |  |  |  |  | 18 | 29 |
| % Gap |  |  |  |  | 26 | 19 |
| ATPT8 | % Identity |  |  |  |  | 7 |
| % similar |  |  |  |  |  | 19 |
| % Gap |  |  |  |  |  | 20 |
| ATPT12 | % Identity |  |  |  |  |  |
| % similar |  |  |  |  |  |  |
| % Gap |  |  |  |  |  |  |

EXAMPLE 2

Preparation of Expression Constructs

A plasmid containing the napin cassette derived from pCGN3223 (described in U.S. Pat. No. 5,639,790, the entirety of which is incorporated herein by reference) was modified to make it more useful for cloning large DNA fragments containing multiple restriction sites, and to allow the cloning of multiple napin fusion genes into plant binary transformation vectors. An adapter comprised of the self annealed oligonucleotide of sequence CGCGATTTAAATG-GCGCGCCCTGCAGGCGGCCGCCTG-CAGGGCGCGCCATTTAAAT (SEQ ID NO: 40) was ligated into the cloning vector pBC SK+ (Stratagene) after digestion with the restriction endonuclease BssHII to construct vector pCGN7765. Plamids pCGN3223 and pCGN7765 were digested with NotI and ligated together. The resultant vector, pCGN7770, contains the pCGN7765 backbone with the napin seed specific expression cassette from pCGN3223.

The cloning cassette, pCGN7787, essentially the same regulatory elements as pCGN7770, with the exception of the napin regulatory regions of pCGN7770 have been replaced with the double CAMV 35S promoter and the tml polyadenylation and transcriptional termination region.

A binary vector for plant transformation, pCGN5139, was constructed from pCGN1558 (McBride and Summerfelt, (1990) Plant Molecular Biology, 14: 269–276). The polylinker of pCGN1558 was replaced as a HindHII/Asp718 fragment with apolylinker containing unique restriction endonuclease sites, AscI, PacI, XbaI, SwaI, BamHI, and NotI. The Asp718 and HindIII restriction endonuclease sites are retained in pCGN5139.

A series of turbo binary vectors are constructed to allow for the rapid cloning of DNA sequences into binary vectors containing transcriptional initiation regions (promoters) and transcriptional termination regions.

The plasmid pCGN8618 was constructed by ligating oligonucleotides 5'-TCGAGGATCCGCGGCCGCAAGCTTCCTGCAGG-3' (SEQ ID NO: 41) and 5'-TCGACCTGCAGGAAGCTTGCGGCCGCGGATCC-3' (SEQ ID NO: 42) into SalI/XhoI-digested pCGN7770. A fragment containing the napin promoter, polylinker and napin 3' region was excised from pCGN8618 by digestion with Asp718I; the fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the napin promoter was closest to the blunted Asp718I site of pCGN5139 and the napin 3' was closest to the blunted HindIII site was subjected to sequence analysis to confirm both the insert orientation and the integrity of cloning junctions. The resulting plasmid was designated pCGN8622.

The plasmid pCGN8619 was constructed by ligating oligonucleotides 5'-TCGACCTGCAGGAAGCTTGCGGCCGCGGATCC-3' (SEQ ID NO: 43) and 5'-TCGAGGATCCGCGGCCGCAAGCTTCCTGCAGG-3' (SEQ ID NO: 44) into SalI/XhoI-digested pCGN7770. A fragment containing the napin promoter, polylinker and napin 3' region was removed from pCGN8619 by digestion with Asp718I; the fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the napin promoter was closest to the blunted Asp718I site of pCGN5139 and the napin 3' was closest to the blunted HindIII site was subjected to sequence analysis to confirm both the insert orientation and the integrity of cloning junctions. The resulting plasmid was designated pCGN8623.

The plasmid pCGN8620 was constructed by ligating oligonucleotides 5'-TCGAGGATCCGCGGCCGCAAGCTTCCTGCAGGA GCT-3' (SEQ ID NO: 45) and 5'-CCTGCAGGAAGCTTGCGGCCGCGGATCC-3' (SEQ ID NO: 46) into SalI/SacI-digested pCGN7787. A fragment containing the d35S promoter, polylinker and tml 3' region was removed from pCGN8620 by complete digestion with Asp718I and partial digestion with NotI. The fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the d35S promoter was closest to the blunted Asp718I site of pCGN5139 and the tml 3' was closest to the blunted HindIII site was subjected to sequence analysis to confirm both the insert orientation and the integrity of cloning junctions. The resulting plasmid was designated pCGN8624.

The plasmid pCGN8621 was constructed by ligating oligonucleotides 5'-TCGACCTGCAGGAAGCTTGCGGCCGCGGATCCA GCT-3' (SEQ ID NO: 47) and 5'-GGATCCGCGGCCGCAAGCTTCCTGCAGG-3' (SEQ ID NO: 48) into SalI/SacI-digested pCGN7787. A fragment containing the d35S promoter, polylinker and tml 3' region was removed from pCGN8621 by complete digestion with Asp718I and partial digestion with NotI. The fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the d35S promoter was closest to the blunted Asp718I site of pCGN5139 and the tml 3' was closest to the blunted HindIII site was subjected to sequence analysis to confirm both the insert orientation and the integrity of cloning junctions. The resulting plasmid was designated pCGN8625.

The plasmid construct pCGN8640 is a modification of pCGN8624 described above. A 938bp PstI fragment isolated from transposon Tn7 which encodes bacterial spectinomycin and streptomycin resistance (Fling et al. (1985), *Nucleic*

Acids Research 13(19): 7095–7106), a determinant for E. coli and Agrobacterium selection, was blunt ended with Pfu polymerase. The blunt ended fragment was ligated into pCGN8624 that had been digested with SpeI and blunt ended with Pfu polymerase. The region containing the PstI fragment was sequenced to confirm both the insert orientation and the integrity of cloning junctions.

The spectinomycin resistance marker was introduced into pCGN8622 and pCGN8623 as follows. A 7.7 Kbp AvrII-SnaBI fragment from pCGN8640 was ligated to a 10.9 Kbp AvrII-SnaBI fragment from pCGN8623 or pCGN8622, described above. The resulting plasmids were pCGN8641 and pCGN8643, respectively.

The plasmid pCGN8644 was constructed by ligating oligonucleotides 5'-GATCACCTGCAGGAAGCTTGCGGCCGCGGATCCA ATGCA-3' (SEQ ID NO: 49) and 5'-TTGGATCCGCGGCCGCAAGCTTCCTGCAGGT-3' (SEQ ID NO: 50) into BamHI-PstI digested pCGN8640.

Synthetic oligonulceotides were designed for use in Polymerase Chain Reactions (PCR) to amplify the coding sequences of ATPT2, ATPT3, ATPT4, ATPT8, and ATPT12 for the preparation of expression constructs and are provided in Table 2 below.

TABLE 2

| Name | Restriction Site | Sequence | SEQ ID NO: |
|---|---|---|---|
| ATPT2 | 5' NotI | GGATCCGCGGCCGCACAATGGAGTC TCTGCTCTCTAGTTCT | 51 |
| ATPT2 | 3' SseI | GGATCCTGCAGGTCACTTCAAAAAA GGTAACAGCAAGT | 52 |
| ATPT3 | 5' NotI | GGATCCGCGGCCGCACAATGGCGTT TTTTGGGCTCTCCCGTGTTT | 53 |
| ATPT3 | 3' SseI | GGATCCTGCAGGTTATTGAAAACTT CTTCCAAGTACAACT | 54 |
| ATPT4 | 5' NotI | GGATCCGCGGCCGCACAATGTGGCG AAGATCTGTTGTT | 55 |
| ATPT4 | 3' SseI | GGATCCTGCAGGTCATGGAGAGTAG AAGGAAGGAGCT | 56 |
| ATPT8 | 5' NotI | GGATCCGCGGCCGCACAATGGTACT TGCCGAGGTTCCAAAGCTTGCCTCT | 57 |
| ATPT8 | 3' SseI | GGATCCTGCAGGTCACTTGTTTCTG GTGATGACTCTAT | 58 |
| ATPT12 | 5' NotI | GGATCCGCGGCCGCACAATGACTTC GATTCTCAACACT | 59 |
| ATPT12 | 3' SseI | GGATCCTGCAGGTCAGTGTTGCGAT GCTAATGCCGT | 60 |

The coding sequences of ATPT2, ATPT3, ATPT4, ATPT8, and ATPT12 were all amplified using the respective PCR primers shown in Table 2 above and cloned into the TopoTA vector (Invitrogen). Constructs containing the respective prenyltransferase sequences were digested with NotI and Sse83871 and cloned into the turbobinary vectors described above.

The sequence encoding ATPT2 prenyltransferase (SEQ ID NO: 1) was cloned in the sense orientation into pCGN8640 to produce the plant transformation construct pCGN10800 (FIG. 2). The ATPT2 sequence is under control of the 35S promoter.

Figure 3:
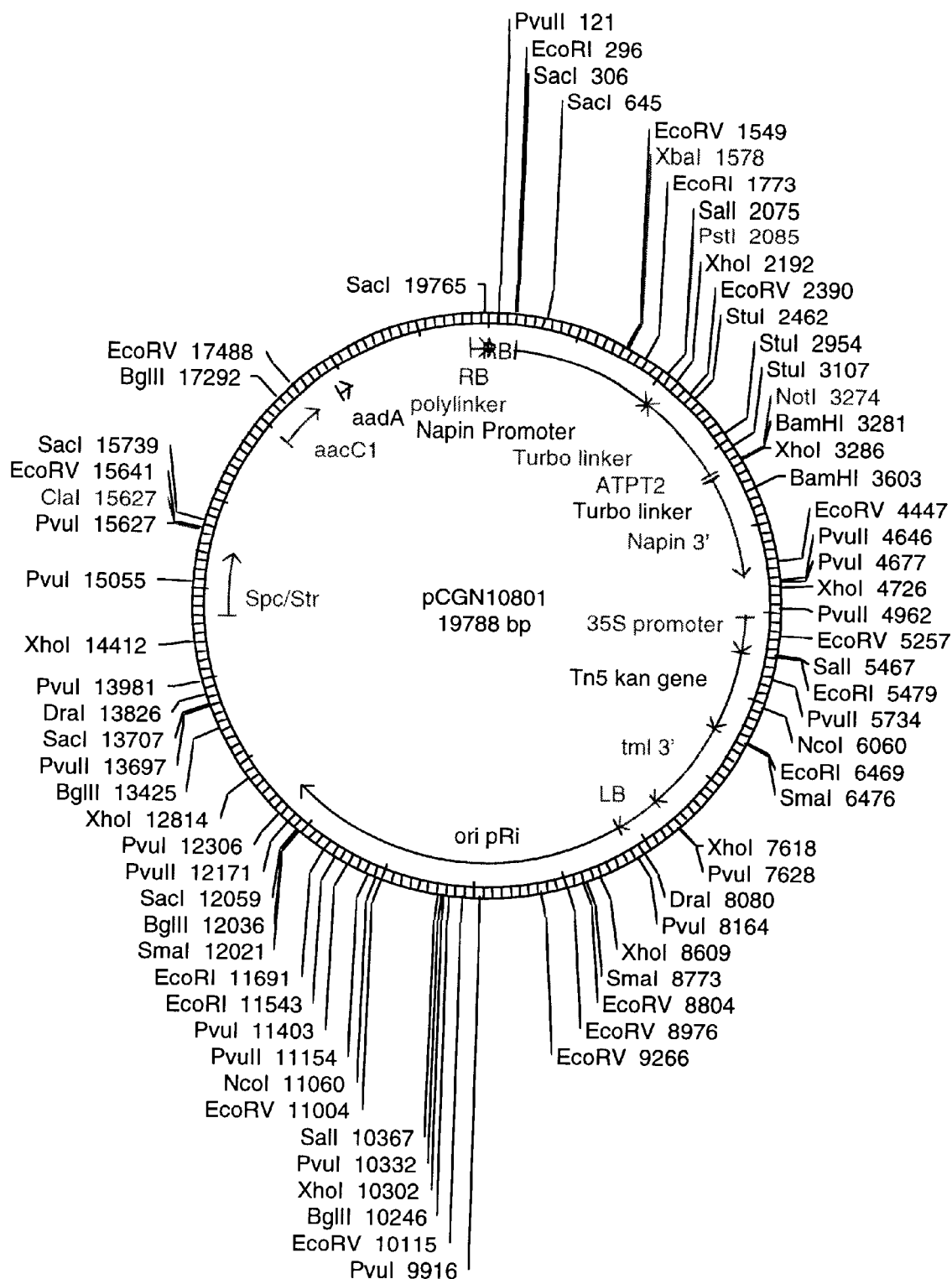
FIG. 3 provides a schematic picture of the expression construct pCGN10801.

The ATPT2 sequence (SEQ ID NO: 1) was also cloned in the antisense orientation into the construct pCGN8641 to create pCGN10801 (FIG. 3). This construct provides for the antisense expression of the ATPT2 sequence from the napin promoter.

The ATPT2 coding sequence (SEQ ID NO: 1) was also cloned in the antisense orientation into the vector pCGN8643 to create the plant transformation construct pCGN10802.

Figure 4:
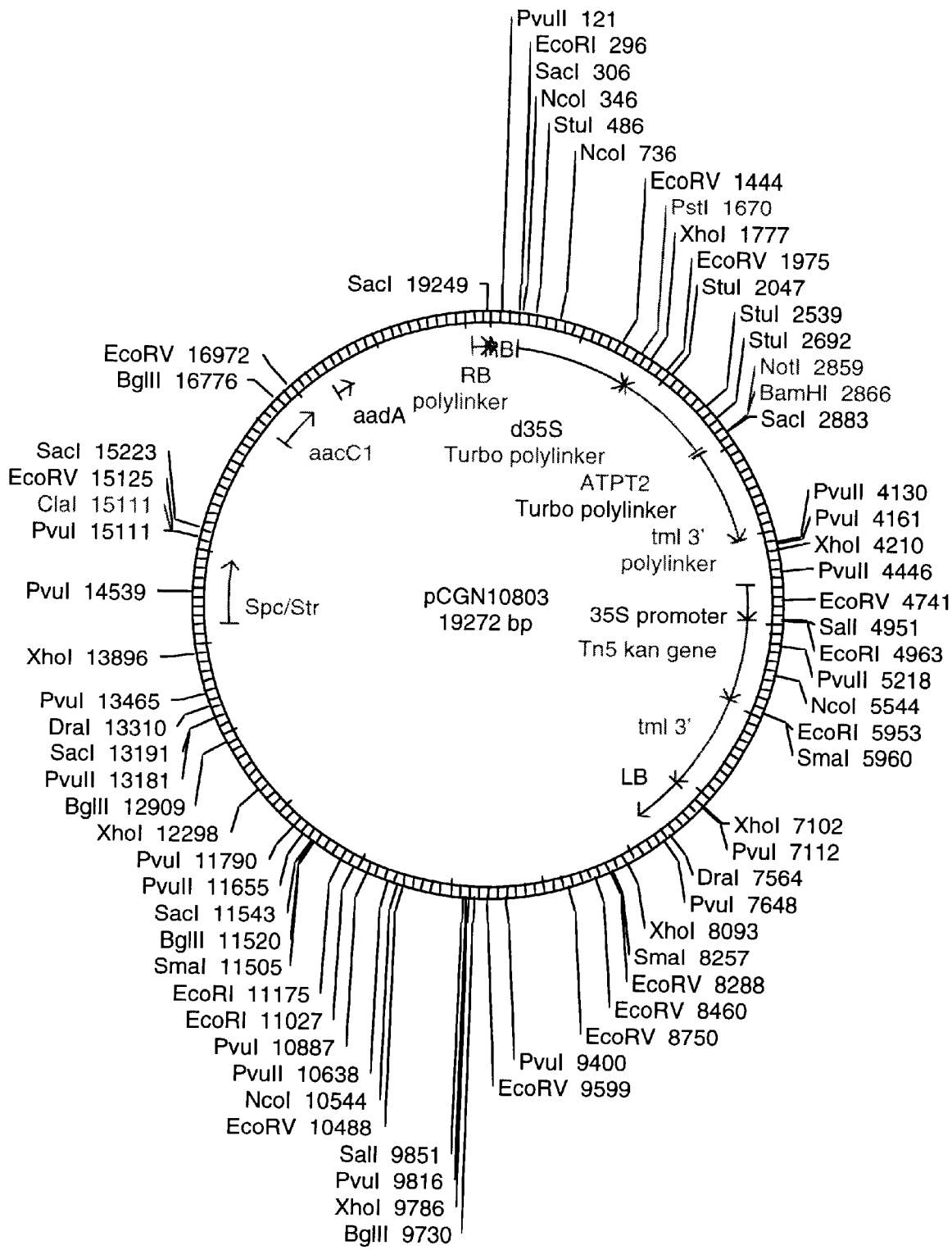
FIG. 4 provides a schematic picture of the expression construct pCGN10803.

The ATPT2 coding sequence (SEQ ID NO: 1) was also cloned in the antisense orientation into the vector pCGN8644 to create the plant transformation construct pCGN10803 (FIG. 4).

Figure 5:
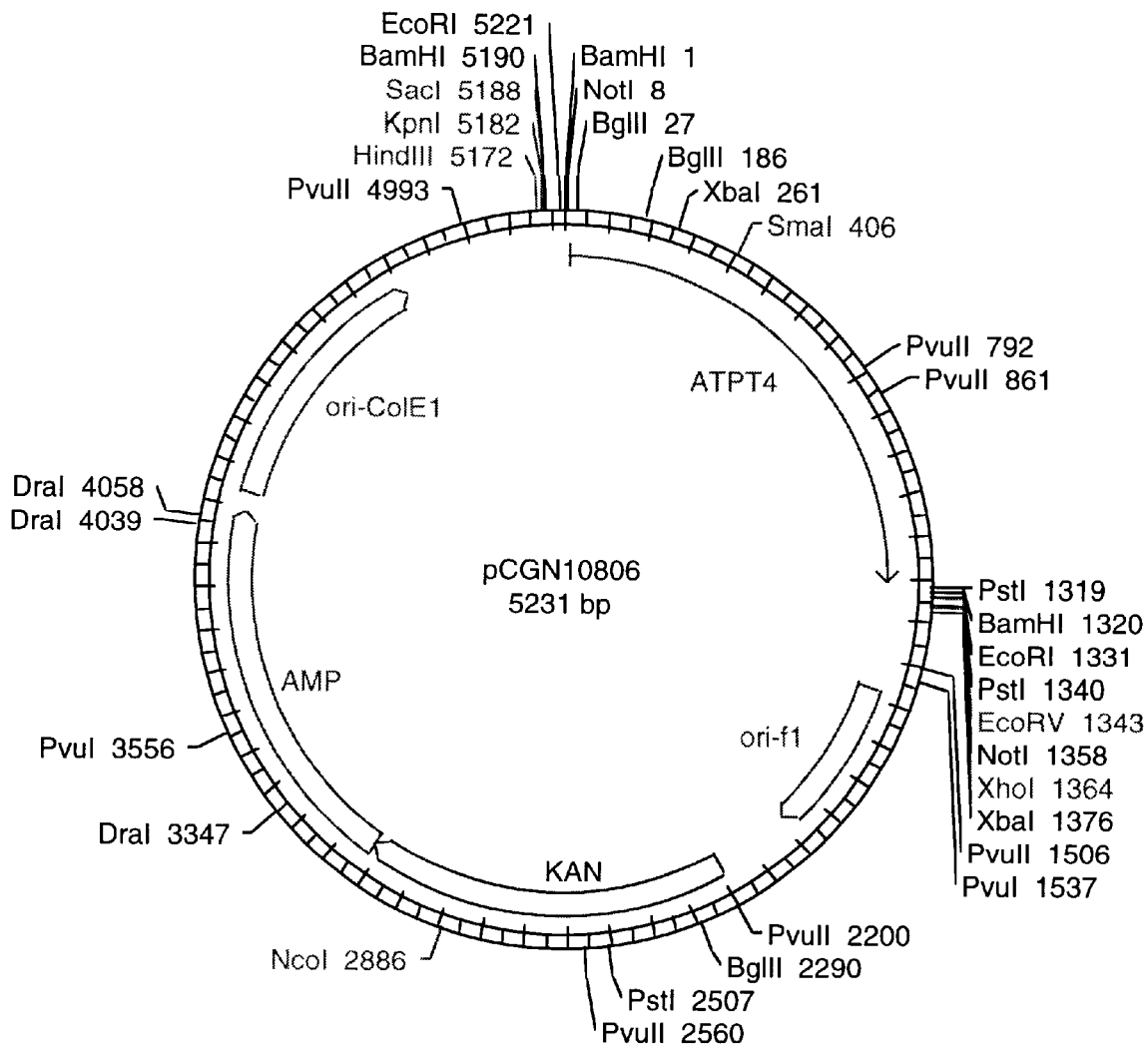
FIG. 5 provides a schematic picture of the expression construct pCGN10806.

The ATPT4 coding sequence (SEQ ID NO: 5) was cloned into the vector pCGN864 to create the plant transformation construct pCGN10806 (FIG. 5).

Figure 6:
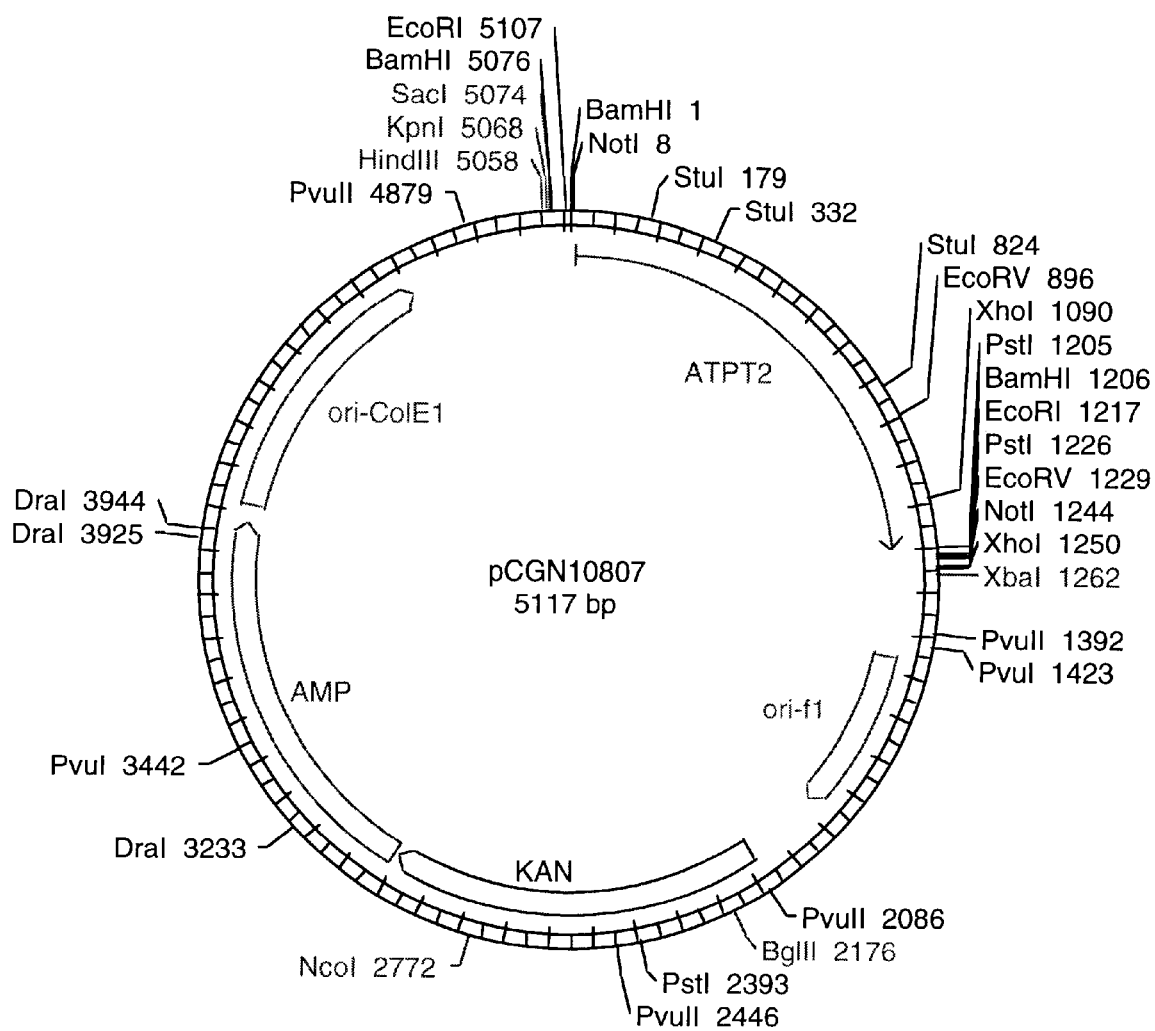
FIG. 6 provides a schematic picture of the expression construct pCGN10807.

The ATPT2 coding sequence (SEQ ID NO: 1) was cloned into the vector pCGN864 to create the plant transformation construct pCGN10807 (FIG. 6).

Figure 7:
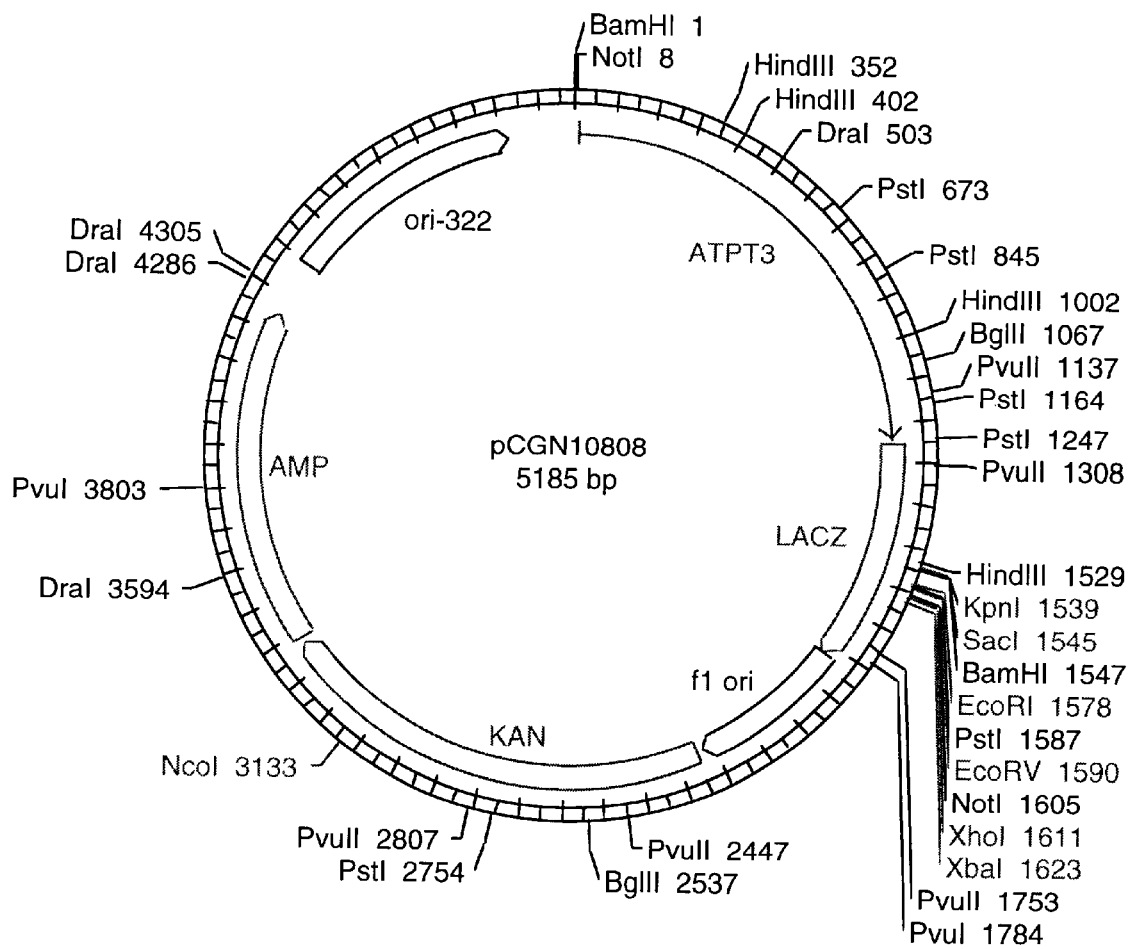
FIG. 7 provides a schematic picture of the expression construct pCGN10808.
Figure 8:
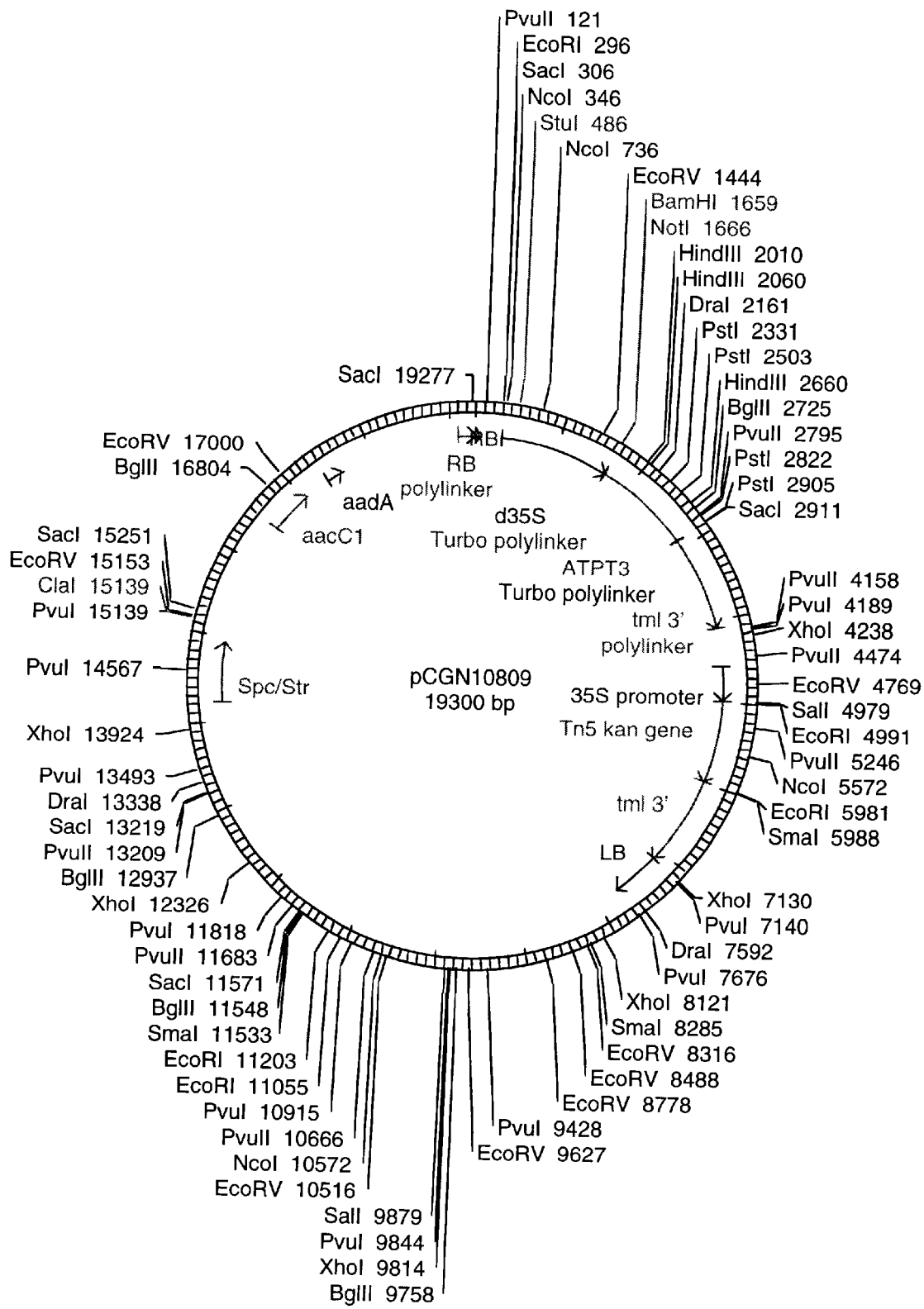
FIG. 8 provides a schematic picture of the expression construct pCGN10809.
Figure 9:
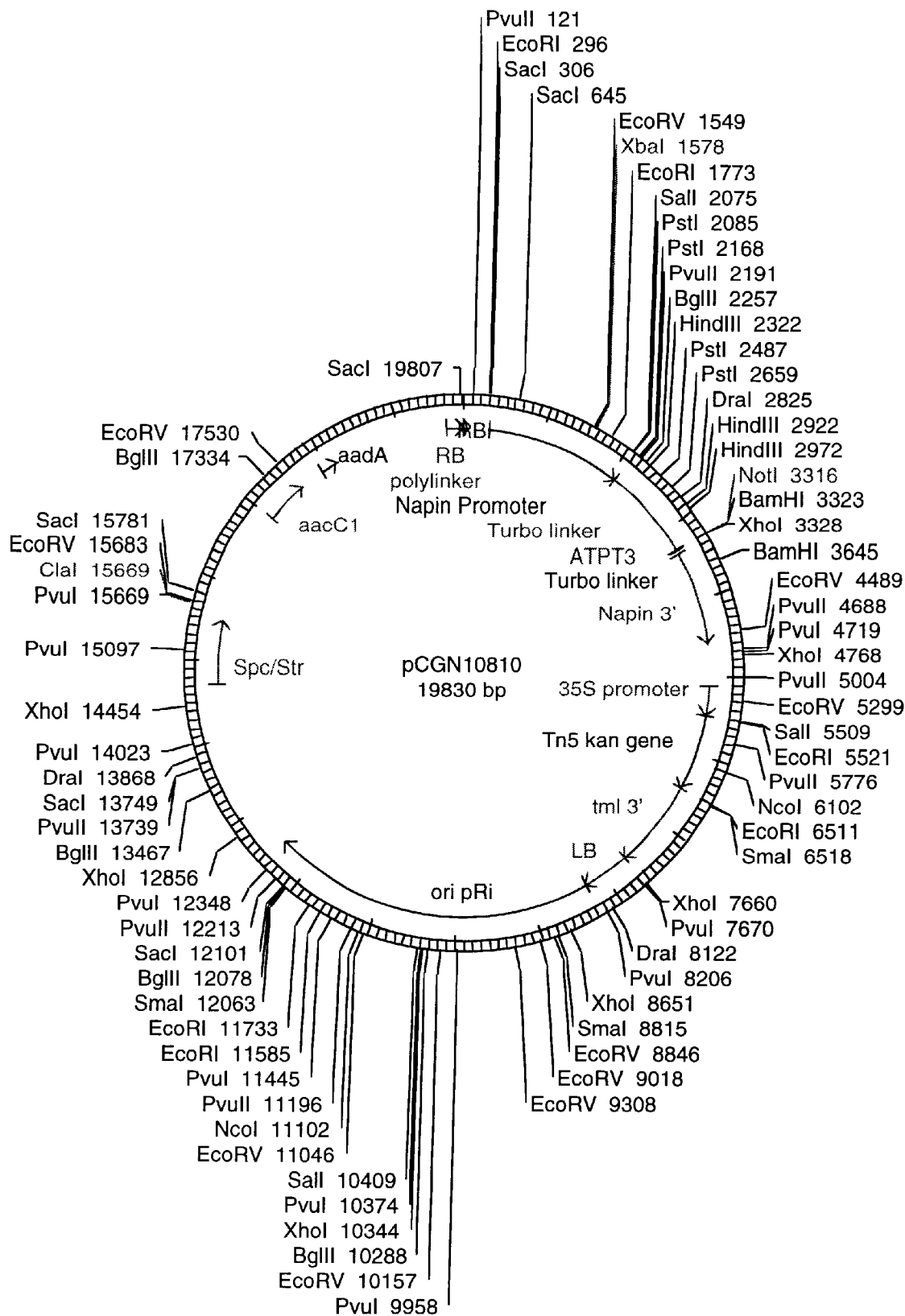
FIG. 9 provides a schematic picture of the expression construct pCGN10810.
Figure 10:
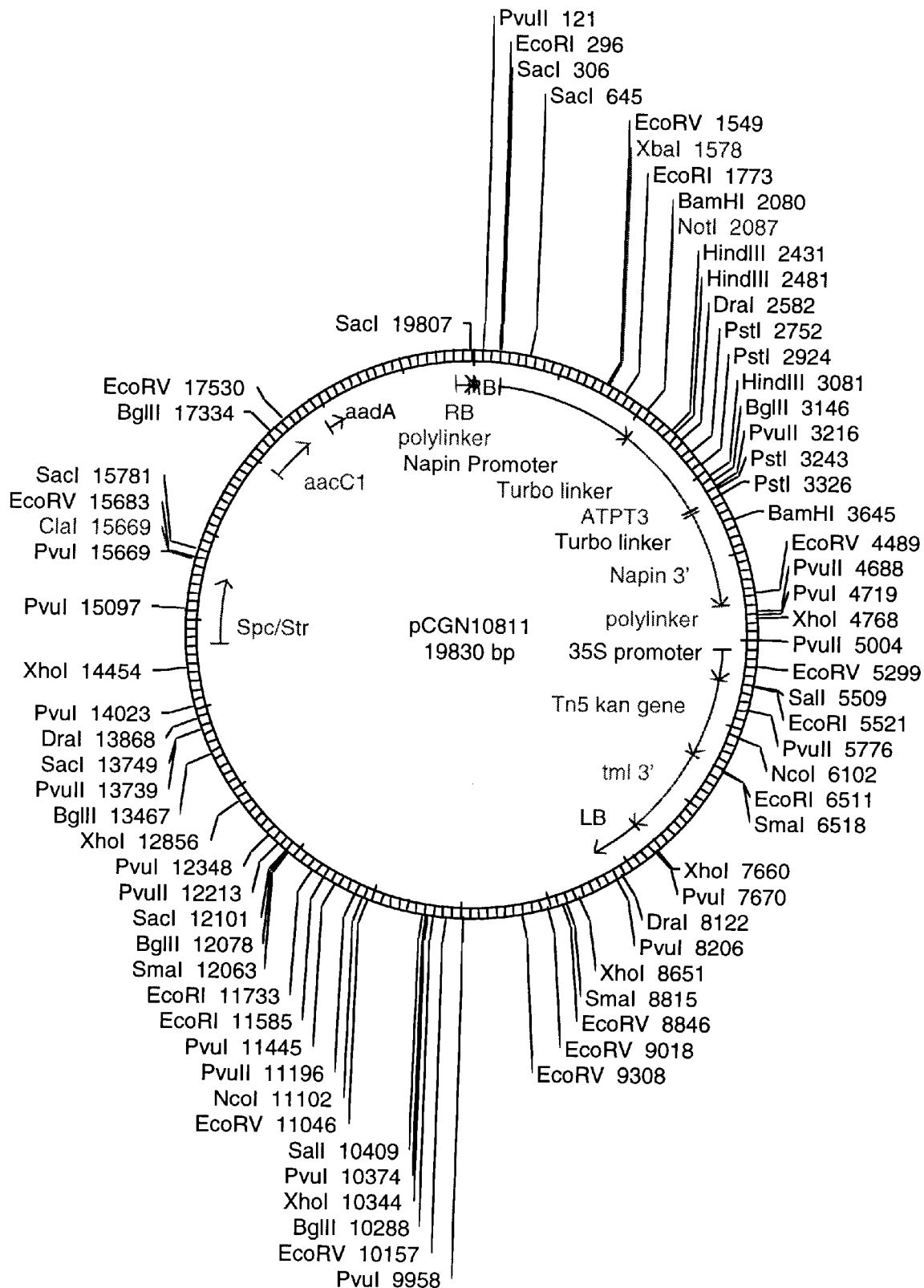
FIG. 10 provides a schematic picture of the expression construct pCGN10811.
Figure 11:
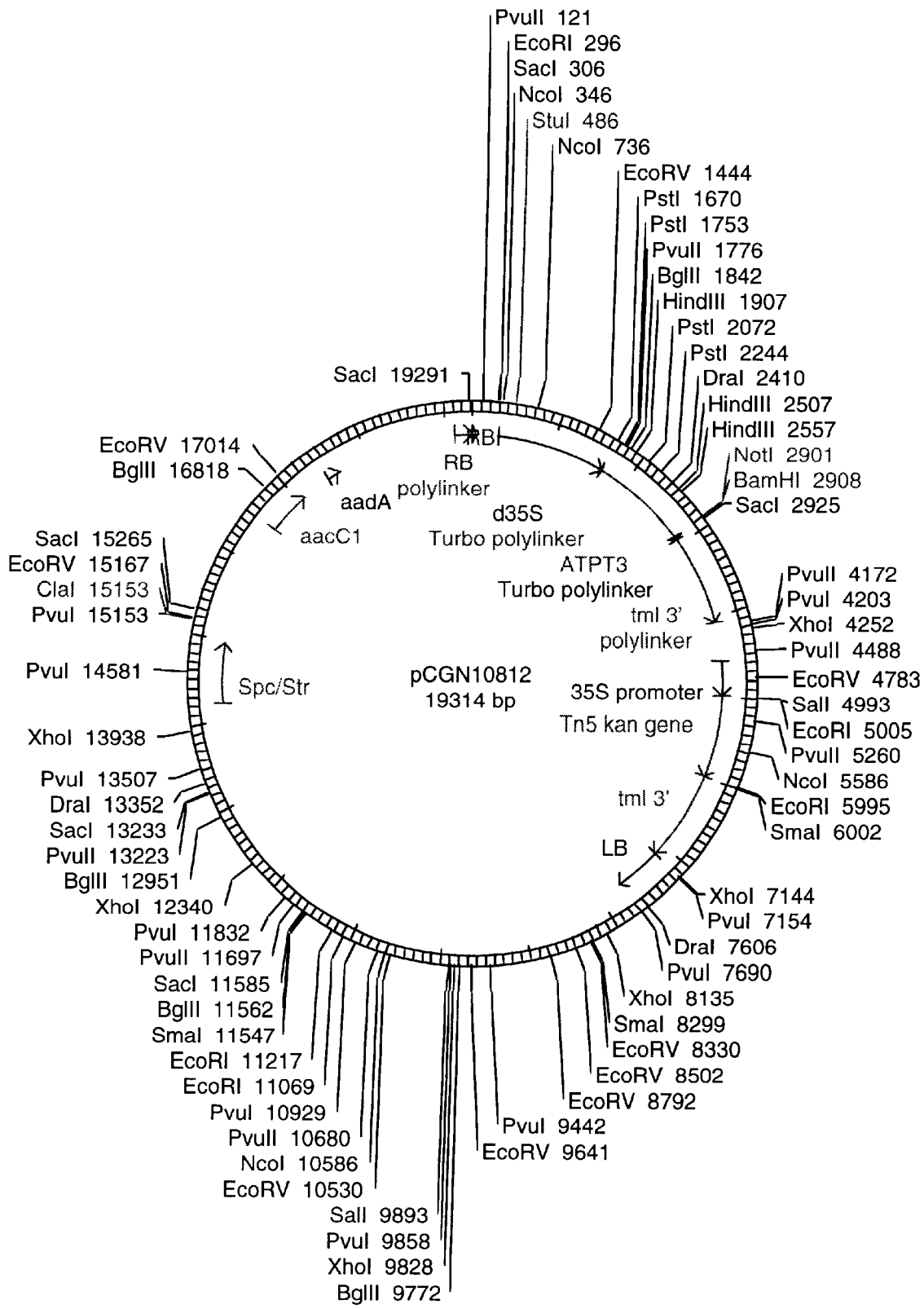
FIG. 11 provides a schematic picture of the expression construct pCGN10812.

The ATPT3 coding sequence (SEQ ID NO: 3) was cloned into the vector pCGN864 to create the plant transformation construct pCGN10808 (FIG. 7). The ATPT3 coding sequence (SEQ ID NO: 3) was cloned in the sense orientation into the vector pCGN8640 to create the plant transformation construct pCGN10809 (FIG. 8). The ATPT3 coding sequence (SEQ ID NO: 3) was cloned in the antisense orientation into the vector pCGN8641 to create the plant transformation construct pCGN10810 (FIG. 9). The ATPT3 coding sequence (SEQ ID NO: 3) was cloned into the vector pCGN8643 to create the plant transformation construct pCGN10811 (FIG. 10). The ATPT3 coding sequence (SEQ ID NO: 3) was cloned into the vector pCGN8640 to create the plant transformation construct pCGN10812 (FIG. 11).

Figure 12:
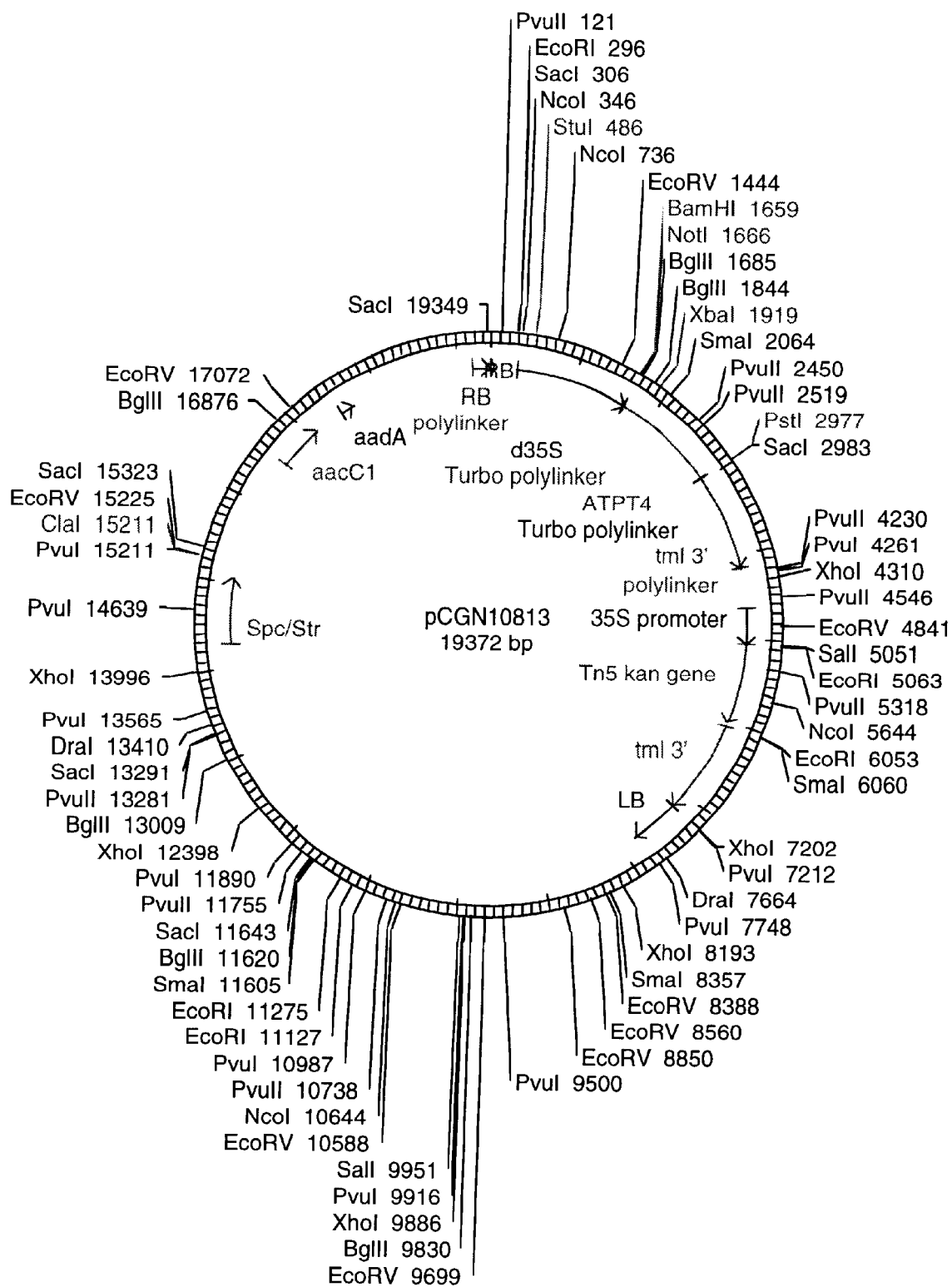
FIG. 12 provides a schematic picture of the expression construct pCGN10813.
Figure 13:
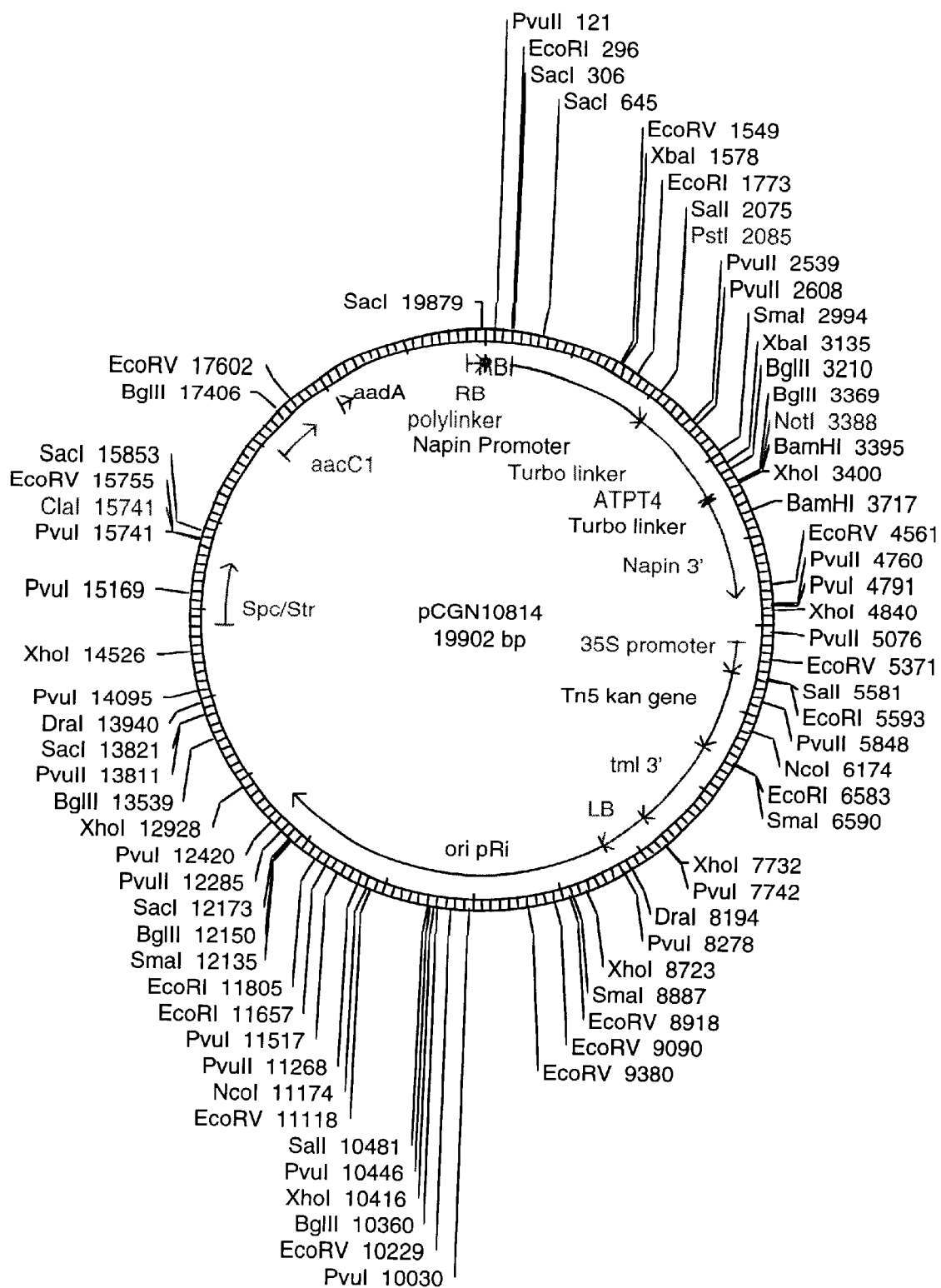
FIG. 13 provides a schematic picture of the expression construct pCGN10814.
Figure 14:
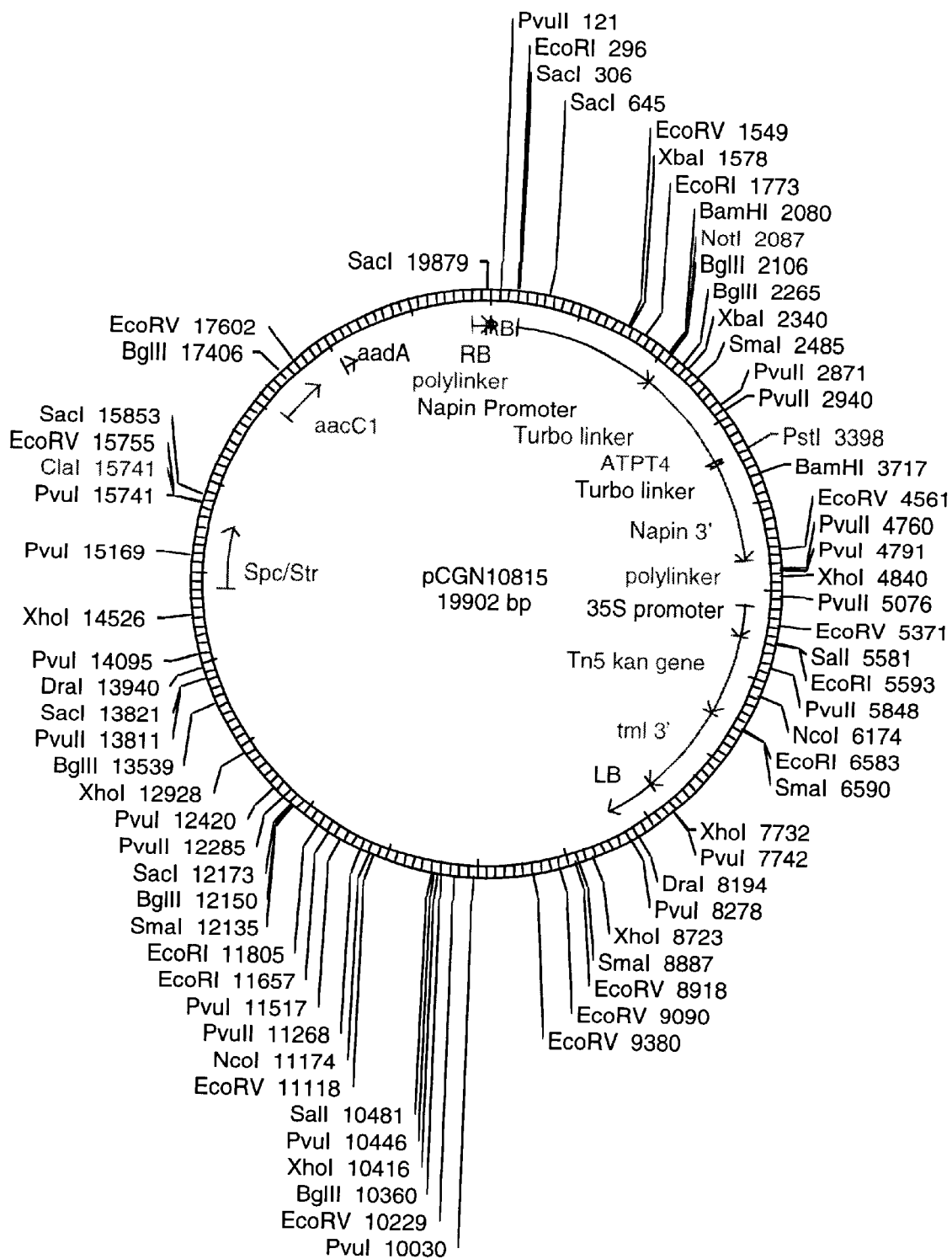
FIG. 14 provides a schematic picture of the expression construct pCGN10815.
Figure 15:
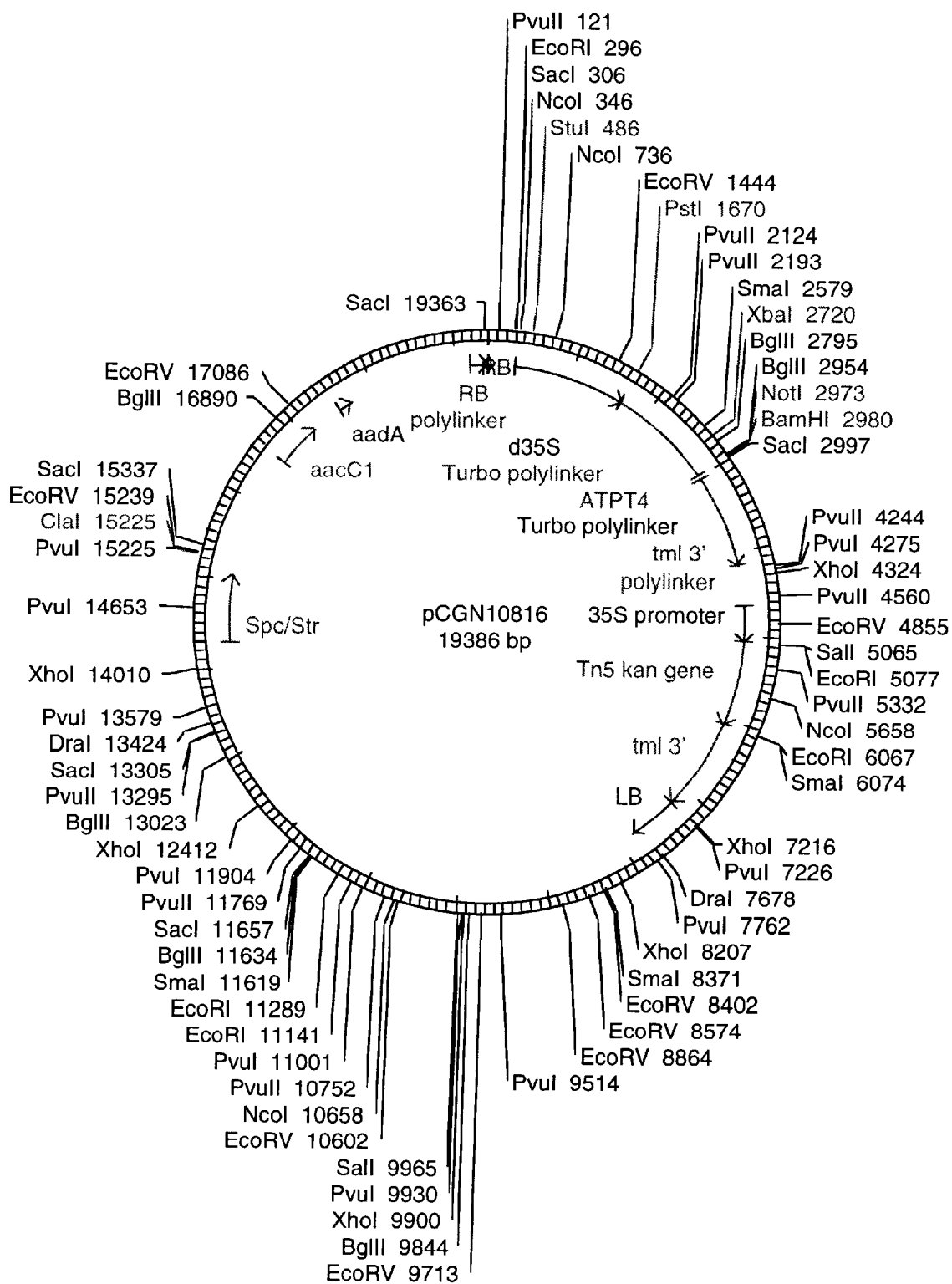
FIG. 15 provides a schematic picture of the expression construct pCGN10816.

The ATPT4 coding sequence (SEQ ID NO: 5) was cloned into the vector pCGN8640 to create the plant transformation construct pCGN10813 (FIG. 12). The ATPT4 coding sequence (SEQ ID NO: 5) was cloned into the vector pCGN8643 to create the plant transformation construct pCGN10814 (FIG. 13). The ATPT4 coding sequence (SEQ ID NO: 5) was cloned into the vector pCGN8641 to create the plant transformation construct pCGN10815 (FIG. 14). The ATPT4 coding sequence (SEQ ID NO: 5) was cloned in the antisense orientation into the vector pCGN8644 to create the plant transformation construct pCGN10816 (FIG. 15).

Figure 16:
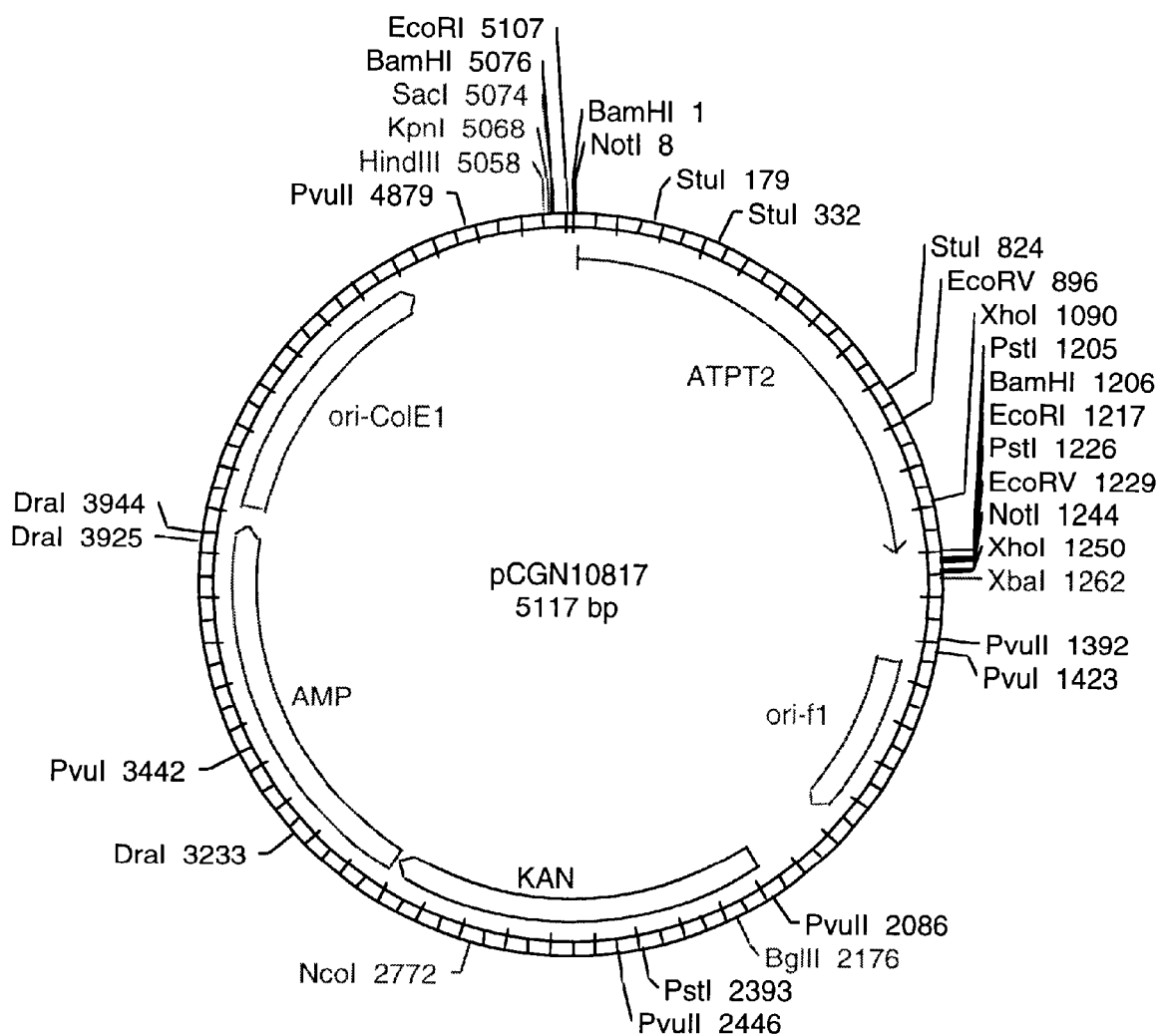
FIG. 16 provides a schematic picture of the expression construct pCGN10817.
Figure 17:
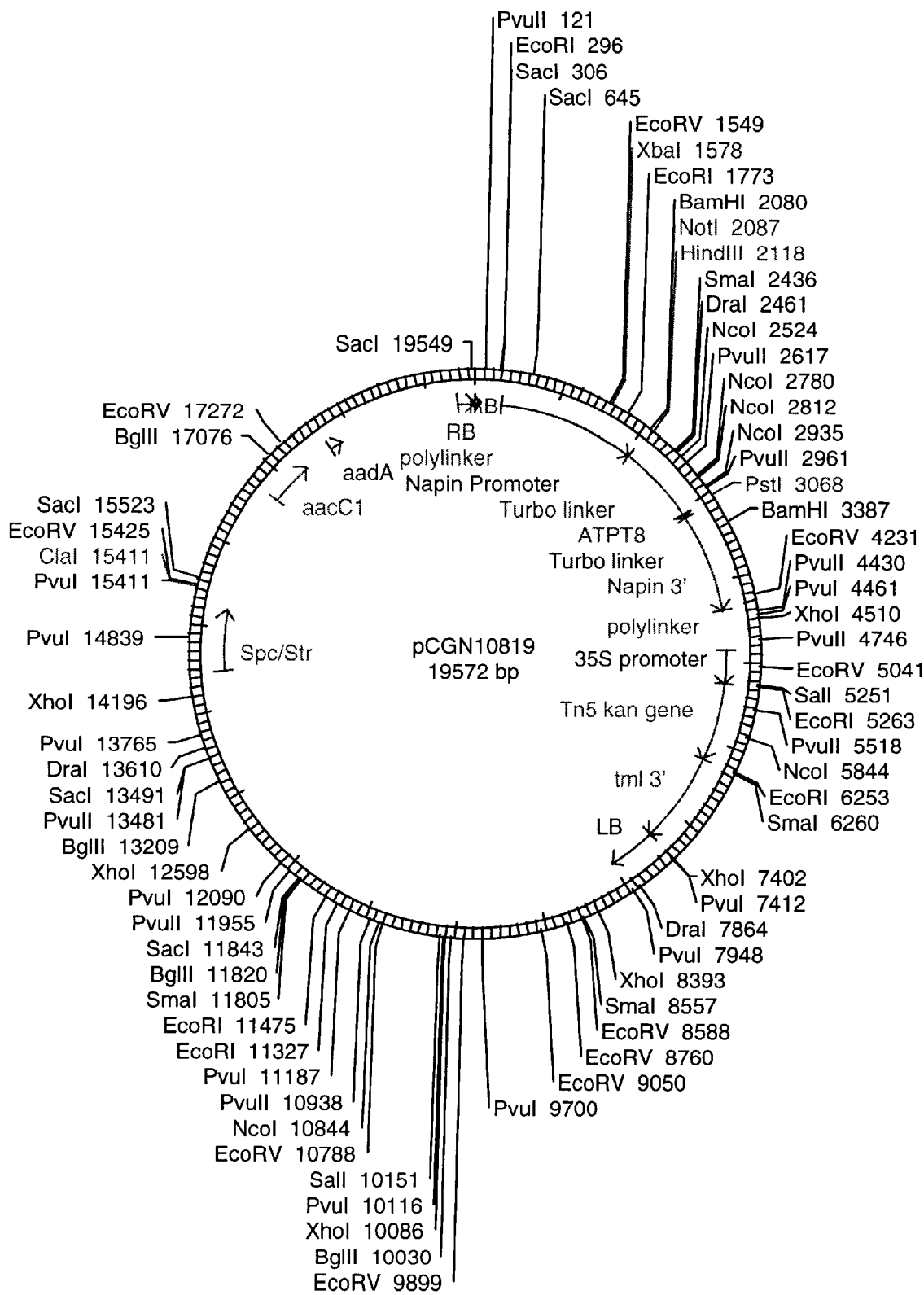
FIG. 17 provides a schematic picture of the expression construct pCGN10819.

The ATPT2 coding sequence (SEQ ID NO: 1) was cloned into the vector pCGN???? to create the plant transformation construct pCGN10817 (FIG. 16). The ATPT8 coding sequence (SEQ ID NO: 11) was cloned in the sense orientation into the vector pCGN8643 to create the plant transformation construct pCGN10819 (FIG. 17).

Figure 18:
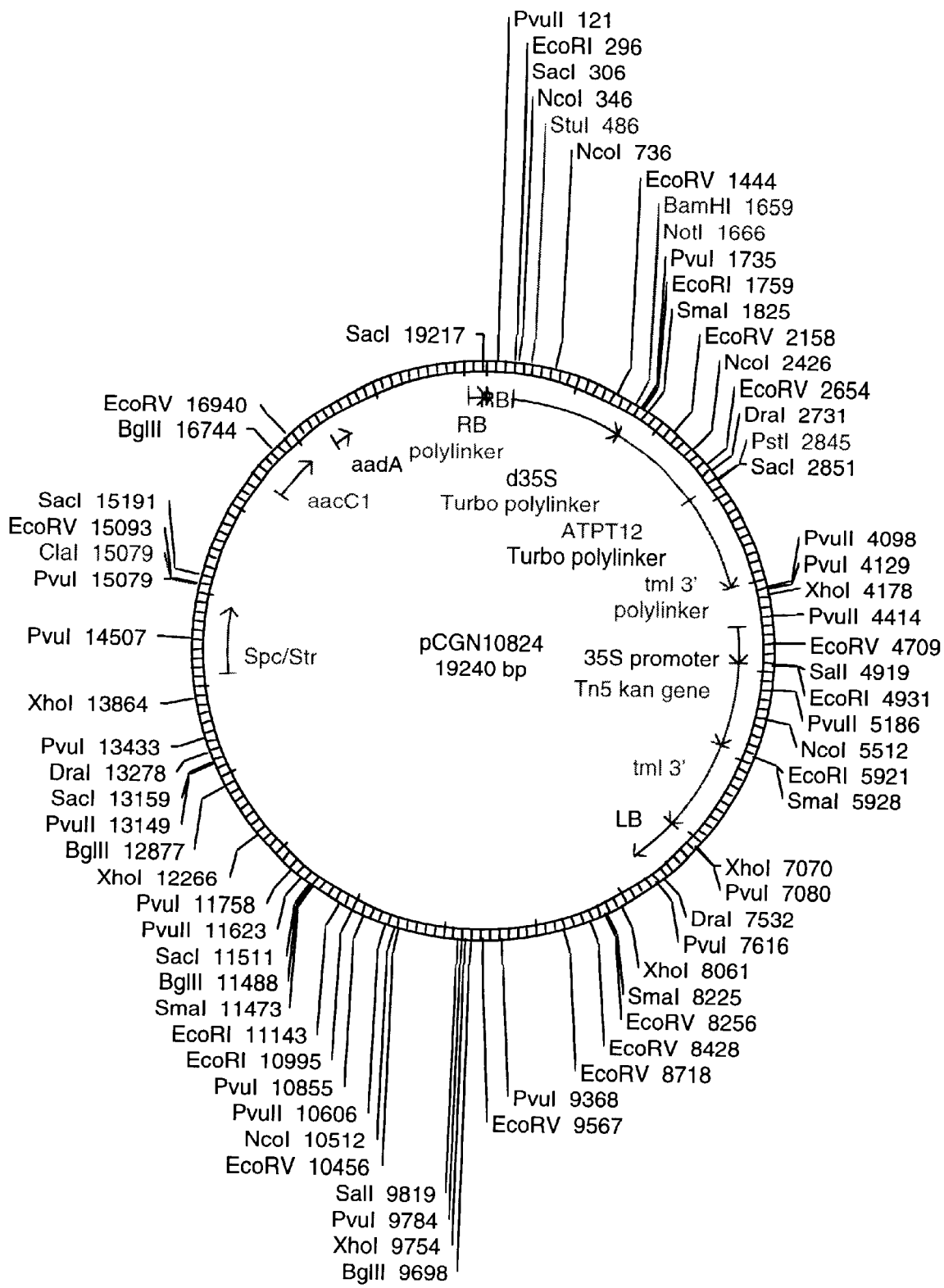
FIG. 18 provides a schematic picture of the expression construct pCGN10824.
Figure 19:
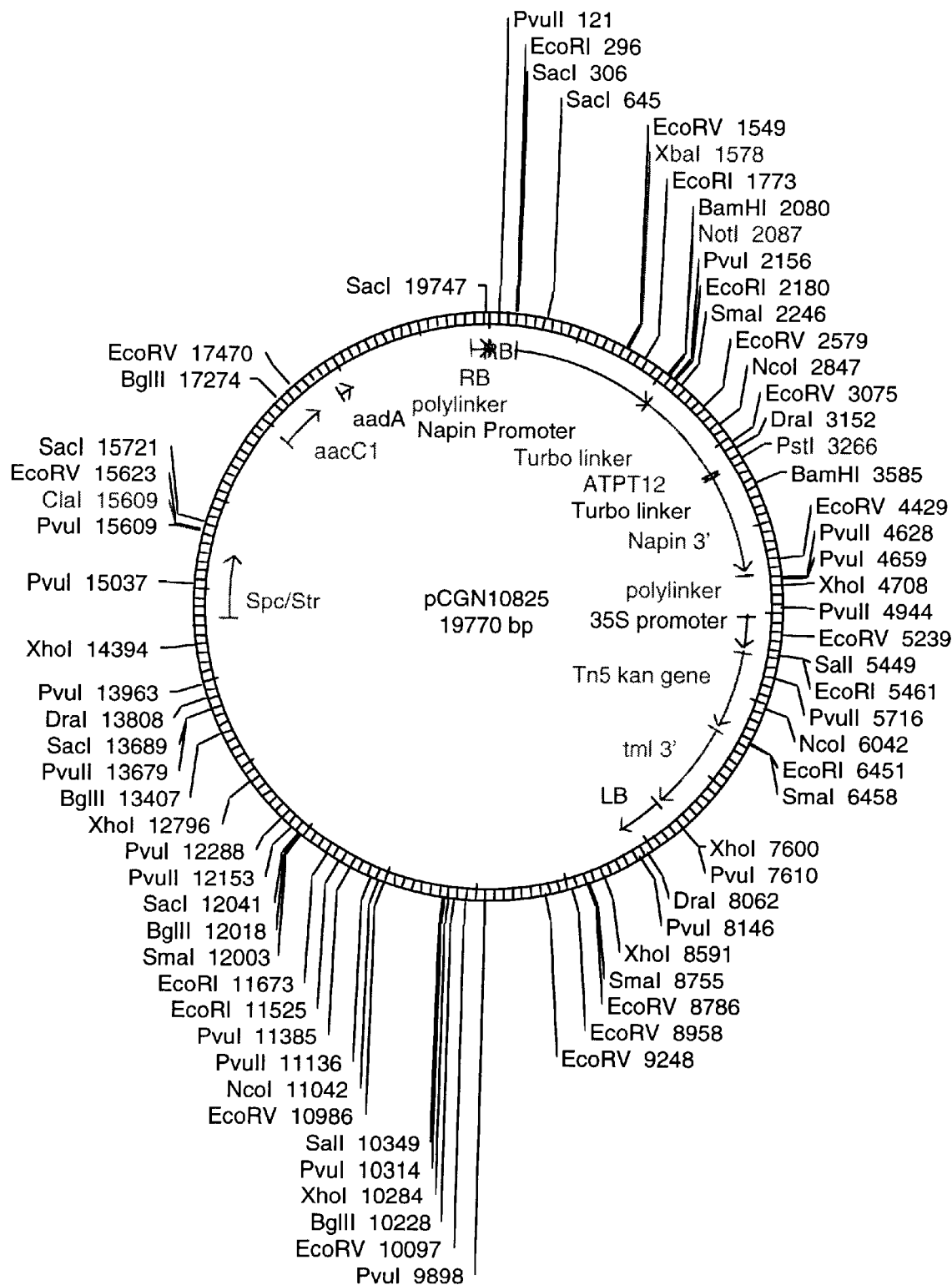
FIG. 19 provides a schematic picture of the expression construct pCGN10825.
Figure 20:
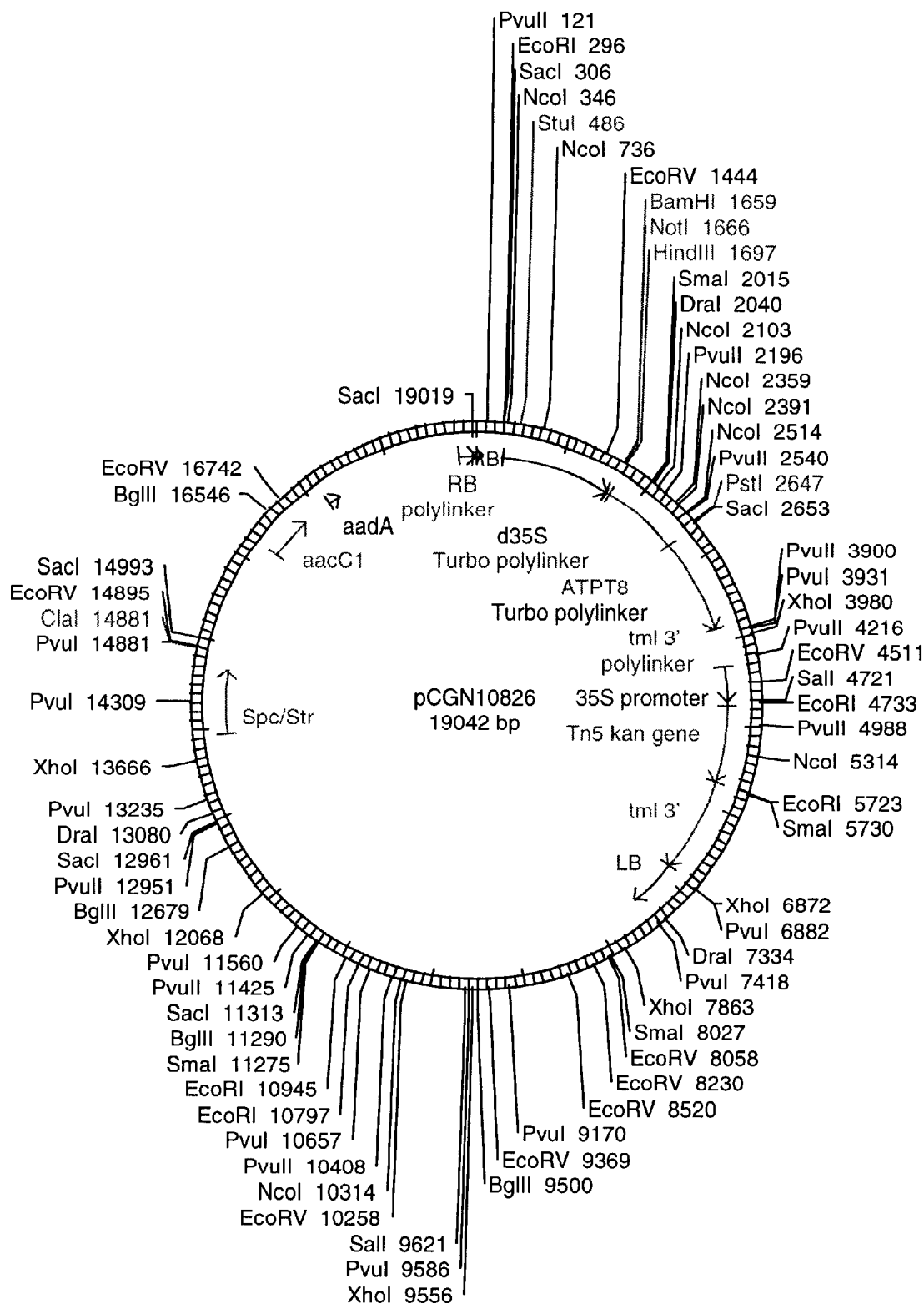
FIG. 20 provides a schematic picture of the expression construct pCGN10826.

The ATPT12 coding sequence (SEQ ID NO: 16) was cloned into the vector pCGN8644 to create the plant transformation construct pCGN10824 (FIG. 18). The ATPT12 coding sequence (SEQ ID NO: 16) was cloned into the vector pCGN8641 to create the plant transformation construct pCGN10825 (FIG. 19). The ATPT8 coding sequence (SEQ ID NO: 11) was cloned into the vector pCGN8644 to create the plant transformation construct pCGN10826 (FIG. 20).

EXAMPLE 3

Plant Transformation

Transgenic Brassica plants are obtained by Agrobacterium-mediated transformation as described by Radke et al. (Theor. Appl. Genet. (1988) 75: 685–694; Plant Cell Reports (1992) 11: 499–505). Transgenic Arabidopsis thaliana plants may be obtained byAgrobacterium-mediated transformation as described by Valverkens et al., (Proc. Nat. Acad. Sci. (1988) 85: 5536–5540), or as described by Bent et al. ((1994), Science 265: 1856–1860), or Bechtold et al. ((1993), C.R.Acad.Sci, Life Sciences 316: 1194–1199). Other plant species may be similarly transformed using related techniques.

Alternatively, microprojectile bombardment methods, such as described by Klein et al. (Bio/Technology 10: 286–291) may also be used to obtain nuclear transformed plants.

EXAMPLE 4

Identification of Additional Prenyltransferases

A PSI-Blast profile generated using the *E. coli* ubiA (genbank accession 1790473) sequence was used to analyze the Synechocystis genome. This analysis identified 5 open reading frames (ORFs) in the Synechocystis genome that were potentially prenyltransferases; slr0926 (annotated as ubiA (4-hydroxybenzoate-octaprenyl transferase, SEQ ID NO: 32), sll1899 (annotated as ctaB (cytocrome c oxidase folding protein, SEQ ID NO: 33), slr0056 (annotated as g4 (chlorophyll synthase 33 kd subunit, SEQ ID NO: 34), slr1518 (annotated as menA (menaquinone biosynthesis protein, SEQ ID NO: 35), and slr1736 (annotated as a hypothetical protein of unknown function (SEQ ID NO: 36).

To determine the functionality of these ORFs and their involvement, if any, in the biosynthesis of Tocopherols, knockouts constructs were made to disrupt the ORF identified in Synechocystis.

Synthetic oligos were designed to amplify regions from the 5' (5'-TAATGTGTACATTGTCGGCCTC (17365') (SEQ ID NO: 61) and 5'-GCAATGTAACATCAGAGATTTTGAGACACAACGT GGCTTTCCACAATTCCCCGCACCGTC (1736kanpr1)) (SEQ ID NO: 62) and 3' (5'-AGGCTAATAAGCACAAATGGGA (17363') (SEQ ID NO: 63) and 5'-GGTATGAGTCAGCAACACCTTCTTCACGAGGCA G ACCTCAGCGGAATTGGTTTAGGTTATCCC (1736kanpr2)) (SEQ ID NO: 64) ends of the slr1736 ORF. The 1736kanpr1 and 1736kanpr2 oligos contained 20 bp of homology to the slr1736 ORF with an additional 40 bp of sequence homology to the ends of the kanamycin resistance cassette. Separate PCR steps were completed with these oligos and the products were gel purified and combined with the kanamycin resistance gene from puc4K (Pharmacia) that had been digested with HincII and gel purified away from the vector backbone. The combined fragments were allowed to assemble without oligos under the following conditions: 94° C. for 1 min, 55° C. for 1 min, 72° C. for 1 min plus 5 seconds per cycle for 40 cycles using pfu polymerase in 100 µl reaction volume (Zhao, H and Arnold (1997) *Nucleic Acids Res.* 25(6): 1307–1308). One microliter or five microliters of this assembly reaction was then amplified using 5' and 3' oligos nested within the ends of the ORF fragment, so that the resulting product contained 100–200 bp of the 5' end of the Synechocystis gene to be knocked out, the kanamycin resistance cassette, and 100–200 bp of the 3' end of the gene to be knocked out. This PCR product was then cloned into the vector pGemT easy (Promega) to create the construct pMON21681 and used for Synechocystis transformation.

Primers were also synthesized for the preparation of Synechocystis knockout constructs for the other sequences using the same method as described above, with the following primers. The ubiA 5' sequence was amplified using the primers 5'-GGATCCATGGTTGCCCAAACCCCATC (SEQ ID NO: 65) and 5'- GCAATGTAACATCA-GAGATTTTGAGACACAACG TGGCTTTGGGTAAG-CAACAATGACCGGC (SEQ ID NO: 66). The 3' region was amplified using the synthetic oligonucleotide primers 5'-GAATTCTCAAAGCCAGCCCAGTAAC (SEQ ID NO: 67) and 5'-GGTATGAGTCAGCAACACCTTCTTCACGAGGCA GACCTCAGCGGGTGCGAAAAGGGTTTTCCC (SEQ ID NO: 68). The amplification products were combined with the kanamycin resistance gene from puc4K (Pharmacia) that had been digested with HincII and gel purified away from the vector backbone. The annealed fragment was amplified using 5' and 3' oligos nested within the ends of the ORF fragment (5'- CCAGTGGTTTAGGCT-GTGTGGTC (SEQ ID NO: 69) and 5'-CTGAGTTGGATGTATTGGATC (SEQ ID NO: 70)), so that the resulting product contained 100–200 bp of the 5' end of the Synechocystis gene to be knocked out, the kanamycin resistance cassette, and 100–200 bp of the 3' end of the gene to be knocked out. This PCR product was then cloned into the vector pGemT easy (Promega) to create the construct pMON21682 and used for Synechocystis transformation.

Primers were also synthesized for the preparation of Synechocystis knockout constructs for the other sequences using the same method as described above, with the following primers. The sll1899 5' sequence was amplified using the primers 5'-GGATCCATGGTTACTTCGACAAAAATCC (SEQ ID NO: 71) and 5'-GCAATGTAACATCAGAGATTTTGAGACACAACGT GGCTTTGCTAGGCAACCGCTTAGTAC (SEQ ID NO: 72). The 3' region was amplified using the synthetic oligonucleotide primers 5'-GAATTCTTAACCCAACAGTAAAGTTCCC (SEQ ID NO: 73) and 5'-GGTATGAGTCAGCAACACCTTCTTCACGAGGCA GACCTCAGCGCCGGCATTGTCTTTTACATG (SEQ ID NO: 74). The amplification products were combined with the kanamycin resistance gene from puc4K (Pharmacia) that had been digested with HincII and gel purified away from the vector backbone. The annealed fragment was amplified using 5' and 3' oligos nested within the ends of the ORF fragment (5'-GGAACCCTTGCAGCCGCTTC (SEQ ID NO: 75) and 5'-GTATGCCCAACTGGTGCAGAGG (SEQ ID NO: 76)), so that the resulting product contained 100–200 bp of the 5' end of the Synechocystis gene to be knocked out, the kanamycin resistance cassette, and 100–200 bp of the 3' end of the gene to be knocked out. This PCR product was then cloned into the vector pGemT easy (Promega) to create the construct pMON21679 and used for Synechocystis transformation.

Primers were also synthesized for the preparation of Synechocystis knockout constructs for the other sequences using the same method as described above, with the following primers. The slr0056 5' sequence was amplified using the primers 5'-GGATCCATGTCTGACACACAAAATACCG (SEQ ID NO: 77) and 5'-GCAATGTAACATCAGAGATTTTGAGACACAACG TGGCTTTCGCCAATACCAGCCACCAACAG (SEQ ID NO: 78). The 3' region was amplified using the synthetic oligonucleotide primers 5'-GAATTCTCAAAT CCCCG-CATGGCCTAG (SEQ ID NO: 79) and 5'-GGTATGAGTCAGCAACACCTTCTTCACGAGGCA GACCTCAGCGGCCTACGGCTTGGACGTGTGGG (SEQ ID NO: 80). The amplification products were combined with the kanamycin resistance gene from puc4K (Pharmacia) that had been digested with HincII and gel purified away from the vector backbone. The annealed fragment was amplified using 5' and 3' oligos nested within the ends of the ORF fragment (5'-CACTTGGATTCCCCTGATCTG (SEQ ID NO: 81) and 5'-GCAATACCCGCTTGGAAAACG (SEQ ID NO: 82)), so that the resulting product contained 100–200 bp of the 5' end of the Synechocystis gene to be knocked out, the kanamycin resistance cassette, and 100–200 bp of the 3' end of the gene to be knocked out. This PCR product was then cloned into the vector pGemT easy (Promega) to create the construct pMON21677 and used for Synechocystis transformation.

Primers were also synthesized for the preparation of Synechocystis knockout constructs for the other sequences using the same method as described above, with the following primers. The slr1518 5' sequence was amplified using the primers 5'-GGATCCATGACCGAATCTTCGCCCCTAGC (SEQ ID NO: 83) and 5'-GCAATGTAACATCAGAGATTTTGAGACACAACGTGGCTTTCAATCCTAGGTAGCCGAGGCG (SEQ ID NO: 84). The 3' region was amplified using the synthetic oligonucleotide primers 5'-GAATTCTTAGCCCAGGCCAGCCCAGCC (SEQ ID NO: 85) and 5'-GGTATGAGTCAGCAACACCTTCTTCACGAGGCAGACCTCAGCGGGGAATTGATTTGTTTAATTACC (SEQ ID NO: 86). The amplification products were combined with the kanamycin resistance gene from puc4K (Pharmacia) that had been digested with HincII and gel purified away from the vector backbone. The annealed fragment was amplified using 5' and 3' oligos nested within the ends of the ORF fragment (5'-GCGATCGCCATTATCGCTTGG (SEQ ID NO: 87) and 5'-GCAGACTGGCAATTATCAGTAACG (SEQ ID NO: 88)), so that the resulting product contained 100–200 bp of the 5' end of the Synechocystis gene to be knocked out, the kanamycin resistance cassette, and 100–200 bp of the 3' end of the gene to be knocked out. This PCR product was then cloned into the vector pGemT easy (Promega) to create the construct pMON21680 and used for Synechocystis transformation.

B. Transformation of Synechocystis

Cells of Synechocystis 6803 were grown to a density of approximately $2 \times 10^8$ cells per ml and harvested by centrifugation. The cell pellet was re-suspended in fresh BG-11 medium (ATCC Medium 616) at a density of $1 \times 10^9$ cells per ml and used immediately for transformation. One-hundred microliters of these cells were mixed with 5 μl of mini prep DNA and incubated with light at 30 C for 4 hours. This mixture was then plated onto nylon filters resting on BG-11 agar supplemented with TES pH8 and allowed to grow for 12–18 hours. The filters were then transferred to BG-11 agar+TES+5 μg/ml kanamycin and allowed to grow until colonies appeared within 7–10 days (Packer and Glazer, 1988). Colonies were then picked into BG-11 liquid media containing 5 μg/ml kanamycin and allowed to grow for 5 days. These cells were then transferred to Bg-11 media containing 10 μg/ml kanamycin and allowed to grow for 5 days and then transferred to Bg-11+kanamycin at 25 μg/ml and allowed to grow for 5 days. Cells were then harvested for PCR analysis to determine the presence of a disrupted ORF and also for HPLC analysis to determine if the disruption had any effect on tocopherol levels.

PCR analysis of the Synechocystis isolates for slr1736 and sll1899 showed complete segregation of the mutant genome, meaning no copies of the wild type genome could be detected in these strains. This suggests that function of the native gene is not essential for cell function. HPLC analysis of these same isolates showed that the sll1899 strain had no detectable reduction in tocopherol levels. However, the strain carrying the knockout for slr1736 produced no detectable levels of tocopherol.

Figure 21:
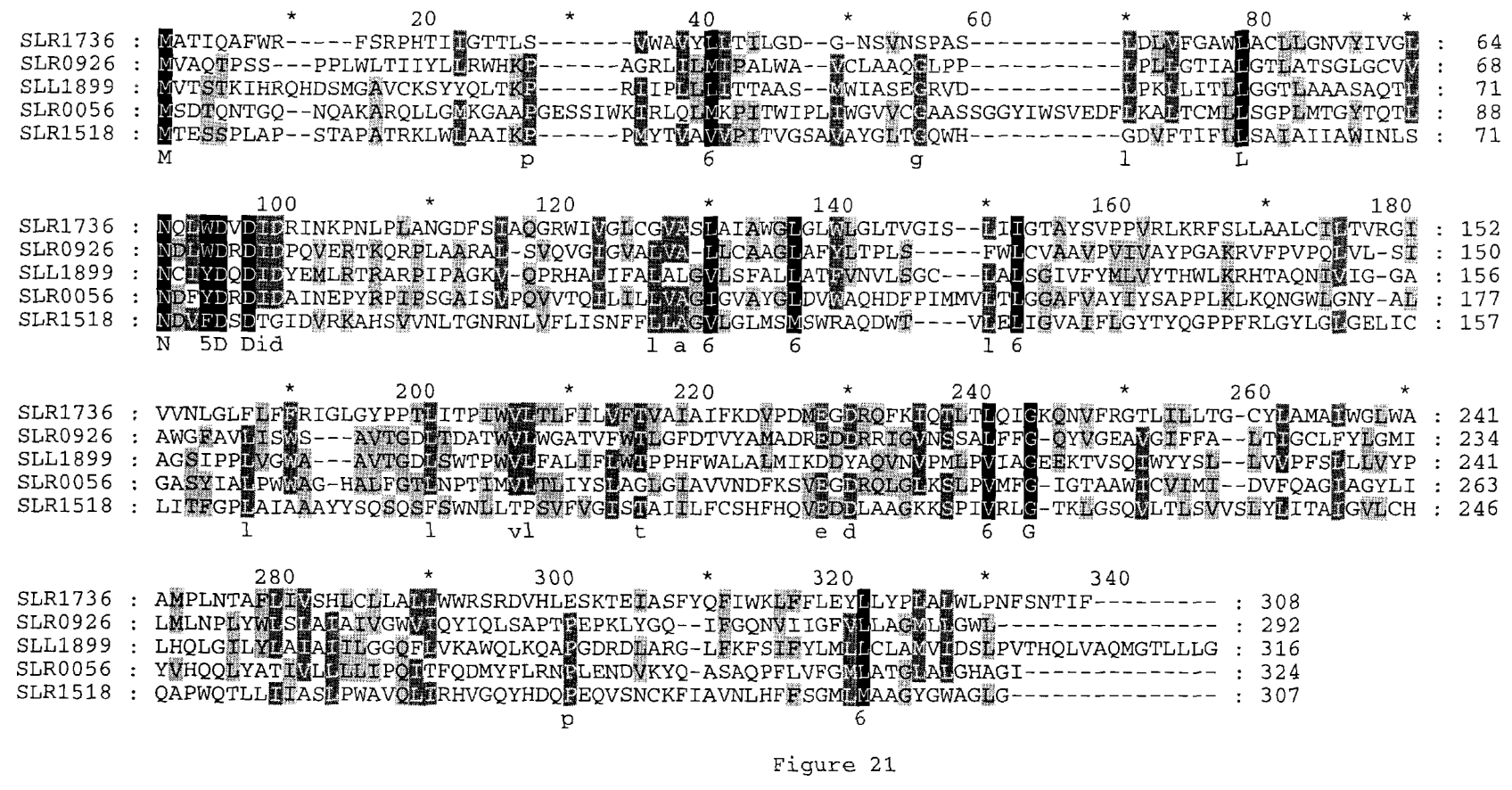

The amino acid sequences for the Synechocystis knockouts slr1736, slr0926, sll1899, slr0056 and slr1518 (SEQ ID NOs: 37, 32, 33, 34 and 35, respectively) are compared using ClustalW, and are provided in Table 3 below. Provided are the percent identities, percent similarity, and the percent gap. The alignment of the sequences is provided in FIG. 21.

TABLE 3

|  |  | Slr1736 | slr0926 | sll1899 | slr0056 | slr1518 |
|---|---|---|---|---|---|---|
| slr1736 | % identity |  | 14 | 12 | 18 | 11 |
|  | % similar |  | 29 | 30 | 34 | 26 |
|  | % gap |  | 8 | 7 | 10 | 5 |
| slr0926 | % identity |  |  | 20 | 19 | 14 |
|  | % similar |  |  | 39 | 32 | 28 |
|  | % gap |  |  | 7 | 9 | 4 |
| sll1899 | % identity |  |  |  | 17 | 13 |
|  | % similar |  |  |  | 29 | 29 |
|  | % gap |  |  |  | 12 | 9 |
| slr0056 | % identity |  |  |  |  | 15 |
|  | % similar |  |  |  |  | 31 |
|  | % gap |  |  |  |  | 8 |
| slr1518 | % identity |  |  |  |  |  |
|  | % similar |  |  |  |  |  |
|  | % gap |  |  |  |  |  |

Figure 22:
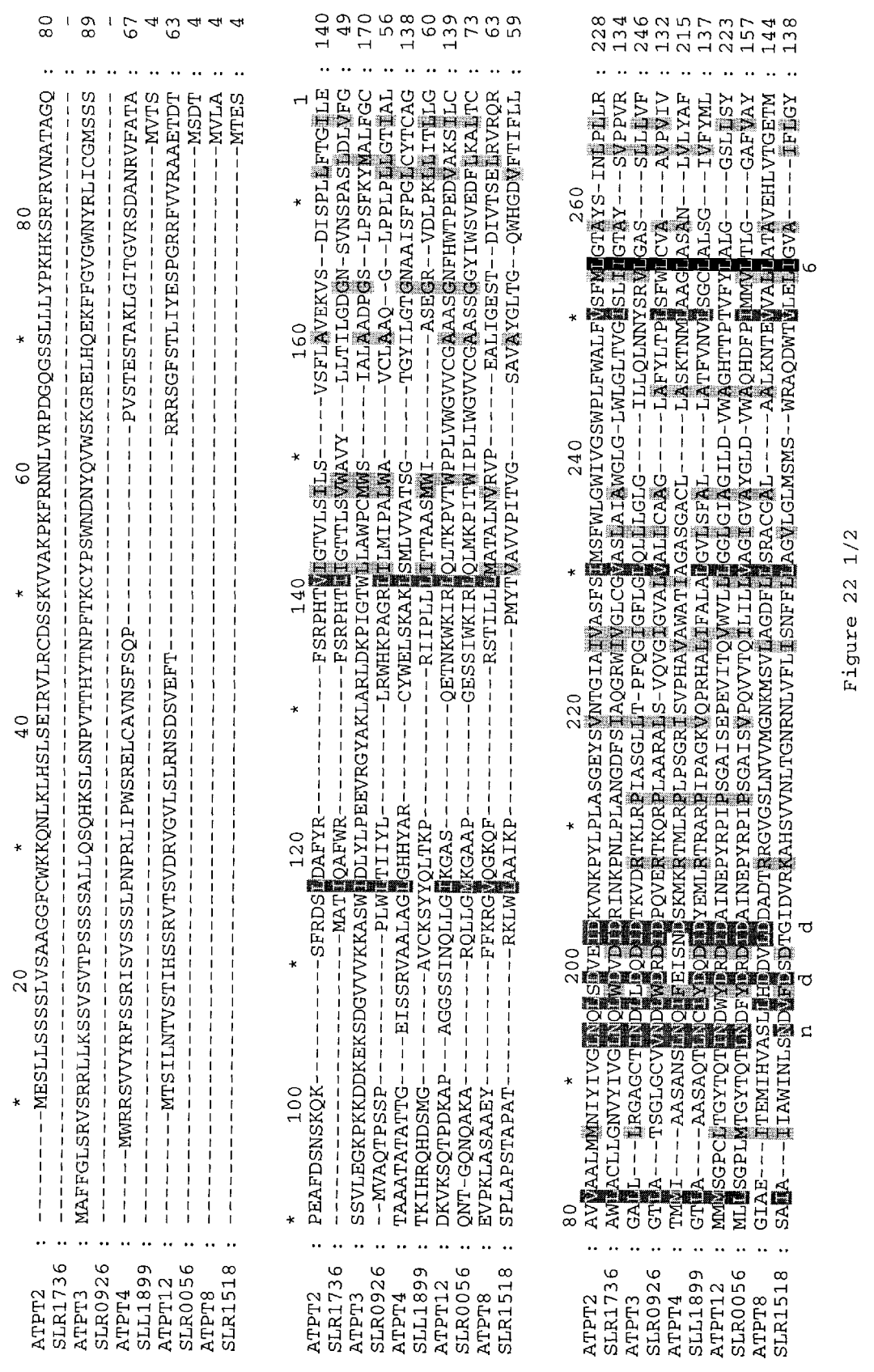

Amino acid sequence comparisons are performed using various Arabidopsis prenyltransferase sequences (ATPT2 (SEQ ID NO: 2), ATPT3 (SEQ ID NO: 4), ATPT4 (SEQ ID NO: 6), ATPT8 (SEQ ID NO: 12) and ATPT12 (SEQ ID NO: 17)) and the Synechocystis sequences (slr1736 (SEQ ID NO: 37), slr0926 (SEQ ID NO: 32), sll1899 (SEQ ID NO: 33), slr0056 (SEQ ID NO: 34), and slr1518 (SEQ ID NO: 35)). The comparisons are presented in Table 4 below. Provided are the percent identities, percent similarity, and the percent gap. The alignment of the sequences is provided in FIG. 22.

TABLE 4

|  | ATPT2 | slr1736 | ATPT3 | slr0926 | ATPT4 | sll1899 | ATPT12 | slr0056 | ATPT8 | slr1518 |
|---|---|---|---|---|---|---|---|---|---|---|
| ATPT2 |  | 29 | 9 | 9 | 8 | 8 | 12 | 9 | 7 | 9 |
|  |  | 46 | 23 | 21 | 20 | 20 | 28 | 23 | 21 | 20 |
|  |  | 27 | 13 | 28 | 23 | 29 | 11 | 24 | 25 | 24 |
| slr1736 |  |  | 9 | 13 | 8 | 12 | 13 | 15 | 8 | 10 |
|  |  |  | 19 | 28 | 19 | 28 | 26 | 33 | 21 | 26 |
|  |  |  | 34 | 12 | 34 | 15 | 26 | 10 | 12 | 10 |
| ATPT3 |  |  |  | 23 | 11 | 14 | 13 | 10 | 5 | 11 |
|  |  |  |  | 36 | 26 | 26 | 26 | 21 | 14 | 22 |
|  |  |  |  | 29 | 21 | 31 | 16 | 30 | 30 | 30 |
|  |  |  |  |  | 12 | 20 | 17 | 20 | 11 | 14 |
| slr0926 |  |  |  |  | 24 | 37 | 28 | 33 | 24 | 29 |
|  |  |  |  |  | 33 | 12 | 25 | 10 | 11 | 9 |
|  |  |  |  |  |  | 18 | 11 | 8 | 6 | 7 |
| ATPT4 |  |  |  |  |  | 33 | 23 | 18 | 16 | 19 |
|  |  |  |  |  |  | 28 | 19 | 32 | 32 | 33 |

TABLE 4-continued

| | ATPT2 | slr1736 | ATPT3 | slr0926 | ATPT4 | sll1899 | ATPT12 | slr0056 | ATPT8 | slr1518 |
|---|---|---|---|---|---|---|---|---|---|---|
| | | | | | | | 13 | 17 | 10 | 12 |
| sll1899 | | | | | | | 24 | 30 | 23 | 26 |
| | | | | | | | 27 | 13 | 10 | 11 |
| | | | | | | | | 52 | 8 | 11 |
| ATPT12 | | | | | | | | 66 | 19 | 26 |
| | | | | | | | | 18 | 25 | 23 |
| | | | | | | | | | 9 | 13 |
| slr0056 | | | | | | | | | 23 | 32 |
| | | | | | | | | | 10 | 8 |
| | | | | | | | | | | 7 |
| ATPT8 | | | | | | | | | | 23 |
| | | | | | | | | | | 7 |
| slr1518 | | | | | | | | | | |

4B. Preparation of the slr1737 Knockout

The Synechocystis sp. 6803 slr1737 knockout was constructed by the following method. The GPS™-1 Genome Priming System (New England Biolabs) was used to insert, by a Tn7 Transposase system, a Kanamycin resistance cassette into slr1737. A plasmid from a Synechocystis genomic library clone containing 652 base pairs of the targeted orf (Synechcocystis genome base pairs 1324051–1324703; the predicted orf base pairs 1323672–1324763, as annotated by Cyanobase) was used as target DNA. The reaction was performed according to the manufacturers protocol. The reaction mixture was then transformed into E. coli DH10B electrocompetant cells and plated. Colonies from this transformation were then screened for transposon insertions into the target sequence by amplifying with M13 Forward and Reverse Universal primers, yielding a product of 652 base pairs plus ~1700 base pairs, the size of the transposon kanamycin cassette, for a total fragment size of ~2300 base pairs. After this determination, it was then necessary to determine the approximate location of the insertion within the targeted orf, as 100 base pairs of orf sequence was estimated as necessary for efficient homologous recombination in Synechocystis. This was accomplished through amplification reactions using either of the primers to the ends of the transposon, Primer S (5' end) or N (3' end), in combination with either a M13 Forward or Reverse primer. That is, four different primer combinations were used to map each potential knockout construct: Primer S - M13 Forward, Primer S - M13 Reverse, Primer N - M13 Forward, Primer N - M13 Reverse. The construct used to transform Synechocystis and knockout slr1737 was determined to consist of a approximately 150 base pairs of slr1737 sequence on the 5' side of the transposon insertion and approximately 500 base pairs on the 3' side, with the transcription of the orf and kanamycin cassette in the same direction. The nucleic acid sequence of slr1737 is provided in SEQ ID NO: 38 the deduced amino acid sequence is provided in SEQ ID NO: 39.

Cells of Synechocystis 6803 were grown to a density of ~2x10$^8$ cells per ml and harvested by centrifugation. The cell pellet was re-suspended in fresh BG-11 medium at a density of 1x10$^9$ cells per ml and used immediately for transformation. 100 ul of these cells were mixed with 5 ul of mini prep DNA and incubated with light at 30 C for 4 hours. This mixture was then plated onto nylon filters resting on BG-11 agar supplemented with TES ph8 and allowed to grow for 12–18 hours. The filters were then transferred to BG-11 agar+TES+5 ug/ml kanamycin and allowed to grow until colonies appeared within 7–10 days (Packer and Glazer, 1988). Colonies were then picked into BG-11 liquid media containing 5 ug/ml kanamycin and allowed to grow for 5 days. These cells were then transferred to Bg-11 media containing 10 ug/ml kanamycin and allowed to grow for 5 days and then transferred to Bg-11+kanamycin at 25 ug/ml and allowed to grow for 5 days. Cells were then harvested for PCR analysis to determine the presence of a disrupted ORF and also for HPLC analysis to determine if the disruption had any effect on tocopherol levels.

PCR analysis of the Synechocystis isolates, using primers to the ends of the slr1737 orf, showed complete segregation of the mutant genome, meaning no copies of the wild type genome could be detected in these strains. This suggests that function of the native gene is not essential for cell function. HPLC analysis of the strain carrying the knockout for slr1737 produced no detectable levels of tocopherol.

4C. Phytyl Prenyltransferase Enzyme Assays

[$^3$H] Homogentisic acid in 0.1% $H_3PO_4$ (specific radioactivity 40 Ci/mmol). Phytyl pyrophosphate was synthesized as described by Joo, et al. (1973) Can J. Biochem. 51: 1527. 2-methyl-6-phytylquinol and 2,3-dimethyl-5-phytylquinol were synthesized as described bySoll, et al. (1980) Phytochemistry 19: 215. Homogentisic acid, α, β, δ, and γ-tocopherol, and tocol, were purchased commercially.

The wild-type strain of Synechocystis sp. PCC 6803 was grown in BG11 medium with bubbling air at 30° C. under 50 $\mu$E.m$^{-2}$.s$^{-1}$ fluorescent light, and 70% relative humidity. The growth medium of slr1736 knock-out (potential PPT) strain of this organism was supplemented with 25 $\mu$mL$^{-1}$ kanamycin. Cells were collected from 0.25 to 1 liter culture by centrifugation at 5000 g for 10 min and stored at −80° C.

Total membranes were isolated according to Zak's procedures with some modifications (Zak, et al. (1999) Eur J. Biochem 261: 311). Cells were broken on a French press. Before the French press treatment, the cells were incubated for 1 hour with lysozyme (0.5%, w/v) at 30° C. in a medium containing 7 mM EDTA, 5 mM NaCl and 10 mM Hepes-NaOH, pH 7.4. The spheroplasts were collected by centrifugation at 5000 g for 10 min and resuspended at 0.1–0.5 mg chlorophyll·mL$^{-1}$ in 20 mM potassium phosphate buffer, pH 7.8. Proper amount of protease inhibitor cocktail and DNAase I from Boehringer Mannheim were added to the solution. French press treatments were performed two to three times at 100 MPa. After breakage, the cell suspension was centrifuged for 10 min at 5000 g to pellet unbroken cells, and this was followed by centrifugation at 100 000 g for 1 hour to collect total membranes. The final pellet was resuspended in a buffer containing 50 mM Tris-HCL and 4 mM $MgCl_2$.

Chloroplast pellets were isolated from 250 g of spinach leaves obtained from local markets. Devined leaf sections were cut into grinding buffer (2 1/250 g leaves) containing 2 mM EDTA, 1 mM MgCl$_2$, 1 mM MnCl$_2$, 0.33 M sorbitol, 0.1% ascorbic acid, and 50 mM Hepes at pH 7.5. The leaves were homogenized for 3 sec three times in a 1-L blendor, and filtered through 4 layers of mirocloth. The supernatant was then centrifuged at 5000 g for 6 min. The chloroplast pellets were resuspended in small amount of grinding buffer (Douce,et al Methods in Chloroplast Molecular Biology, 239 (1982)

Chloroplasts in pellets can be broken in three ways. Chloroplast pellets were first aliquoted in 1 mg of chlorophyll per tube, centrifuged at 6000 rpm for 2 min in microcentrifuge, and grinding buffer was removed. Two hundred microliters of Triton X-100 buffer (0.1% Triton X-100, 50 mM Tris-HCl pH 7.6 and 4 mM MgCl$_2$) or swelling buffer (10 mM Tris pH 7.6 and 4 mM MgCl$_2$) was added to each tube and incubated for 1/2 hour at 4° C. Then the broken chloroplast pellets were used for the assay immediately. In addition, broken chloroplasts can also be obtained by freezing in liquid nitrogen and stored at –80° C. for 1/2 hour, then used for the assay.

In some cases chloroplast pellets were further purified with 40%/80% percoll gradient to obtain intact chloroplasts. The intact chloroplasts were broken with swelling buffer, then either used for assay or further purified for envelope membranes with 20.5%/31.8% sucrose density gradient (Sol, et al (1980) supra). The membrane fractions were centrifuged at 100 000 g for 40 min and resuspended in 50 mM Tris-HCl pH 7.6, 4 mM MgCl$_2$.

Various amounts of [$^3$H]HGA, 40 to 60 $\mu$M unlabelled HGA with specific activity in the range of 0.16 to 4 Ci/mmole were mixed with a proper amount of 1 M Tris-NaOH pH 10 to adjust pH to 7.6. HGA was reduced for 4 min with a trace amount of solid NaBH$_4$. In addition to HGA, standard incubation mixture (final vol 1 mL) contained 50 mM Tris-HCl, pH 7.6, 3–5 mM MgCl$_2$, and 100 $\mu$M phytyl pyrophosphate. The reaction was initiated by addition of Synechocystis total membranes, spinach chloroplast pellets, spinach broken chloroplasts, or spinach envelope membranes. The enzyme reaction was carried out for 2 hour at 23° C. or 30° C. in the dark or light. The reaction is stopped by freezing with liquid nitrogen, and stored at –80° C. or directly by extraction.

A constant amount of tocol was added to each assay mixture and reaction products were extracted with a 2 mL mixture of chloroform/methanol (1:2, v/v) to give a monophasic solution. NaCl solution (2 mL; 0.9%) was added with vigorous shaking. This extraction procedure was repeated three times. The organic layer containing the prenylquinones was filtered through a 20 m $\mu$ filter, evaporated under N$_2$, and then resuspended in 100 $\mu$L of ethanol.

The samples were mainly analyzed by Normal-Phase HPLC method (Isocratic 90% Hexane and 10% Methyl-t-butyl ether), and use aZorbax silica column, 4.6×250 mm. The samples were also analyzed by Reversed-Phase HPLC method (Isocratic 0.1% H$_3$PO$_4$ in MeOH), and use a Vydac 201HS54 C18 column; 4.6×250 mm coupled with an Alltech C18 guard column. The amount of products were calculated based on the substrate specific radioactivity, and adjusted according to the % recovery based on the amount of internal standard.

The amount of chlorophyll was determined as described in Arnon (1949) *Plant Physiol.* 24: 1. Amount of protein was determined by the Bradford method using gamma globulin as a standard (Bradford, (1976) *Anal. Biochem.* 72: 248)

Figure 23:
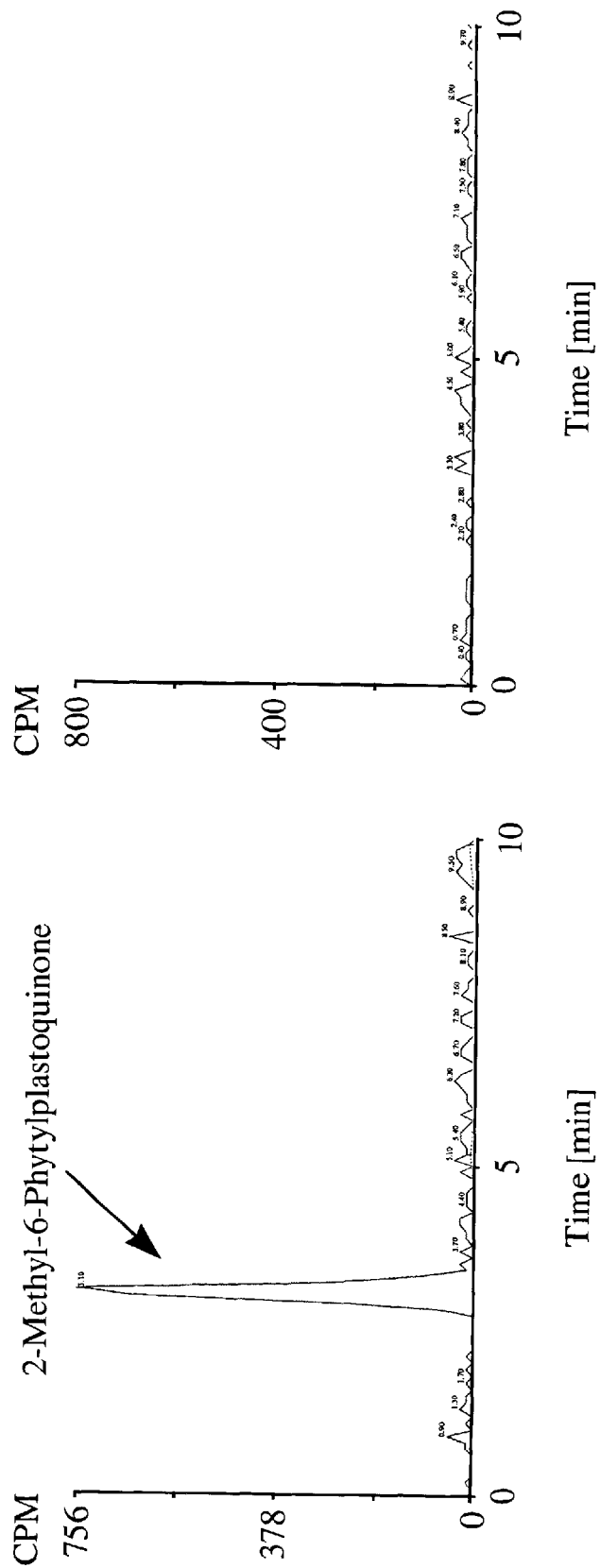
FIG. 23 provides the results of the enzymatic assay from preparations of wild type Synechocystis strain 6803, and Synechocystis slr1736 knockout.

Results of the assay demonstrate that 2-Methyl-6-Phytylplastoquinone is produced in the Synechocystis slr1736 knockout preparations. The results of the phytyl prenyltransferase enzyme activity assay for the slr1736 knock out are presented in FIG. 23.

4D. Complementation of the slr1736 knockout with ATPT2

In order to determine whether ATPT2 could complement the knockout of slr1736 in Synechocystis 6803 a plasmid was constructed to express the ATPT2 sequence from the TAC promoter. A vector, plasmid psl1211, was obtained from the lab of Dr. Himadri Pakrasi of Washington University, and is based on the plasmid RSF1010 which is a broad host range plasmid (Ng W.-O., Zentella R., Wang, Y., Taylor J-S. A., Pakrasi, H. B. 2000. phrA, the major photoreactivating factor in the cyanobacterium Synechocystis sp. strain PCC 6803 codes for a cyclobutane pyrimidine dimer specific DNA photolyase. *Arch. Microbiol.* (in press)). The ATPT2 gene was isolated from the vector pCGN10817 by PCR using the following primers. ATPT2nco.pr 5'-CCATGGATTCGAGTAAAGTTGTCGC (SEQ ID NO: 89); ATPT2ri.pr-5'-GAATTCACTTCAAAAAAGGTAACAG (SEQ ID NO: 90). These primers will remove approximately 112 BP from the 5' end of the ATPT2 sequence, which is thought to be the chloroplast transit peptide. These primers will also add an NcoI site at the 5' end and an EcoRI site at the 3' end which can be used for sub-cloning into subsequent vectors. The PCR product from using these primers and pCGN10817 was ligated into pGEM T easy and the resulting vector pMON21689 was confirmed by sequencing using the m13forward and m13reverse primers. The NcoI/EcoRI fragment from pMON21689 was then ligated with the EagI/EcoRI and EagI/NcoI fragments from psl1211 resulting in pMON21690. The plasmid pMON21690 was introduced into the slr1736 Synechocystis 6803 KO strain via conjugation. Cells of sl906 (a helper strain) and DH10B cells containing pMON21690 were grown to log phase (O.D. 600=0.4) and 1 ml was harvested by centrifugation. The cell pellets were washed twice with a sterile BG-11 solution and resuspended in 200 ul of BG-11. The following was mixed in a sterile eppendorf tube: 50 ul SL906, 50 ul DH10B cells containing pMON21690, and 100 ul of a fresh culture of the slr1736 Synechocystis 6803 KO strain (O.D. 730=0.2–0.4). The cell mixture was immnediately transferred to a nitrocellulose filter resting on BG-11 and incubated for 24 hours at 30 C and 2500 LUX(50 ue) of light. The filter was then transferred to BG-11 supplemented with 10 ug/ml Gentamycin and incubated as above for –5 days. When colonies appeared, they were picked and grown up in liquid BG-11+ Gentamycin 10 ug/ml. (Elhai, J. and Wolk, P. 1988. Conjugal transfer of DNA to Cyanobacteria. *Methods in Enzymology* 167, 747–54) The liquid cultures were then assayed for tocopherols by harvesting 1 ml of culture by centrifugation, extracting with ethanol/pyrogallol, and HPLC separation. The slr1736 Synechocystis 6803 KO strain, did not contain any detectable tocopherols, while the slr1736 Synechocystis 6803 KO strain transformed with pmon21690 contained detectable alpha tocopherol. A Synechocystis 6803 strain transformed with psl1211 (vector control) produced alpha tocopherol as well.

EXAMPLE 5

Transgenic Plant Analysis

Arabidopsis plants transformed with constructs for the sense or antisense expression of the ATPT proteins were analyzed by High Pressure Liquid Chromatography (HPLC) for altered levels of total tocopherols, as well as altered levels of specific tocopherols (alpha, beta, gamma, and delta tocopherol).

Extracts of leaves and seeds were prepared for HPLC as follows. For seed extracts, 10 mg of seed was added to 1 g of microbeads (Biospec) in a sterile microfuge tube to which 500 ul 1% pyrogallol (Sigma Chem)/ethanol was added. The mixture was shaken for 3 minutes in a mini Beadbeater (Biospec) on "fast" speed. The extract was filtered through a 0.2 um filter into an autosampler tube. The filtered extracts were then used in HPLC analysis described below.

Leaf extracts were prepared by mixing 30–50 mg of leaf tissue with 1 g microbeads and freezing in liquid nitrogen until extraction. For extraction, 500 ul 1% pyrogallol in ethanol was added to the leaf/bead mixture and shaken for 1 minute on a Beadbeater (Biospec) on "fast" speed. The resulting mixture was centrifuged for 4 minutes at 14,000 rpm and filtered as described above prior to HPLC analysis.

HPLC was performed on a Zorbax silica HPLC column (4.6 mm×250 mm) with a fluorescent detection, an excitation at 290 nm, an emission at 336 nm, and bandpass and slits. Solvent A was hexane and solvent B was methyl-t-butyl ether. The injection volume was 20 ul, the flow rate was 1.5 ml/min, the run time was 12 min (40° C.) using the gradient (Table 5):

TABLE 5

| Time    | Solvent A | Solvent B |
|---------|-----------|-----------|
| 0 min.  | 90%       | 10%       |
| 10 min. | 90%       | 10%       |
| 11 min. | 25%       | 75%       |
| 12 min. | 90%       | 10%       |

Tocopherol standards in 1% pyrogallol/ethanol were also run for comparison (alpha tocopherol, gamma tocopherol, beta tocopherol, delta tocopherol, and tocopherol (tocol) (all from Matreya).

Standard curves for alpha, beta, delta, and gamma tocopherol were calculated using Chemstation software. The absolute amount of component x is: Absolute amount of x=Response$_x$×RF$_x$×dilution factor where Response$_x$ is the area of peak x, RF$_x$ is the response factor for component x (Amount$_x$/Response$_x$) and the dilution factor is 500 ul. The ng/mg tissue is found by: total ng component/mg plant tissue.

Figure 24:
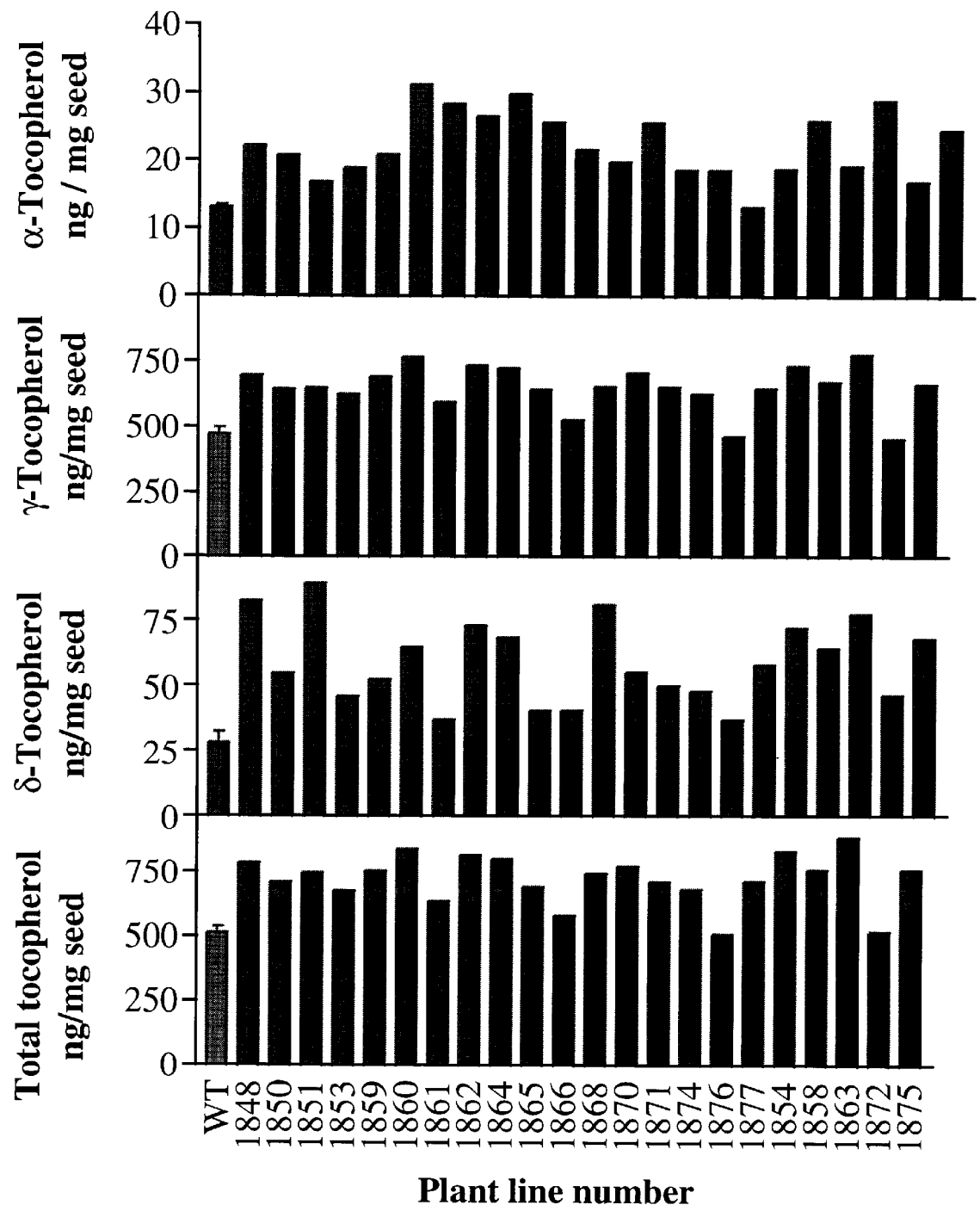
FIG. 24 provides bar graphs of HPLC data obtained from seed extracts of transgenic Arabidopsis containing pCGN10822, which provides of the expression of the ATPT2 sequence, in the sense orientation, from the napin promoter. Provided are graphs for alpha, gamma, and delta tocopherols, as well as total tocopherol for 22 transformed lines, as well as a nontransformed (wildtype) control.

Results of the HPLC analysis of seed extracts of transgenic Arabidopsis lines containing pMON10822 for the expression of ATPT2 from the napin promoter are provided in FIG. 24.

HPLC analysis results of Arabidopsis seed tissue expressing the ATPT2 sequence from the napin promoter (pMON10822) demonstrates an increased level of tocopherols in the seed. Total tocopherol levels are increased as much as 50 to 60% over the total tocopherol levels of non-transformed (wild-type) Arabidopsis plants (FIG. 24).

Furthermnore, increases of particular tocopherols are also increased in transgenic Arabidopsis plants expressing the ATPT2 nucleic acid sequence from the napin promoter. Levels of delta tocopherol in these lines are increased greater than 3 fold over the delta tocopherol levels obtained from the seeds of wild type Arabidopsis lines. Levels of gamma tocopherol in transgenic Arabidopsis lines expressing the ATPT2 nucleic acid sequence are increased as much as about 60% over the levels obtained in the seeds of non-transgenic control lines. Furthermore, levels of alpha tocopherol are increased as much a 3 fold over those obtained from non-transgenic control lines.

Figure 25:
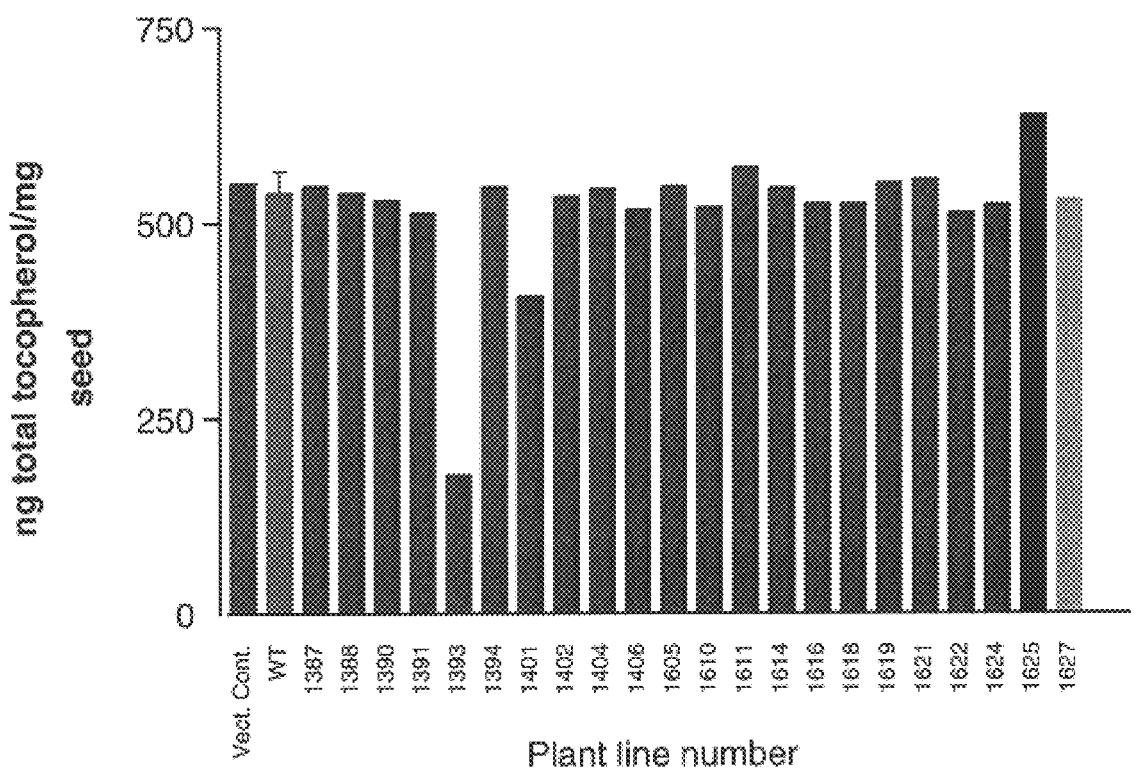
FIG. 25 provides a bar graph of HPLC analysis of seed extracts from Arabidopsis plants transformed with pCGN10803 (35S-ATPT2, in the antisense orientation), pCGN10802 (line 1625, napin ATPT2 in the sense orientation), pCGN10809 (line 1627, 35S-ATPT3 in the sense orientation), a nontransformed (wt) control, and an empty vector transformed control.

Results of the HPLC analysis of seed extracts of transgenic Arabidopsis lines containing pMON10803 for the expression of ATPT2 from the enhanced 35S promoter are provided in FIG. 25.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. An isolated nucleic acid sequence encoding a prenyltransferase wherein said nucleic acid sequence comprises SEQ ID NO: 1.

2. A nucleic acid construct comprising as operably linked components, a transcriptional initiation region functional in a host cell, a nucleic acid sequence encoding a prenyltransferase, wherein said nucleic acid sequence comprises SEQ ID NO: 1, and a transcriptional termination region.

3. A plant cell comprising a nucleic acid construct that comprises as operably linked components, a transcriptional initiation region functional in a host cell, a nucleic acid sequence encoding a prenyltransferase, wherein said nucleic acid sequence comprises SEQ ID NO: 1, and a transcriptional termination region.

4. A method for increasing the tocopherol content in a host cell, comprising transforming said host cell with a construct comprising as operably linked components, a transcriptional initiation region fuinctional in a host cell, a nucleic acid sequence comprising SEQ ID NO: 1, and a transcriptional termination region.

5. The method according to claim 4, wherein said host cell is selected from the group consisting of a prokaryotic cell and a eukaryotic cell.

6. The method according to claim 5, wherein said prokaryotic cell is Synechocystis.

7. The method according to claim 5, wherein said eukaryotic cell is a plant cell.

8. The method according to claim 7, wherein said plant cell is obtained from a plant selected from the group consisting of Arabidopsis, soybean, and corn.

9. A method for producing a tocopherol compound in a host cell, said method comprising obtaining a transformed host cell, said host cell having and expressing in its genome:
   a construct having a nucleic acid sequence comprising SEQ ID NO: 1 operably linked to a transcriptional initiation region functional in a host cell.

10. The method according to claim 9, wherein said host cell is selected from the group consisting of a prokaryotic cell and a eukaryotic cell.

11. The method according to claim 10, wherein said prokaryotic cell is Synechocystis.

12. The method according to claim 9, wherein said eukaryotic cell is a plant cell.

13. The method according to claim 12, wherein said plant cell is obtained from a plant selected from the group consisting of Arabidopsis, soybean, and corn.

14. The method according to claim 7, wherein said plant cell is obtained from a plant selected from the group consisting of Arabidopsis, Canola rapeseed, high erucic acid rapeseed, sunflower, safflower, cotton, soybean, peanut, coconut, oil palms, and corn.

15. The method according to claim 12, wherein said plant cell is obtained from a plant selected from the group consisting of Arabidopsis, Canola rapeseed, high erucic acid rapeseed, sunflower, safflower, cotton, soybean, peanut, coconut, oil palms, and corn.

* * * * *

SEQUENCE LISTING

```
<160> NUMBER OF SEQ ID NOS:  94

<210> SEQ ID NO 1
<211> LENGTH: 1182
<212> TYPE: DNA
<213> ORGANISM: Arabidopsis sp

<400> SEQUENCE: 1
atggagtctc tgctctctag ttcttctctt gtttccgctg ctggtgggtt ttgttggaag      60
aagcagaatc taaagctcca ctctttatca gaaatccgag ttctgcgttg tgattcgagt     120
aaagttgtcg caaaaccgaa gtttaggaac aatcttgtta ggcctgatgg tcaaggatct     180
tcattgttgt tgtatccaaa acataagtcg agatttcggg ttaatgccac tgcgggtcag     240
cctgaggctt tcgactcgaa tagcaaacag aagtcttttta gagactcgtt agatgcgttt     300
tacaggtttt ctaggcctca tacagttatt ggcacagtgc ttagcatttt atctgtatct     360
```

-continued

```
ttcttagcag tagagaaggt ttctgatata tctcctttac ttttcactgg catcttggag    420
gctgttgttg cagctctcat gatgaacatt tacatagttg gctaaatca gttgtctgat    480 gttgaaatag ataaggttaa caagccctat cttccattgg catcaggaga atattctgtt    540
aacaccggca ttgcaatagt agcttccttc tccatcatga gtttctggct tgggtggatt    600
gttggttcat ggccattgtt ctgggctctt tttgtgagtt tcatgctcgg tactgcatac    660
tctatcaatt tgccactttt acggtggaaa agatttgcat tggttgcagc aatgtgtatc    720
ctcgctgtcc gagctattat tgttcaaatc gccttttatc tacatattca gacacatgtg    780
tttggaagac caatcttgtt cactaggcct cttattttcg ccactgcgtt tatgagcttt    840
ttctctgtcg ttattgcatt gtttaaggat atacctgata tcgaagggga taagatattc    900
ggaatccgat cattctctgt aactctgggt cagaaacggg tgttttggac atgtgttaca    960
ctacttcaaa tggcttacgc tgttgcaatt ctagttggag ccacatctcc attcatatgg   1020
agcaaagtca tctcggttgt gggtcatgtt atactcgcaa caactttgtg ggctcgagct   1080
aagtccgttg atctgagtag caaaaccgaa ataacttcat gttatatgtt catatggaag   1140
ctcttttatg cagagtactt gctgttacct tttttgaagt ga                      1182
```

<210> SEQ ID NO 2
<211> LENGTH: 393
<212> TYPE: PRT
<213> ORGANISM: Arabidopsis sp

<400> SEQUENCE: 2

```
Met Glu Ser Leu Leu Ser Ser Ser Leu Val Ser Ala Ala Gly Gly
 1               5                  10                  15

Phe Cys Trp Lys Lys Gln Asn Leu Lys Leu His Ser Leu Ser Glu Ile
                20                  25                  30

Arg Val Leu Arg Cys Asp Ser Ser Lys Val Val Ala Lys Pro Lys Phe
            35                  40                  45

Arg Asn Asn Leu Val Arg Pro Asp Gly Gln Gly Ser Ser Leu Leu Leu
        50                  55                  60

Tyr Pro Lys His Lys Ser Arg Phe Arg Val Asn Ala Thr Ala Gly Gln
65                  70                  75                  80

Pro Glu Ala Phe Asp Ser Asn Ser Lys Gln Lys Ser Phe Arg Asp Ser
                85                  90                  95

Leu Asp Ala Phe Tyr Arg Phe Ser Arg Pro His Thr Val Ile Gly Thr
            100                 105                 110

Val Leu Ser Ile Leu Ser Val Ser Phe Leu Ala Val Glu Lys Val Ser
        115                 120                 125

Asp Ile Ser Pro Leu Leu Phe Thr Gly Ile Leu Glu Ala Val Val Ala
    130                 135                 140

Ala Leu Met Met Asn Ile Tyr Ile Val Gly Leu Asn Gln Leu Ser Asp
145                 150                 155                 160

Val Glu Ile Asp Lys Val Asn Lys Pro Tyr Leu Pro Leu Ala Ser Gly
                165                 170                 175

Glu Tyr Ser Val Asn Thr Gly Ile Ala Ile Val Ala Ser Phe Ser Ile
            180                 185                 190

Met Ser Phe Trp Leu Gly Trp Ile Val Gly Ser Trp Pro Leu Phe Trp
        195                 200                 205

Ala Leu Phe Val Ser Phe Met Leu Gly Thr Ala Tyr Ser Ile Asn Leu
    210                 215                 220

Pro Leu Leu Arg Trp Lys Arg Phe Ala Leu Val Ala Ala Met Cys Ile
```

-continued

```
            225                 230                 235                 240
Leu Ala Val Arg Ala Ile Ile Val Gln Ile Ala Phe Tyr Leu His Ile
                        245                 250                 255
Gln Thr His Val Phe Gly Arg Pro Ile Leu Phe Thr Arg Pro Leu Ile
                260                 265                 270
Phe Ala Thr Ala Phe Met Ser Phe Ser Val Val Ile Ala Leu Phe
            275                 280                 285
Lys Asp Ile Pro Asp Ile Glu Gly Asp Lys Ile Phe Gly Ile Arg Ser
290                 295                 300
Phe Ser Val Thr Leu Gly Gln Lys Arg Val Phe Trp Thr Cys Val Thr
305                 310                 315                 320
Leu Leu Gln Met Ala Tyr Ala Val Ala Ile Leu Val Gly Ala Thr Ser
                325                 330                 335
Pro Phe Ile Trp Ser Lys Val Ile Ser Val Val Gly His Val Ile Leu
                340                 345                 350
Ala Thr Thr Leu Trp Ala Arg Ala Lys Ser Val Asp Leu Ser Ser Lys
            355                 360                 365
Thr Glu Ile Thr Ser Cys Tyr Met Phe Ile Trp Lys Leu Phe Tyr Ala
        370                 375                 380
Glu Tyr Leu Leu Leu Pro Phe Leu Lys
385                 390
```

<210> SEQ ID NO 3
<211> LENGTH: 1224
<212> TYPE: DNA
<213> ORGANISM: Arabidopsis sp

<400> SEQUENCE: 3

```
atggcgtttt ttgggctctc ccgtgtttca agacggttgt tgaaatcttc cgtctccgta        60
actccatctt cttcctctgc tcttttgcaa tcacaacata aatccttgtc caatcctgtg       120
actacccatt acacaaatcc tttcactaag tgttatcctt catggaatga taattaccaa       180
gtatggagta aggaagaga attgcatcag gagaagtttt tggtgttgg ttggaattac         240
agattaattt gtggaatgtc gtcgtcttct tcggttttgg agggaaagcc gaagaaagat       300
gataaggaga gagtgatgg tgttgttgtt aagaaagctt cttggataga tttgtattta        360
ccagaagaag ttagaggtta tgctaagctt gctcgattgg ataaacccat ggaacttgg        420
ttgcttgcgt ggccttgtat gtggtcgatt gcgttggctg ctgatcctgg aagccttcca      480
agttttaaat atatggcttt atttggttgc ggagcattac ttcttagagg tgctggttgt       540
actataaatg atctgcttga tcaggacata gatacaaagg ttgatcgtac aaaactaaga       600
cctatcgcca gtggtctttt gacaccattt caagggattg gatttctcgg gctgcagttg       660
cttttaggct tagggattct tctccaactt aacaattaca gccgtgtttt agggggcttca      720
tcttttgttac ttgtcttttc ctacccactt atgaagaggt ttacattttg gcctcaagcc      780
ttttaaggtt tgaccataaa ctggggagca ttgttaggat ggactgcagt taaaggaagc      840
atagcaccat ctattgtact ccctctctat ctctccggag tctgctggac ccttgtttat      900
gatactattt atgcacatca ggacaaagaa gatgatgtaa aagttggtgt taagtcaaca     960
gcccttagat tcggtgataa tacaaagctt tggttaactg gatttggcac agcatccata    1020
ggttttcttg cactttctgg attcagtgca gatctcgggt ggcaatatta cgcatcactg    1080
gccgctgcat caggacagtt aggatggcaa atagggacag ctgacttatc atctggtgct    1140
gactgcagta gaaaatttgt gtcgaacaag tggtttggtg ctattatatt tagtggagtt    1200
```

```
gtacttggaa gaagtttca ataa                                                1224
```

<210> SEQ ID NO 4
<211> LENGTH: 407
<212> TYPE: PRT
<213> ORGANISM: Arabidopsis sp

<400> SEQUENCE: 4

| | | | | | | | | | | | | | | |
|---|---|---|---|---|---|---|---|---|---|---|---|---|---|---|
| Met | Ala | Phe | Phe | Gly | Leu | Ser | Arg | Val | Ser | Arg | Arg | Leu | Leu | Lys | Ser |
| 1 | | | | 5 | | | | | 10 | | | | | 15 | |
| Ser | Val | Ser | Val | Thr | Pro | Ser | Ser | Ser | Ala | Leu | Leu | Gln | Ser | Gln | |
| | | | 20 | | | | | 25 | | | | | 30 | | |
| His | Lys | Ser | Leu | Ser | Asn | Pro | Val | Thr | Thr | His | Tyr | Thr | Asn | Pro | Phe |
| | | 35 | | | | | 40 | | | | | 45 | | | |
| Thr | Lys | Cys | Tyr | Pro | Ser | Trp | Asn | Asp | Asn | Tyr | Gln | Val | Trp | Ser | Lys |
| | 50 | | | | | 55 | | | | | 60 | | | | |
| Gly | Arg | Glu | Leu | His | Gln | Glu | Lys | Phe | Phe | Gly | Val | Gly | Trp | Asn | Tyr |
| 65 | | | | | 70 | | | | | 75 | | | | | 80 |
| Arg | Leu | Ile | Cys | Gly | Met | Ser | Ser | Ser | Ser | Val | Leu | Glu | Gly | Lys | |
| | | | | 85 | | | | | 90 | | | | | 95 | |
| Pro | Lys | Lys | Asp | Asp | Lys | Glu | Lys | Ser | Asp | Gly | Val | Val | Lys | Lys | |
| | | | | 100 | | | | | 105 | | | | | 110 | |
| Ala | Ser | Trp | Ile | Asp | Leu | Tyr | Leu | Pro | Glu | Glu | Val | Arg | Gly | Tyr | Ala |
| | | | 115 | | | | | 120 | | | | | 125 | | |
| Lys | Leu | Ala | Arg | Leu | Asp | Lys | Pro | Ile | Gly | Thr | Trp | Leu | Leu | Ala | Trp |
| | 130 | | | | | 135 | | | | | 140 | | | | |
| Pro | Cys | Met | Trp | Ser | Ile | Ala | Leu | Ala | Ala | Asp | Pro | Gly | Ser | Leu | Pro |
| 145 | | | | | 150 | | | | | 155 | | | | | 160 |
| Ser | Phe | Lys | Tyr | Met | Ala | Leu | Phe | Gly | Cys | Gly | Ala | Leu | Leu | Arg | |
| | | | | 165 | | | | | 170 | | | | | 175 | |
| Gly | Ala | Gly | Cys | Thr | Ile | Asn | Asp | Leu | Leu | Asp | Gln | Asp | Ile | Asp | Thr |
| | | | 180 | | | | | 185 | | | | | 190 | | |
| Lys | Val | Asp | Arg | Thr | Lys | Leu | Arg | Pro | Ile | Ala | Ser | Gly | Leu | Leu | Thr |
| | | 195 | | | | | 200 | | | | | 205 | | | |
| Pro | Phe | Gln | Gly | Ile | Gly | Phe | Leu | Gly | Leu | Gln | Leu | Leu | Gly | Leu | |
| | 210 | | | | | 215 | | | | | 220 | | | | |
| Gly | Ile | Leu | Leu | Gln | Leu | Asn | Asn | Tyr | Ser | Arg | Val | Leu | Gly | Ala | Ser |
| 225 | | | | | 230 | | | | | 235 | | | | | 240 |
| Ser | Leu | Leu | Leu | Val | Phe | Ser | Tyr | Pro | Leu | Met | Lys | Arg | Phe | Thr | Phe |
| | | | | 245 | | | | | 250 | | | | | 255 | |
| Trp | Pro | Gln | Ala | Phe | Leu | Gly | Leu | Thr | Ile | Asn | Trp | Gly | Ala | Leu | Leu |
| | | | 260 | | | | | 265 | | | | | 270 | | |
| Gly | Trp | Thr | Ala | Val | Lys | Gly | Ser | Ile | Ala | Pro | Ser | Ile | Val | Leu | Pro |
| | 275 | | | | | 280 | | | | | 285 | | | | |
| Leu | Tyr | Leu | Ser | Gly | Val | Cys | Trp | Thr | Leu | Val | Tyr | Asp | Thr | Ile | Tyr |
| | 290 | | | | | 295 | | | | | 300 | | | | |
| Ala | His | Gln | Asp | Lys | Glu | Asp | Asp | Val | Lys | Val | Gly | Val | Lys | Ser | Thr |
| 305 | | | | | 310 | | | | | 315 | | | | | 320 |
| Ala | Leu | Arg | Phe | Gly | Asp | Asn | Thr | Lys | Leu | Trp | Leu | Thr | Gly | Phe | Gly |
| | | | | 325 | | | | | 330 | | | | | 335 | |
| Thr | Ala | Ser | Ile | Gly | Phe | Leu | Ala | Leu | Ser | Gly | Phe | Ser | Ala | Asp | Leu |
| | | | 340 | | | | | 345 | | | | | 350 | | |
| Gly | Trp | Gln | Tyr | Tyr | Ala | Ser | Leu | Ala | Ala | Ala | Ser | Gly | Gln | Leu | Gly |
| | 355 | | | | | 360 | | | | | 365 | | | | |

```
Trp Gln Ile Gly Thr Ala Asp Leu Ser Ser Gly Ala Asp Cys Ser Arg
    370                 375                 380

Lys Phe Val Ser Asn Lys Trp Phe Gly Ala Ile Ile Phe Ser Gly Val
385                 390                 395                 400

Val Leu Gly Arg Ser Phe Gln
                405

<210> SEQ ID NO 5
<211> LENGTH: 1296
<212> TYPE: DNA
<213> ORGANISM: Arabidopsis sp

<400> SEQUENCE: 5
atgtggcgaa gatctgttgt ttctcgttta tcttcaagaa tctctgtttc ttcttcgtta      60
ccaaacccta gactgattcc ttggtcccgc gaattatgtg ccgttaatag cttctcccag     120
cctccggtct cgacggaatc aactgctaag ttagggatca ctggtgttag atctgatgcc     180
aatcgagttt tgccactgc tactgccgcc gctacagcta cagctaccac cggtgagatt      240
tcgtctagag ttgcggcttt ggctggatta gggcatcact acgctcgttg ttattgggag     300
ctttctaaag ctaaacttag tatgcttgtg gttgcaactt ctggaactgg gtatattctg     360
ggtacgggaa atgctgcaat tagcttcccg gggctttgtt acacatgtgc aggaaccatg     420
atgattgctg catctgctaa ttccttgaat cagattttg agataagcaa tgattctaag      480
atgaaaagaa cgatgctaag gccattgcct tcaggacgta ttagtgttcc acacgctgtt     540
gcatgggcta ctattgctgg tgcttctggt gcttgtttgt tggccagcaa gactaatatg     600
ttggctgctg gacttgcatc tgccaatctt gtactttatg cgtttgttta tactccgttg     660
aagcaacttc accctatcaa tacatgggtt ggcgctgttg ttggtgctat cccacccttg     720
cttgggtggg cggcagcgtc tggtcagatt tcatacaatt cgatgattct tccagctgct     780
ctttactttt ggcagatacc tcattttatg gcccttgcac atctctgccg caatgattat     840
gcagctggag gttacaagat gttgtcactc tttgatccgt cagggaagag aatagcagca     900
gtggctctaa ggaactgctt tacatgatc cctctcggtt tcatcgccta tgactggggg      960
ttaacctcaa gttggttttg cctcgaatca acacttctca cactagcaat cgctgcaaca    1020
gcattttcat tctaccgaga ccggaccatg cataaagcaa ggaaaatgtt ccatgccagt    1080
cttctcttcc ttcctgtttt catgtctggt cttcttctac accgtgtctc taatgataat    1140
cagcaacaac tcgtagaaga agccggatta acaaattctg tatctggtga agtcaaaact    1200
cagaggcgaa agaaacgtgt ggctcaacct ccggtggctt atgcctctgc tgcaccgttt    1260
cctttcctcc cagctccttc cttctactct ccatga                             1296

<210> SEQ ID NO 6
<211> LENGTH: 431
<212> TYPE: PRT
<213> ORGANISM: Arabidopsis sp

<400> SEQUENCE: 6

Met Trp Arg Arg Ser Val Val Tyr Arg Phe Ser Arg Ile Ser Val
1               5                   10                  15

Ser Ser Ser Leu Pro Asn Pro Arg Leu Ile Pro Trp Ser Arg Glu Leu
                20                  25                  30

Cys Ala Val Asn Ser Phe Ser Gln Pro Pro Val Ser Thr Glu Ser Thr
            35                  40                  45
```

-continued

```
Ala Lys Leu Gly Ile Thr Gly Val Arg Ser Asp Ala Asn Arg Val Phe
 50                  55                  60
Ala Thr Ala Thr Ala Ala Thr Ala Thr Thr Gly Glu Ile
 65              70              75              80
Ser Ser Arg Val Ala Ala Leu Ala Gly Leu Gly His His Tyr Ala Arg
                 85                  90                  95
Cys Tyr Trp Glu Leu Ser Lys Ala Lys Leu Ser Met Leu Val Val Ala
            100                 105                 110
Thr Ser Gly Thr Gly Tyr Ile Leu Gly Thr Gly Asn Ala Ala Ile Ser
                115                 120                 125
Phe Pro Gly Leu Cys Tyr Thr Cys Ala Gly Thr Met Met Ile Ala Ala
            130                 135                 140
Ser Ala Asn Ser Leu Asn Gln Ile Phe Glu Ile Ser Asn Asp Ser Lys
145                 150                 155                 160
Met Lys Arg Thr Met Leu Arg Pro Leu Pro Ser Gly Arg Ile Ser Val
                165                 170                 175
Pro His Ala Val Ala Trp Ala Thr Ile Ala Gly Ala Ser Gly Ala Cys
                180                 185                 190
Leu Leu Ala Ser Lys Thr Asn Met Leu Ala Ala Gly Leu Ala Ser Ala
            195                 200                 205
Asn Leu Val Leu Tyr Ala Phe Val Tyr Thr Pro Leu Lys Gln Leu His
            210                 215                 220
Pro Ile Asn Thr Trp Val Gly Ala Val Gly Ala Ile Pro Pro Leu
225                 230                 235                 240
Leu Gly Trp Ala Ala Ala Ser Gly Gln Ile Ser Tyr Asn Ser Met Ile
                245                 250                 255
Leu Pro Ala Ala Leu Tyr Phe Trp Gln Ile Pro His Phe Met Ala Leu
            260                 265                 270
Ala His Leu Cys Arg Asn Asp Tyr Ala Ala Gly Tyr Lys Met Leu
            275                 280                 285
Ser Leu Phe Asp Pro Ser Gly Lys Arg Ile Ala Ala Val Ala Leu Arg
            290                 295                 300
Asn Cys Phe Tyr Met Ile Pro Leu Gly Phe Ile Ala Tyr Asp Trp Gly
305                 310                 315                 320
Leu Thr Ser Ser Trp Phe Cys Leu Glu Ser Thr Leu Leu Thr Leu Ala
                325                 330                 335
Ile Ala Thr Ala Phe Ser Phe Tyr Arg Asp Arg Thr Met His Lys
            340                 345                 350
Ala Arg Lys Met Phe His Ala Ser Leu Leu Phe Leu Pro Val Phe Met
            355                 360                 365
Ser Gly Leu Leu Leu His Arg Val Ser Asn Asp Asn Gln Gln Leu
            370                 375                 380
Val Glu Glu Ala Gly Leu Thr Asn Ser Val Ser Gly Glu Val Lys Thr
385                 390                 395                 400
Gln Arg Arg Lys Lys Arg Val Ala Gln Pro Val Ala Tyr Ala Ser
                405                 410                 415
Ala Ala Pro Phe Pro Phe Leu Pro Ala Pro Ser Phe Tyr Ser Pro
            420                 425                 430
```

<210> SEQ ID NO 7
<211> LENGTH: 479
<212> TYPE: DNA
<213> ORGANISM: Arabidopsis sp

<400> SEQUENCE: 7

```
ggaaactccc ggagcacctg tttgcaggta ccgctaacct taatcgataa tttatttctc      60
ttgtcaggaa ttatgtaagt ctggtggaag gctcgcatac cattttttgca ttgcctttcg    120 ctatgatcgg gtttactttg ggtgtgatga gaccaggcgt ggctttatgg tatggcgaaa    180
acccattttt atccaatgct gcattccctc ccgatgattc gttctttcat tcctatacag    240
gtatcatgct gataaaactg ttactggtac tggtttgtat ggtatcagca agaagcgcgg    300
cgatggcgtt taaccggtat ctcgacaggc attttgacgc gaagaacccg cgtactgcca    360
tccgtgaaat acctgcgggc gtcatatctg ccaacagtgc gctggtgttt acgataggct    420
gctgcgtggt attctgggtg gcctgttatt tcattaacac gatctgtttt tacctggcg    479

<210> SEQ ID NO 8
<211> LENGTH: 551
<212> TYPE: DNA
<213> ORGANISM: Arabidopsis sp
<220> FEATURE:
<221> NAME/KEY: misc_feature
<222> LOCATION: (1)...(551)
<223> OTHER INFORMATION: n = A,T,C or G

<400> SEQUENCE: 8
ttgtggctta caccttaatg agcatacgcc agnccattac ggctcgttaa tcggcgccat     60
ngccggngct gntgcaccgg tagtgggcta ctgcgccgtg accaatcagc ttgatctagc    120
ggctcttatt ctgtttttaa ttttactgtt ctggcaaatg ccgcattttt acgcgatttc    180
cattttcagg ctaaaagact tttcagcggc ctgtattccg gtgctgccca tcattaaaga    240
cctgcgctat accaaaatca gcatgctggt ttacgtgggc ttatttacac tggctgctat    300
catgccggcc ctcttagggt atgccggttg gatttatggg atagcggcct taattttagg    360
cttgtattgg ctttatattg ccatacaagg attcaagacc gccgatgatc aaaaatggtc    420
tcgtaagatg tttggatctt cgatttttaat cattaccctc ttgtcggtaa tgatgcttgt    480
ttaaacttac tgcctcctga agtttatata tcgataattt cagcttaagg aggcttagtg    540
gttaattcaa t                                                        551

<210> SEQ ID NO 9
<211> LENGTH: 297
<212> TYPE: PRT
<213> ORGANISM: Arabidopsis sp

<400> SEQUENCE: 9

Met Val Leu Ala Glu Val Pro Lys Leu Ala Ser Ala Ala Glu Tyr Phe
  1               5                  10                  15

Phe Lys Arg Gly Val Gln Gly Lys Gln Phe Arg Ser Thr Ile Leu Leu
             20                  25                  30

Leu Met Ala Thr Ala Leu Asn Val Arg Val Pro Glu Ala Leu Ile Gly
         35                  40                  45

Glu Ser Thr Asp Ile Val Thr Ser Glu Leu Arg Val Arg Gln Arg Gly
     50                  55                  60

Ile Ala Glu Ile Thr Glu Met Ile His Val Ala Ser Leu Leu His Asp
 65                  70                  75                  80

Asp Val Leu Asp Asp Ala Asp Thr Arg Arg Gly Val Gly Ser Leu Asn
                 85                  90                  95

Val Val Met Gly Asn Lys Val Ala Leu Leu Ala Thr Ala Val Glu
            100                 105                 110

His Leu Val Thr Gly Glu Thr Met Glu Ile Thr Ser Ser Thr Glu Gln
```

-continued

```
           115                 120                 125
Arg Tyr Ser Met Asp Tyr Tyr Met Gln Lys Thr Tyr Tyr Lys Thr Ala
    130                 135                 140
Ser Leu Ile Ser Asn Ser Cys Lys Ala Val Ala Val Leu Thr Gly Gln
145                 150                 155                 160
Thr Ala Glu Val Ala Val Leu Ala Phe Glu Tyr Gly Arg Asn Leu Gly
                165                 170                 175
Leu Ala Phe Gln Leu Ile Asp Asp Ile Leu Asp Phe Thr Gly Thr Ser
            180                 185                 190
Ala Ser Leu Gly Lys Gly Ser Leu Ser Asp Ile Arg His Gly Val Ile
        195                 200                 205
Thr Ala Pro Ile Leu Phe Ala Met Glu Glu Phe Pro Gln Leu Arg Glu
    210                 215                 220
Val Val Asp Gln Val Glu Lys Asp Pro Arg Asn Val Asp Ile Ala Leu
225                 230                 235                 240
Glu Tyr Leu Gly Lys Ser Lys Gly Ile Gln Arg Ala Arg Glu Leu Ala
                245                 250                 255
Met Glu His Ala Asn Leu Ala Ala Ala Ile Gly Ser Leu Pro Glu
            260                 265                 270
Thr Asp Asn Glu Asp Val Lys Arg Ser Arg Arg Ala Leu Ile Asp Leu
        275                 280                 285
Thr His Arg Val Ile Thr Arg Asn Lys
    290                 295

<210> SEQ ID NO 10
<211> LENGTH: 561
<212> TYPE: DNA
<213> ORGANISM: Arabidopsis sp

<400> SEQUENCE: 10
aagcgcatcc gtcctcttct acgattgccg ccagccgcat gtatggctgc ataaccgacc      60
gcccctatcc gctcgcggcc gcggtcgaat tcattcacac cgcgacgctg ctgcatgacg     120
acgtcgtcga tgaaagcgat ttgcgccgcg ccgcgaaag cgcgcataag gttttcggca     180
atcaggcgag cgtgctcgtc ggcgatttcc ttttctcccg cgccttccag ctgatggtgg     240
aagacggctc gctcgacgcg ctgcgcattc tctcggatgc ctccgccgtg atcgcgcagg     300
gcgaagtgat gcagctcggc accgcgcgca atcttgaaac caatatgagc cagtatctcg     360
atgtgatcag cgcgaagacc gccgcgctct tgccgccgc ctgcgaaatc ggcccggtga     420
tggcgaacgc gaaggcggaa gatgctgccg cgatgtgcga atacggcatg aatctcggta     480
tcgccttcca gatcatcgac gaccttctcg attacggcac cggcggccac gccgagcttg     540
gcaagaacac gggcgacgat t                                              561

<210> SEQ ID NO 11
<211> LENGTH: 966
<212> TYPE: DNA
<213> ORGANISM: Arabidopsis sp

<400> SEQUENCE: 11
atggtacttg ccgaggttcc aaagcttgcc tctgctgctg agtacttctt caaaagggt      60
gtgcaaggaa aacagtttcg ttcaactatt ttgctgctga tggcgacagc tctgaatgta     120
cgcgttccag aagcattgat tggggaatca acagatatag tcacatcaga attacgcgta     180
aggcaacggg gtattgctga aatcactgaa atgatacacg tcgcaagtct actgcacgat     240
```

-continued

```
gatgtcttgg atgatgccga tacaaggcgt ggtgttggtt ccttaaatgt tgtaatgggt    300
aacaagatgt cggtattagc aggagacttc ttgctctccc gggcttgtgg ggctctcgct    360
gctttaaaga acacagaggt tgtagcatta cttgcaactg ctgtagaaca tcttgttacc    420
ggtgaaacca tggaaataac tagttcaacc gagcagcgtt atagtatgga ctactacatg    480
cagaagacat attataagac agcatcgcta atctctaaca gctgcaaagc tgttgccgtt    540
ctcactggac aaacagcaga agttgccgtg ttagcttttg agtatgggag gaatctgggt    600
ttagcattcc aattaataga cgacattctt gatttcacgg gcacatctgc ctctctcgga    660
aagggatcgt tgtcagatat tcgccatgga gtcataacag ccccaatcct ctttgccatg    720
gaagagtttc ctcaactacg cgaagttgtt gatcaagttg aaaaagatcc taggaatgtt    780
gacattgctt tagagtatct tgggaagagc aagggaatac agagggcaag agaattagcc    840
atggaacatg cgaatctagc agcagctgca atcgggtctc tacctgaaac agacaatgaa    900
gatgtcaaaa gatcgaggcg ggcacttatt gacttgaccc atagagtcat caccagaaac    960
aagtga                                                               966
```

<210> SEQ ID NO 12
<211> LENGTH: 321
<212> TYPE: PRT
<213> ORGANISM: Arabidopsis sp

<400> SEQUENCE: 12

```
Met Val Leu Ala Glu Val Pro Lys Leu Ala Ser Ala Ala Glu Tyr Phe
  1               5                  10                  15

Phe Lys Arg Gly Val Gln Gly Lys Gln Phe Arg Ser Thr Ile Leu Leu
             20                  25                  30

Leu Met Ala Thr Ala Leu Asn Val Arg Val Pro Glu Ala Leu Ile Gly
         35                  40                  45

Glu Ser Thr Asp Ile Val Thr Ser Glu Leu Arg Val Arg Gln Arg Gly
     50                  55                  60

Ile Ala Glu Ile Thr Glu Met Ile His Val Ala Ser Leu Leu His Asp
 65                  70                  75                  80

Asp Val Leu Asp Asp Ala Asp Thr Arg Arg Gly Val Gly Ser Leu Asn
                 85                  90                  95

Val Val Met Gly Asn Lys Met Ser Val Leu Ala Gly Asp Phe Leu Leu
            100                 105                 110

Ser Arg Ala Cys Gly Ala Leu Ala Ala Leu Lys Asn Thr Glu Val Val
        115                 120                 125

Ala Leu Leu Ala Thr Ala Val Glu His Leu Val Thr Gly Glu Thr Met
    130                 135                 140

Glu Ile Thr Ser Ser Thr Glu Gln Arg Tyr Ser Met Asp Tyr Tyr Met
145                 150                 155                 160

Gln Lys Thr Tyr Tyr Lys Thr Ala Ser Leu Ile Ser Asn Ser Cys Lys
                165                 170                 175

Ala Val Ala Val Leu Thr Gly Gln Thr Ala Glu Val Ala Val Leu Ala
            180                 185                 190

Phe Glu Tyr Gly Arg Asn Leu Gly Leu Ala Phe Gln Leu Ile Asp Asp
        195                 200                 205

Ile Leu Asp Phe Thr Gly Thr Ser Ala Ser Leu Gly Lys Gly Ser Leu
    210                 215                 220

Ser Asp Ile Arg His Gly Val Ile Thr Ala Pro Ile Leu Phe Ala Met
225                 230                 235                 240
```

```
Glu Glu Phe Pro Gln Leu Arg Glu Val Val Asp Gln Val Glu Lys Asp
                245                 250                 255
Pro Arg Asn Val Asp Ile Ala Leu Glu Tyr Leu Gly Lys Ser Lys Gly
            260                 265                 270
Ile Gln Arg Ala Arg Glu Leu Ala Met Glu His Ala Asn Leu Ala Ala
        275                 280                 285
Ala Ala Ile Gly Ser Leu Pro Glu Thr Asp Asn Glu Asp Val Lys Arg
    290                 295                 300
Ser Arg Arg Ala Leu Ile Asp Leu Thr His Arg Val Ile Thr Arg Asn
305                 310                 315                 320
Lys
```

<210> SEQ ID NO 13
<211> LENGTH: 621
<212> TYPE: DNA
<213> ORGANISM: Arabidopsis sp

<400> SEQUENCE: 13

| | | | | | | |
|---|---|---|---|---|---|---|
| gctttctcct | tgctaattc | ttgagctttc | ttgatcccac | cgcgatttct | aactatttca | 60 |
| atcgcttctt | caagcgatcc | aggctcacaa | aactcagact | caatgatctc | tcttagcctt | 120 |
| ggctcattct | ctagcgcgaa | gatcactggc | gccgttatgt | tacctttggc | taagtcatta | 180 |
| gctgcaggct | tacctaactg | ctctgtggac | tgagtgaagt | ccagaatgtc | atcaactact | 240 |
| tgaaaagata | aaccgagatt | cttcccgaac | tgatacattt | gctctgcgac | cttgctttcg | 300 |
| actttactga | aaattgctgc | tcctttggtg | cttgcagcta | ctaatgaagc | tgtcttgtag | 360 |
| taactcttta | gcatgtagtc | atcaagcttg | acatcacaat | cgaataaact | cgatgcttgc | 420 |
| tttatctcac | cgcttgcaaa | atctttgatc | acctgcaaaa | agataaatca | agattcagac | 480 |
| caaatgttct | ttgtattgag | tagcttcatc | taatctcaga | aaggaatatt | acctgactta | 540 |
| tgagcttaat | gacttcaagg | ttttcgagat | ttgtaagtac | catgatgctt | gagcaacatg | 600 |
| aaatccccag | ctaatacagc | t | | | | 621 |

<210> SEQ ID NO 14
<211> LENGTH: 741
<212> TYPE: DNA
<213> ORGANISM: Arabidopsis sp

<400> SEQUENCE: 14

| | | | | | | |
|---|---|---|---|---|---|---|
| ggtgagtttt | gttaatagtt | atgagattca | tctattttg | tcataaaatt | gtttggtttg | 60 |
| gtttaaactc | tgtgtataat | tgcaggaaag | gaaacagttc | atgagctttt | cggcacaaga | 120 |
| gtagcggtgc | tagctggaga | tttcatgttt | gctcaagcgt | catggtactt | agcaaatctc | 180 |
| gagaatcttg | aagttattaa | gctcatcagt | caggtactta | gttactctta | cattgttttt | 240 |
| ctatgaggtt | gagctatgaa | tctcatttcg | ttgaataatg | ctgtgcctca | aactttttt | 300 |
| catgttttca | ggtgatcaaa | gactttgcaa | gcggagagat | aaagcaggcg | tccagcttat | 360 |
| ttgactgcga | caccaagctc | gacgagtact | tactcaaaag | tttctacaag | acagcctctt | 420 |
| tagtggctgc | gagcaccaaa | ggagctgcca | ttttcagcag | agttgagcct | gatgtgacag | 480 |
| aacaaatgta | cgagtttggg | aagaatctcg | gtctctcttt | ccagatagtt | gatgatattt | 540 |
| tggatttcac | tcagtcgaca | gagcagctcg | ggaagccagc | agggagtgat | ttggctaaag | 600 |
| gtaacttaac | agcacctgtg | attttcgctc | tggagaggga | gccaaggcta | agagagatca | 660 |
| ttgagtcaaa | gttctgtgag | gcgggttctc | tggaagaagc | gattgaagcg | gtgacaaaag | 720 |

| | |
|---|---|
| gtgggggat taagagagca c | 741 |

<210> SEQ ID NO 15
<211> LENGTH: 1087
<212> TYPE: DNA
<213> ORGANISM: Arabidopsis sp

<400> SEQUENCE: 15

| | |
|---|---|
| cctcttcagc caatccagag gaagaagaga caacttttta tctttcgtca agagtctccg | 60 |
| aaaacgcacg gttttatgct ctctcttctg ccctcacctc acaagacgca gggcacatga | 120 |
| ttcaaccaga gggaaaaagc aacgataaca actctgcttt tgatttcaag ctgtatatga | 180 |
| tccgcaaagc cgagtctgta aatgcggctc tcgacgtttc cgtaccgctt ctgaaacccc | 240 |
| ttacgatcca agaagcggtc aggtactctt tgctagccgg cggaaaacgt gtgaggcctc | 300 |
| tgctctgcat tgccgcttgt gagcttgtgg ggcgacga ggctactgcc atgtcagccg | 360 |
| cttgcgcggt cgagatgatc cacacaagct ctctcattca tgacgatctt ccgtgcatgg | 420 |
| acaatgccga cctccgtaga ggcaagccca ccaatcacaa ggtatgttgt ttaattatat | 480 |
| gaaggctcag agataatgct gaactagtgt tgaaccaatt tttgctcaaa caaggtatat | 540 |
| ggagaagaca tggcggtttt ggcaggtgat gcactccttg cattggcgtt tgagcacatg | 600 |
| acggttgtgt cgagtgggtt ggtcgctccc gagaagatga ttcgcgccgt ggttgagctg | 660 |
| gccagggcca tagggactac agggctagtt gctggacaaa tgatagacct agccagcgaa | 720 |
| agactgaatc cagacaaggt tggattggag catctagagt tcatccatct ccacaaaacg | 780 |
| gcggcattgt tggaggcagc ggcagtttta ggggttataa tgggaggtgg aacagaggaa | 840 |
| gaaatcgaaa agcttagaaa gtatgctagg tgtattggac tactgtttca ggttgttgat | 900 |
| gacattctcg acgtaacaaa atctactgag gaattgggta agacagccgg aaaagacgta | 960 |
| atggccggaa agctgacgta tccaaggctg ataggtttgg agggatccag ggaagttgca | 1020 |
| gagcacctga ggagagaagc agaggaaaag cttaaagggt ttgatccaag tcaggcggcg | 1080 |
| cctctgg | 1087 |

<210> SEQ ID NO 16
<211> LENGTH: 1164
<212> TYPE: DNA
<213> ORGANISM: Arabidopsis sp

<400> SEQUENCE: 16

| | |
|---|---|
| atgacttcga ttctcaacac tgtctccacc atccactctt ccagagttac ctccgtcgat | 60 |
| cgagtcggag tcctctctct tcggaattcg gattccgttg agttcactcg ccggcgttct | 120 |
| ggtttctcga cgttgatcta cgaatcaccc gggcggagat tgttgtgcg tgcggcggag | 180 |
| actgatactg ataaagttaa atctcagaca cctgacaagg caccagccgg tggttcaagc | 240 |
| attaaccagc ttctcggtat caaaggagca tctcaagaaa ctaataaatg gaagattcgt | 300 |
| cttcagctta caaaaccagt cacttggcct ccactggttt ggggagtcgt ctgtggtgct | 360 |
| gctgcttcag ggaactttca ttggaccccca gaggatgttg ctaagtcgat tctttgcatg | 420 |
| atgatgtctg tccttgtct tactggctat acacagacaa tcaacgactg gtatgataga | 480 |
| gatatcgacg caattaatga gccatatcgt ccaattccat ctggagcaat atcagagcca | 540 |
| gaggttatta cacaagtctg ggtgctatta ttgggaggtc ttggtattgc tggaatatta | 600 |
| gatgtgtggg cagggcatac cactcccact gtcttctatc ttgctttggg aggatcattg | 660 |
| ctatcttata tatactctgc tccacctctt aagctaaaac aaaatggatg ggttggaaat | 720 |

```
tttgcacttg gagcaagcta tattagtttg ccatggtggg ctggccaagc attgtttggc    780
actcttacgc cagatgttgt tgttctaaca ctcttgtaca gcatagctgg gttaggaata    840
gccattgtta acgacttcaa aagtgttgaa ggagatagag cattaggact tcagtctctc    900
ccagtagctt ttggcaccga aactgcaaaa tggatatgcg ttggtgctat agacattact    960
cagctttctg ttgccggata tctattagca tctgggaaac cttattatgc gttggcgttg   1020
gttgctttga tcattcctca gattgtgttc cagtttaaat actttctcaa ggaccctgtc   1080
aaatacgacg tcaagtacca ggcaagcgcg cagccattct tggtgctcgg aatatttgta   1140
acggcattag catcgcaaca ctga                                           1164
```

<210> SEQ ID NO 17
<211> LENGTH: 387
<212> TYPE: PRT
<213> ORGANISM: Arabidopsis sp

<400> SEQUENCE: 17

```
Met Thr Ser Ile Leu Asn Thr Val Ser Thr Ile His Ser Ser Arg Val
  1               5                  10                  15

Thr Ser Val Asp Arg Val Gly Val Leu Ser Leu Arg Asn Ser Asp Ser
             20                  25                  30

Val Glu Phe Thr Arg Arg Arg Ser Gly Phe Ser Thr Leu Ile Tyr Glu
         35                  40                  45

Ser Pro Gly Arg Arg Phe Val Arg Ala Ala Glu Thr Asp Thr Asp
     50                  55                  60

Lys Val Lys Ser Gln Thr Pro Asp Lys Ala Pro Ala Gly Gly Ser Ser
 65                  70                  75                  80

Ile Asn Gln Leu Leu Gly Ile Lys Gly Ala Ser Gln Glu Thr Asn Lys
                 85                  90                  95

Trp Lys Ile Arg Leu Gln Leu Thr Lys Pro Val Thr Trp Pro Pro Leu
            100                 105                 110

Val Trp Gly Val Val Cys Gly Ala Ala Ala Ser Gly Asn Phe His Trp
        115                 120                 125

Thr Pro Glu Asp Val Ala Lys Ser Ile Leu Cys Met Met Met Ser Gly
    130                 135                 140

Pro Cys Leu Thr Gly Tyr Thr Gln Thr Ile Asn Asp Trp Tyr Asp Arg
145                 150                 155                 160

Asp Ile Asp Ala Ile Asn Glu Pro Tyr Arg Pro Ile Pro Ser Gly Ala
                165                 170                 175

Ile Ser Glu Pro Glu Val Ile Thr Gln Val Trp Val Leu Leu Leu Gly
            180                 185                 190

Gly Leu Gly Ile Ala Gly Ile Leu Asp Val Trp Ala Gly His Thr Thr
        195                 200                 205

Pro Thr Val Phe Tyr Leu Ala Leu Gly Gly Ser Leu Leu Ser Tyr Ile
    210                 215                 220

Tyr Ser Ala Pro Pro Leu Lys Leu Lys Gln Asn Gly Trp Val Gly Asn
225                 230                 235                 240

Phe Ala Leu Gly Ala Ser Tyr Ile Ser Leu Pro Trp Trp Ala Gly Gln
                245                 250                 255

Ala Leu Phe Gly Thr Leu Thr Pro Asp Val Val Leu Thr Leu Leu
            260                 265                 270

Tyr Ser Ile Ala Gly Leu Gly Ile Ala Ile Val Asn Asp Phe Lys Ser
        275                 280                 285
```

-continued

```
Val Glu Gly Asp Arg Ala Leu Gly Leu Gln Ser Leu Pro Val Ala Phe
    290                 295                 300
Gly Thr Glu Thr Ala Lys Trp Ile Cys Val Gly Ala Ile Asp Ile Thr
305                 310                 315                 320
Gln Leu Ser Val Ala Gly Tyr Leu Leu Ala Ser Gly Lys Pro Tyr Tyr
                325                 330                 335
Ala Leu Ala Leu Val Ala Leu Ile Ile Pro Gln Ile Val Phe Gln Phe
            340                 345                 350
Lys Tyr Phe Leu Lys Asp Pro Val Lys Tyr Asp Val Lys Tyr Gln Ala
        355                 360                 365
Ser Ala Gln Pro Phe Leu Val Leu Gly Ile Phe Val Thr Ala Leu Ala
    370                 375                 380
Ser Gln His
385
```

<210> SEQ ID NO 18
<211> LENGTH: 981
<212> TYPE: DNA
<213> ORGANISM: Arabidopsis sp

<400> SEQUENCE: 18

| | |
|---|---|
| atgttgttta gtggttcagc gatcccatta agcagcttct gctctcttcc ggagaaaccc | 60 |
| cacactcttc ctatgaaact ctctcccgct gcaatccgat cttcatcctc atctgccccg | 120 |
| gggtcgttga acttcgatct gaggacgtat tggacgactc tgatcaccga gatcaaccag | 180 |
| aagctggatg aggccatacc ggtcaagcac cctgcgggga tctacgaggc tatgagatac | 240 |
| tctgtactcg cacaaggcgc caagcgtgcc ctcctgtga tgtgtgtggc ggcctgcgag | 300 |
| ctcttcggtg gcgatcgcct cgccgctttc cccaccgcct gtgccctaga atggtgcac | 360 |
| gcggcttcgt tgatacacga cgacctcccc tgtatggacg acgatcctgt gcgcagagga | 420 |
| aagccatcta accacactgt ctacgctct ggcatggcca ttctcgccgg tgacgccctc | 480 |
| ttcccactcg ccttccagca cattgtctcc cacacgcctc ctgaccttgt tccccgagcc | 540 |
| accatcctca gactcatcac tgagattgcc cgcactgtcg gctccactgg tatggctgca | 600 |
| ggccagtacg tcgaccttga aggaggtccc ttttcctcttt cctttgttca ggagaagaaa | 660 |
| tcggagcca tgggtgaatg ctctgccgtg tgcggtggcc tattgggcgg tgccactgag | 720 |
| gatgagctcc agagtctccg aaggtacggg agagccgtcg ggatgctgta tcaggtggtc | 780 |
| gatgacatca ccgaggacaa gaagaagagc tatgatggtg gagcagagaa gggaatgatg | 840 |
| gaaatggcgg aagagctcaa ggagaaggcg aagaaggagc ttcaagtgtt tgacaacaag | 900 |
| tatggaggag gagacacact tgttcctctc tacaccttcg ttgactacgc tgctcatcga | 960 |
| cattttcttc ttcccctctg a | 981 |

<210> SEQ ID NO 19
<211> LENGTH: 245
<212> TYPE: DNA
<213> ORGANISM: GLycine sp

<400> SEQUENCE: 19

| | |
|---|---|
| gcaacatctg ggactgggtt tgtcttgggg agtggtagtg ctgttgatct ttcggcactt | 60 |
| tcttgcactt gcttgggtac catgatggtt gctgcatctg ctaactcttt gaatcaggtg | 120 |
| tttgagatca ataatgatgc taaaatgaag agaacaagtc gcaggccact accctcagga | 180 |
| cgcatcacaa tacctcatgc agttggctgg gcatcctctg ttggattagc tggtacggct | 240 |

```
ctact                                                                      245

<210> SEQ ID NO 20
<211> LENGTH: 253
<212> TYPE: DNA
<213> ORGANISM: Glycine sp

<400> SEQUENCE: 20
attggctttc caagatcatt gggttttctt gttgcattca tgaccttcta ctccttgggt           60
ttggcattgt ccaaggatat acctgacgtt gaaggagata aagagcacgg cattgattct         120
tttgcagtac gtctaggtca gaaacgggca ttttggattt gcgtttcctt ttttgaaatg         180
gctttcggag ttggtatcct ggccggagca tcatgctcac acttttggac taaaattttc         240
acgggtatgg gaa                                                            253

<210> SEQ ID NO 21
<211> LENGTH: 275
<212> TYPE: DNA
<213> ORGANISM: Glycine sp

<400> SEQUENCE: 21
tgatcttcta ctctctgggt atggcattgt ccaaggatat atctgacgtt aaaggagata          60
aagcatacgg catcgatact ttagcgatac gtttgggtca aaaatgggta ttttggattt        120
gcattatcct ttttgaaatg cttttggag ttgccctctt ggcaggagca acatcttctt         180
acctttggat taaaattgtc acgggtctgg gacatgctat tcttgcttca attctcttgt         240
accaagccaa atctatatac ttgagcaaca aagtt                                    275

<210> SEQ ID NO 22
<211> LENGTH: 299
<212> TYPE: DNA
<213> ORGANISM: Glycine sp
<220> FEATURE:
<221> NAME/KEY: misc_feature
<222> LOCATION: (1)...(299)
<223> OTHER INFORMATION: n = A,T,C or G

<400> SEQUENCE: 22
ccanaatang tncatcttng aaagacaatt ggcctcttca acacacaagt ctgcatgtga          60
agaagaggcc aattgtcttt ccaagatcac ttatngtggc tattgtaatc atgaacttct        120
tctttgtggg tatggcattg gcaaggata tacctanctg ttgaaggaga taaaatatat         180
ggcattgata cttttgcaat acgtataggt caaaaacaag tattttggat ttgtattttc        240 cttttttgaaa ggctttcgga gtttccctag tggcaggagc aacatcttct agccttggt        299

<210> SEQ ID NO 23
<211> LENGTH: 767
<212> TYPE: DNA
<213> ORGANISM: Glycine sp

<400> SEQUENCE: 23
gtggaggctg tggttgctgc cctgtttatg aatatttata ttgttggttt gaatcaattg          60
tctgatgttg aaatagacaa gataaacaag ccgtatcttc cattagcatc tggggaatat        120
tcctttgaaa ctggtgtcac tattgttgca tcttttcaa ttctgagttt ttggcttggc         180
tgggttgtag gttcatggcc attatttggg gcccttttg taagctttgt gctaggaact         240
gcttattcaa tcaatgtgcc tctgttgaga tggaagaggt ttgcagtgct tgcagcgatg        300
tgcattctag ctgttcgggc agtaatagtt caacttgcat ttttccttca catgcagact        360
```

```
catgtgtaca agaggccacc tgtctttttca agaccattga tttttgctac tgcattcatg      420
agcttcttct ctgtagttat agcactgttt aaggatatac ctgacattga aggagataaa      480
gtatttggca tccaatcttt ttcagtgtgt ttaggtcaga agccggtgtt ctggacttgt      540
gttaccctcc ttgaaatagc ttatggagtc gccctcctgg tgggagctgc atctccttgt      600
ctttggagca aaattttcac gggtctggga cacgctgtgc tggcttcaat tctctggttt      660
catgccaaat ctgtagattt gaaaagcaaa gcttcgataa catccttcta tatgtttatt      720
tggaagctat tttatgcaga atacttactc attccttttg ttagatg                   767
```

<210> SEQ ID NO 24
<211> LENGTH: 255
<212> TYPE: PRT
<213> ORGANISM: Glycine sp

<400> SEQUENCE: 24

```
Val Glu Ala Val Val Ala Ala Leu Phe Met Asn Ile Tyr Ile Val Gly
  1               5                  10                  15

Leu Asn Gln Leu Ser Asp Val Glu Ile Asp Lys Ile Asn Lys Pro Tyr
             20                  25                  30

Leu Pro Leu Ala Ser Gly Glu Tyr Ser Phe Glu Thr Gly Val Thr Ile
         35                  40                  45

Val Ala Ser Phe Ser Ile Leu Ser Phe Trp Leu Gly Trp Val Val Gly
     50                  55                  60

Ser Trp Pro Leu Phe Trp Ala Leu Phe Val Ser Phe Val Leu Gly Thr
 65                  70                  75                  80

Ala Tyr Ser Ile Asn Val Pro Leu Leu Arg Trp Lys Arg Phe Ala Val
                 85                  90                  95

Leu Ala Ala Met Cys Ile Leu Ala Val Arg Ala Val Ile Val Gln Leu
            100                 105                 110

Ala Phe Phe Leu His Met Gln Thr His Val Tyr Lys Arg Pro Pro Val
        115                 120                 125

Phe Ser Arg Pro Leu Ile Phe Ala Thr Ala Phe Met Ser Phe Phe Ser
    130                 135                 140

Val Val Ile Ala Leu Phe Lys Asp Ile Pro Asp Ile Glu Gly Asp Lys
145                 150                 155                 160

Val Phe Gly Ile Gln Ser Phe Ser Val Cys Leu Gly Gln Lys Pro Val
                165                 170                 175

Phe Trp Thr Cys Val Thr Leu Leu Glu Ile Ala Tyr Gly Val Ala Leu
            180                 185                 190

Leu Val Gly Ala Ala Ser Pro Cys Leu Trp Ser Lys Ile Phe Thr Gly
        195                 200                 205

Leu Gly His Ala Val Leu Ala Ser Ile Leu Trp Phe His Ala Lys Ser
    210                 215                 220

Val Asp Leu Lys Ser Lys Ala Ser Ile Thr Ser Phe Tyr Met Phe Ile
225                 230                 235                 240

Trp Lys Leu Phe Tyr Ala Glu Tyr Leu Leu Ile Pro Phe Val Arg
                245                 250                 255
```

<210> SEQ ID NO 25
<211> LENGTH: 360
<212> TYPE: DNA
<213> ORGANISM: Zea sp
<220> FEATURE:
<221> NAME/KEY: misc_feature
<222> LOCATION: (1)...(360)

<223> OTHER INFORMATION: n = A,T,C or G

<400> SEQUENCE: 25

```
ggcgtcttca cttgttctgg tcttctcgta tccctgatg aagaggttca cattttggcc      60
tcaggcttat cttggcctga cattcaactg gggagcttta ctagggtggg ctgctattaa    120
ggaaagcata gaccctgcaa atcatccttc cattgtatac agctggtatt tgttggacgc    180
tggtgtatga tactatatat gcgcatcagg tgtttcgcta tccctacttt catattaatc    240
cttgatgaag tggccatttc atgttgtcgc ggtggtctta tacttgcata tctccatgca    300
tctcaggaca aagangatga cctgaaagta ggagtccaag tccacagctt aagatttggg    360
```

<210> SEQ ID NO 26
<211> LENGTH: 299
<212> TYPE: DNA
<213> ORGANISM: Zea sp
<220> FEATURE:
<221> NAME/KEY: misc_feature
<222> LOCATION: (1)...(299)
<223> OTHER INFORMATION: n = A,T,C or G

<400> SEQUENCE: 26

```
gatggttgca gcatctgcaa ataccctcaa ccaggtgttt gngataaaaa atgatgctaa      60
aatgaaaagg acaatgcgtg cccctgcca tctggtcgca ttagtcctgc acatgctgcg    120
atgtgggcta caagtgttgg agttgcagga acagctttgt tggcctggaa ggctaatggc    180
ttggcagctg ggcttgcagc ttctaatctt gttctgtatg catttgtgta tacgccgttg    240
aagcaaatac accctgttaa tacatgggtt ggggcagtcg ttggtgccat cccaccact     299
```

<210> SEQ ID NO 27
<211> LENGTH: 255
<212> TYPE: DNA
<213> ORGANISM: Zea sp
<220> FEATURE:
<221> NAME/KEY: misc_feature
<222> LOCATION: (1)...(255)
<223> OTHER INFORMATION: n = A,T,C or G

<400> SEQUENCE: 27

```
anacttgcat atctccatgc ntctcaggac aaagangatg acctgaaagt aggtgtcaag     60
tccacagcat taagatttgg agatttgacc nnatactgna tcagtggctt tggcgcggca   120
tgcttcggca gcttagcact cagtggttac aatgctgacc ttggttggtg tttagtgtga   180
tgcttgagcg aagaatggta tngtttttac ttgatattga ctccagacct gaaatcatgt   240
tggacagggt ggccc                                                     255
```

<210> SEQ ID NO 28
<211> LENGTH: 257
<212> TYPE: DNA
<213> ORGANISM: Zea sp

<400> SEQUENCE: 28

```
attgaagggg ataggactct ggggcttcag tcacttcctg ttgcttttgg gatggaaact     60
gcaaaatgga tttgtgttgg agcaattgat atcactcaat tatctgttgc aggttaccta   120
ttgagcaccg gtaagctgta ttatgccctg gtgttgcttg ggctaacaat tcctcaggtg   180
ttctttcagt tccagtactt cctgaaggac cctgtgaagt atgatgtcaa atatcaggca   240
agcgcacaac cattctt                                                   257
```

<210> SEQ ID NO 29
<211> LENGTH: 368
<212> TYPE: DNA
<213> ORGANISM: Zea sp

<400> SEQUENCE: 29

| | | | | | |
|---|---|---|---|---|---|
| atccagttgc | aaataataat | ggcgttcttc | tctgttgtaa | tagcactatt | caaggatata | 60 |
| cctgacatcg | aaggggaccg | catattcggg | atccgatcct | tcagcgtccg | gttagggcaa | 120 |
| aagaaggtct | tttggatctg | cgttggcttg | cttgagatgg | cctacagcgt | tgcgatactg | 180 |
| atgggagcta | cctcttcctg | tttgtggagc | aaaacagcaa | ccatcgctgg | ccattccata | 240 |
| cttgccgcga | tcctatggag | ctgcgcgcga | tcggtggact | tgacgagcaa | agccgcaata | 300 |
| acgtccttct | acatgttcat | ctggaagctg | ttctacgcgg | agtacctgct | catccctctg | 360 |
| gtgcggtg | | | | | | 368 |

<210> SEQ ID NO 30
<211> LENGTH: 122
<212> TYPE: PRT
<213> ORGANISM: Zea sp

<400> SEQUENCE: 30

Ile Gln Leu Gln Ile Ile Met Ala Phe Phe Ser Val Val Ile Ala Leu
1               5                   10                  15

Phe Lys Asp Ile Pro Asp Ile Glu Gly Asp Arg Ile Phe Gly Ile Arg
            20                  25                  30

Ser Phe Ser Val Arg Leu Gly Gln Lys Lys Val Phe Trp Ile Cys Val
        35                  40                  45

Gly Leu Leu Glu Met Ala Tyr Ser Val Ala Ile Leu Met Gly Ala Thr
    50                  55                  60

Ser Ser Cys Leu Trp Ser Lys Thr Ala Thr Ile Ala Gly His Ser Ile
65                  70                  75                  80

Leu Ala Ala Ile Leu Trp Ser Cys Ala Arg Ser Val Asp Leu Thr Ser
                85                  90                  95

Lys Ala Ala Ile Thr Ser Phe Tyr Met Phe Ile Trp Lys Leu Phe Tyr
            100                 105                 110

Ala Glu Tyr Leu Leu Ile Pro Leu Val Arg
        115                 120

<210> SEQ ID NO 31
<211> LENGTH: 278
<212> TYPE: DNA
<213> ORGANISM: Zea sp

<400> SEQUENCE: 31

| | | | | | |
|---|---|---|---|---|---|
| tattcagcac | cacctctcaa | gctcaagcag | aatggatgga | ttgggaactt | cgctctgggt | 60 |
| gcgagttaca | tcagcttgcc | ctggtgggct | ggccaggcgt | tatttggaac | tcttacacca | 120 |
| gatatcattg | tcttgactac | tttgtacagc | atagctgggc | tagggattgc | tattgtaaat | 180 |
| gatttcaaga | gtattgaagg | ggataggact | ctggggcttc | agtcacttcc | tgttgctttt | 240 |
| gggatggaaa | ctgcaaaatg | gatttgtgtt | ggagcaat | | | 278 |

<210> SEQ ID NO 32
<211> LENGTH: 292
<212> TYPE: PRT
<213> ORGANISM: Synechocystis sp

<400> SEQUENCE: 32

```
Met Val Ala Gln Thr Pro Ser Ser Pro Pro Leu Trp Leu Thr Ile Ile
  1               5                  10                  15

Tyr Leu Leu Arg Trp His Lys Pro Ala Gly Arg Leu Ile Leu Met Ile
             20                  25                  30

Pro Ala Leu Trp Ala Val Cys Leu Ala Ala Gln Gly Leu Pro Pro Leu
             35                  40                  45

Pro Leu Leu Gly Thr Ile Ala Leu Gly Thr Leu Ala Thr Ser Gly Leu
 50                  55                  60

Gly Cys Val Val Asn Asp Leu Trp Asp Arg Asp Ile Asp Pro Gln Val
 65                  70                  75                  80

Glu Arg Thr Lys Gln Arg Pro Leu Ala Ala Arg Ala Leu Ser Val Gln
             85                  90                  95

Val Gly Ile Gly Val Ala Leu Val Ala Leu Leu Cys Ala Ala Gly Leu
             100                 105                 110

Ala Phe Tyr Leu Thr Pro Leu Ser Phe Trp Leu Cys Val Ala Ala Val
             115                 120                 125

Pro Val Ile Val Ala Tyr Pro Gly Ala Lys Arg Val Phe Pro Val Pro
 130                 135                 140

Gln Leu Val Leu Ser Ile Ala Trp Gly Phe Ala Val Leu Ile Ser Trp
145                 150                 155                 160

Ser Ala Val Thr Gly Asp Leu Thr Asp Ala Thr Trp Val Leu Trp Gly
             165                 170                 175

Ala Thr Val Phe Trp Thr Leu Gly Phe Asp Thr Val Tyr Ala Met Ala
             180                 185                 190

Asp Arg Glu Asp Asp Arg Arg Ile Gly Val Asn Ser Ser Ala Leu Phe
             195                 200                 205

Phe Gly Gln Tyr Val Gly Glu Ala Val Gly Ile Phe Phe Ala Leu Thr
 210                 215                 220

Ile Gly Cys Leu Phe Tyr Leu Gly Met Ile Leu Met Leu Asn Pro Leu
225                 230                 235                 240

Tyr Trp Leu Ser Leu Ala Ile Ala Ile Val Gly Trp Val Ile Gln Tyr
             245                 250                 255

Ile Gln Leu Ser Ala Pro Thr Pro Glu Pro Lys Leu Tyr Gly Gln Ile
             260                 265                 270

Phe Gly Gln Asn Val Ile Ile Gly Phe Val Leu Leu Ala Gly Met Leu
             275                 280                 285

Leu Gly Trp Leu
    290

<210> SEQ ID NO 33
<211> LENGTH: 316
<212> TYPE: PRT
<213> ORGANISM: Synechocystis sp

<400> SEQUENCE: 33

Met Val Ser Thr Lys Ile His Arg Gln His Asp Ser Met Gly Ala
  1               5                  10                  15

Val Cys Lys Ser Tyr Tyr Gln Leu Thr Lys Pro Arg Ile Ile Pro Leu
             20                  25                  30

Leu Leu Ile Thr Thr Ala Ala Ser Met Trp Ile Ala Ser Glu Gly Arg
             35                  40                  45

Val Asp Leu Pro Lys Leu Leu Ile Thr Leu Gly Gly Thr Leu Ala
 50                  55                  60

Ala Ala Ser Ala Gln Thr Leu Asn Cys Ile Tyr Asp Gln Asp Ile Asp
 65                  70                  75                  80
```

-continued

```
Tyr Glu Met Leu Arg Thr Arg Ala Arg Pro Ile Pro Ala Gly Lys Val
                 85                  90                  95

Gln Pro Arg His Ala Leu Ile Phe Ala Leu Ala Leu Gly Val Leu Ser
            100                 105                 110

Phe Ala Leu Leu Ala Thr Phe Val Asn Val Leu Ser Gly Cys Leu Ala
        115                 120                 125

Leu Ser Gly Ile Val Phe Tyr Met Leu Val Tyr Thr His Trp Leu Lys
    130                 135                 140

Arg His Thr Ala Gln Asn Ile Val Ile Gly Gly Ala Ala Gly Ser Ile
145                 150                 155                 160

Pro Pro Leu Val Gly Trp Ala Ala Val Thr Gly Asp Leu Ser Trp Thr
                165                 170                 175

Pro Trp Val Leu Phe Ala Leu Ile Phe Leu Trp Thr Pro Pro His Phe
            180                 185                 190

Trp Ala Leu Ala Leu Met Ile Lys Asp Asp Tyr Ala Gln Val Asn Val
        195                 200                 205

Pro Met Leu Pro Val Ile Ala Gly Glu Glu Lys Thr Val Ser Gln Ile
    210                 215                 220

Trp Tyr Tyr Ser Leu Leu Val Val Pro Phe Ser Leu Leu Val Tyr
225                 230                 235                 240

Pro Leu His Gln Leu Gly Ile Leu Tyr Leu Ala Ile Ala Ile Ile Leu
                245                 250                 255

Gly Gly Gln Phe Leu Val Lys Ala Trp Gln Leu Lys Gln Ala Pro Gly
            260                 265                 270

Asp Arg Asp Leu Ala Arg Gly Leu Phe Lys Phe Ser Ile Phe Tyr Leu
        275                 280                 285

Met Leu Leu Cys Leu Ala Met Val Ile Asp Ser Leu Pro Val Thr His
    290                 295                 300

Gln Leu Val Ala Gln Met Gly Thr Leu Leu Leu Gly
305                 310                 315
```

<210> SEQ ID NO 34
<211> LENGTH: 324
<212> TYPE: PRT
<213> ORGANISM: Synechocystis sp

<400> SEQUENCE: 34

```
Met Ser Asp Thr Gln Asn Thr Gly Gln Asn Gln Ala Lys Ala Arg Gln
1               5                  10                  15

Leu Leu Gly Met Lys Gly Ala Ala Pro Gly Glu Ser Ser Ile Trp Lys
            20                  25                  30

Ile Arg Leu Gln Leu Met Lys Pro Ile Thr Trp Ile Pro Leu Ile Trp
        35                  40                  45

Gly Val Val Cys Gly Ala Ala Ser Ser Gly Gly Tyr Ile Trp Ser Val
    50                  55                  60

Glu Asp Phe Leu Lys Ala Leu Thr Cys Met Leu Leu Ser Gly Pro Leu
65                  70                  75                  80

Met Thr Gly Tyr Thr Gln Thr Leu Asn Asp Phe Tyr Asp Arg Asp Ile
                85                  90                  95

Asp Ala Ile Asn Glu Pro Tyr Arg Pro Ile Pro Ser Gly Ala Ile Ser
            100                 105                 110

Val Pro Gln Val Thr Gln Ile Leu Ile Leu Val Ala Gly Ile
        115                 120                 125

Gly Val Ala Tyr Gly Leu Asp Val Trp Ala Gln His Asp Phe Pro Ile
```

-continued

```
            130                 135                 140
Met Met Val Leu Thr Leu Gly Gly Ala Phe Val Ala Tyr Ile Tyr Ser
145                 150                 155                 160

Ala Pro Pro Leu Lys Leu Lys Gln Asn Gly Trp Leu Gly Asn Tyr Ala
                165                 170                 175

Leu Gly Ala Ser Tyr Ile Ala Leu Pro Trp Trp Ala Gly His Ala Leu
                180                 185                 190

Phe Gly Thr Leu Asn Pro Thr Ile Met Val Leu Thr Leu Ile Tyr Ser
                195                 200                 205

Leu Ala Gly Leu Gly Ile Ala Val Val Asn Asp Phe Lys Ser Val Glu
        210                 215                 220

Gly Asp Arg Gln Leu Gly Leu Lys Ser Leu Pro Val Met Phe Gly Ile
225                 230                 235                 240

Gly Thr Ala Ala Trp Ile Cys Val Ile Met Ile Asp Val Phe Gln Ala
                245                 250                 255

Gly Ile Ala Gly Tyr Leu Ile Tyr Val His Gln Gln Leu Tyr Ala Thr
                260                 265                 270

Ile Val Leu Leu Leu Ile Pro Gln Ile Thr Phe Gln Asp Met Tyr
        275                 280                 285

Phe Leu Arg Asn Pro Leu Glu Asn Asp Val Lys Tyr Gln Ala Ser Ala
        290                 295                 300

Gln Pro Phe Leu Val Phe Gly Met Leu Ala Thr Gly Leu Ala Leu Gly
305                 310                 315                 320

His Ala Gly Ile

<210> SEQ ID NO 35
<211> LENGTH: 307
<212> TYPE: PRT
<213> ORGANISM: Synechocystis sp

<400> SEQUENCE: 35

Met Thr Glu Ser Ser Pro Leu Ala Pro Ser Thr Ala Pro Ala Thr Arg
1               5                   10                  15

Lys Leu Trp Leu Ala Ala Ile Lys Pro Pro Met Tyr Thr Val Ala Val
                20                  25                  30

Val Pro Ile Thr Val Gly Ser Ala Val Ala Tyr Gly Leu Thr Gly Gln
                35                  40                  45

Trp His Gly Asp Val Phe Thr Ile Phe Leu Leu Ser Ala Ile Ala Ile
            50                  55                  60

Ile Ala Trp Ile Asn Leu Ser Asn Asp Val Phe Asp Ser Asp Thr Gly
65                  70                  75                  80

Ile Asp Val Arg Lys Ala His Ser Val Val Asn Leu Thr Gly Asn Arg
                85                  90                  95

Asn Leu Val Phe Leu Ile Ser Asn Phe Phe Leu Leu Ala Gly Val Leu
                100                 105                 110

Gly Leu Met Ser Met Ser Trp Arg Ala Gln Asp Trp Thr Val Leu Glu
            115                 120                 125

Leu Ile Gly Val Ala Ile Phe Leu Gly Tyr Thr Tyr Gln Gly Pro Pro
        130                 135                 140

Phe Arg Leu Gly Tyr Leu Gly Leu Gly Glu Leu Ile Cys Leu Ile Thr
145                 150                 155                 160

Phe Gly Pro Leu Ala Ile Ala Ala Ala Tyr Tyr Ser Gln Ser Gln Ser
                165                 170                 175

Phe Ser Trp Asn Leu Leu Thr Pro Ser Val Phe Val Gly Ile Ser Thr
```

```
                        180                 185                 190
Ala Ile Ile Leu Phe Cys Ser His Phe His Gln Val Glu Asp Asp Leu
                195                 200                 205

Ala Ala Gly Lys Lys Ser Pro Ile Val Arg Leu Gly Thr Lys Leu Gly
        210                 215                 220

Ser Gln Val Leu Thr Leu Ser Val Val Ser Leu Tyr Leu Ile Thr Ala
225                 230                 235                 240

Ile Gly Val Leu Cys His Gln Ala Pro Trp Gln Thr Leu Leu Ile Ile
                245                 250                 255

Ala Ser Leu Pro Trp Ala Val Gln Leu Ile Arg His Val Gly Gln Tyr
        260                 265                 270

His Asp Gln Pro Glu Gln Val Ser Asn Cys Lys Phe Ile Ala Val Asn
        275                 280                 285

Leu His Phe Phe Ser Gly Met Leu Met Ala Ala Gly Tyr Gly Trp Ala
        290                 295                 300

Gly Leu Gly
305
```

<210> SEQ ID NO 36
<211> LENGTH: 927
<212> TYPE: DNA
<213> ORGANISM: Synechocystis sp

<400> SEQUENCE: 36

```
atggcaacta tccaagcttt ttggcgcttc tcccgccccc ataccatcat tggtacaact    60
ctgagcgtct gggctgtgta tctgttaact attctcgggg atggaaactc agttaactcc   120
cctgcttccc tggatttagt gttcggcgct tggctggcct gcctgttggg taatgtgtac   180
attgtcggcc tcaaccaatt gtgggatgtg acattgacc gcatcaataa gccgaatttg   240
cccctagcta acggagattt ttctatcgcc cagggccgtt ggattgtggg actttgtggc   300
gttgcttcct tggcgatcgc ctggggatta gggctatggc tggggctaac ggtgggcatt   360
agtttgatta ttggcacggc ctattcggtg ccgccagtga ggttaaagcg cttttccctg   420
ctggcggccc tgtgtattct gacggtgcgg ggaattgtgg ttaacttggg cttattttta   480
ttttttagaa ttggtttagg ttatcccccc actttaataa cccccatctg ggttttgact   540
ttatttatct tagttttcac cgtggcgatc gccattttta aagatgtgcc agatatggaa   600
ggcgatcggc aatttaagat tcaaacttta actttgcaaa tcggcaaaca aaacgttttt   660
cggggaacct taatttttact cactggttgt tatttagcca tggcaatctg ggcttatgg   720
gcggctatgc ctttaaatac tgctttcttg attgtttccc atttgtgctt attagccta   780
ctctggtggc ggagtcgaga tgtacactta gaaagcaaaa ccgaaattgc tagtttttat   840
cagtttattt ggaagctatt tttcttagag tacttgctgt atcccttggc tctgtggtta   900
cctaattttt ctaatactat tttttag                                        927
```

<210> SEQ ID NO 37
<211> LENGTH: 308
<212> TYPE: PRT
<213> ORGANISM: Synechocystis sp

<400> SEQUENCE: 37

```
Met Ala Thr Ile Gln Ala Phe Trp Arg Phe Ser Arg Pro His Thr Ile
1               5                   10                  15

Ile Gly Thr Thr Leu Ser Val Trp Ala Val Tyr Leu Leu Thr Ile Leu
            20                  25                  30
```

-continued

```
Gly Asp Gly Asn Ser Val Asn Ser Pro Ala Ser Leu Asp Leu Val Phe
        35                  40                  45
Gly Ala Trp Leu Ala Cys Leu Leu Gly Asn Val Tyr Ile Val Gly Leu
 50                  55                  60
Asn Gln Leu Trp Asp Val Asp Ile Asp Arg Ile Asn Lys Pro Asn Leu
 65                  70                  75                  80
Pro Leu Ala Asn Gly Asp Phe Ser Ile Ala Gln Gly Arg Trp Ile Val
                 85                  90                  95
Gly Leu Cys Gly Val Ala Ser Leu Ala Ile Ala Trp Gly Leu Gly Leu
                100                 105                 110
Trp Leu Gly Leu Thr Val Gly Ile Ser Leu Ile Ile Gly Thr Ala Tyr
            115                 120                 125
Ser Val Pro Pro Val Arg Leu Lys Arg Phe Ser Leu Leu Ala Ala Leu
        130                 135                 140
Cys Ile Leu Thr Val Arg Gly Ile Val Val Asn Leu Gly Leu Phe Leu
145                 150                 155                 160
Phe Phe Arg Ile Gly Leu Gly Tyr Pro Pro Thr Leu Ile Thr Pro Ile
                165                 170                 175
Trp Val Leu Thr Leu Phe Ile Leu Val Phe Thr Val Ala Ile Ala Ile
            180                 185                 190
Phe Lys Asp Val Pro Asp Met Glu Gly Asp Arg Gln Phe Lys Ile Gln
        195                 200                 205
Thr Leu Thr Leu Gln Ile Gly Lys Gln Asn Val Phe Arg Gly Thr Leu
    210                 215                 220
Ile Leu Leu Thr Gly Cys Tyr Leu Ala Met Ala Ile Trp Gly Leu Trp
225                 230                 235                 240
Ala Ala Met Pro Leu Asn Thr Ala Phe Leu Ile Val Ser His Leu Cys
                245                 250                 255
Leu Leu Ala Leu Leu Trp Trp Arg Ser Arg Asp Val His Leu Glu Ser
            260                 265                 270
Lys Thr Glu Ile Ala Ser Phe Tyr Gln Phe Ile Trp Lys Leu Phe Phe
        275                 280                 285
Leu Glu Tyr Leu Leu Tyr Pro Leu Ala Leu Trp Leu Pro Asn Phe Ser
    290                 295                 300
Asn Thr Ile Phe
305
```

<210> SEQ ID NO 38
<211> LENGTH: 1092
<212> TYPE: DNA
<213> ORGANISM: Synechocystis sp

<400> SEQUENCE: 38

```
atgaaatttc cgccccacag tggttaccat tggcaaggtc aatcaccttt ctttgaaggt    60
tggtacgtgc gcctgctttt gccccaatcc ggggaaagtt ttgcttttat gtactccatc   120
gaaaatcctg ctagcgatca tcattacggc ggcggtgctg tgcaaatttt agggccggct   180
acgaaaaaac aagaaaatca ggaagaccaa cttgtttggc ggacatttcc ctcggtaaaa   240
aaattttggg ccagtcctcg ccagtttgcc ctagggcatt ggggaaaatg tagggataac   300
aggcaggcga accccctact ctccgaagaa ttttttgcca cggtcaagga aggttatcaa   360
atccatcaaa atcagcacca aggacaaatc attcatggcg atcgccattg tcgttggcag   420
ttcaccgtag aaccggaagt aacttggggg agtcctaacc gatttcctcg ggctacagcg   480
```

-continued

```
ggttggcttt ccttttacc cttgtttgat cccggttggc aaattctttt agcccaaggt      540
agagcgcacg gctggctgaa atggcagagg aacagtatg aatttgacca cgccctagtt      600
tatgccgaaa aaaattgggg tcactccttt ccctcccgct ggttttggct ccaagcaaat      660
tattttcctg accatccagg actgagcgtc actgccgctg gcggggaacg gattgttctt      720
ggtcgccccg aagaggtagc tttaattggc ttacatcacc aaggtaattt ttacgaattt      780
ggcccgggcc atggcacagt cacttggcaa gtagctccct ggggccgttg gcaattaaaa      840
gccagcaatg ataggtattg ggtcaagttg tccggaaaaa cagataaaaa aggcagttta      900
gtccacactc ccaccgccca gggcttacaa ctcaactgcc gagataccac tagggctat       960 ttgtatttgc aattgggatc tgtgggtcac ggcctgatag tgcaagggga aacggacacc     1020
gcggggctag aagttggagg tgattgggt ttaacagagg aaaatttgag caaaaaaaca     1080
gtgccattct ga                                                          1092
```

<210> SEQ ID NO 39
<211> LENGTH: 363
<212> TYPE: PRT
<213> ORGANISM: Synechocystis sp

<400> SEQUENCE: 39

```
Met Lys Phe Pro Pro His Ser Gly Tyr His Trp Gln Gly Gln Ser Pro
  1               5                  10                  15

Phe Phe Glu Gly Trp Tyr Val Arg Leu Leu Pro Gln Ser Gly Glu
             20                  25                  30

Ser Phe Ala Phe Met Tyr Ser Ile Glu Asn Pro Ala Ser Asp His His
         35                  40                  45

Tyr Gly Gly Ala Val Gln Ile Leu Gly Pro Ala Thr Lys Lys Gln
     50                  55                  60

Glu Asn Gln Glu Asp Gln Leu Val Trp Arg Thr Phe Pro Ser Val Lys
 65                  70                  75                  80

Lys Phe Trp Ala Ser Pro Arg Gln Phe Ala Leu Gly His Trp Gly Lys
                 85                  90                  95

Cys Arg Asp Asn Arg Gln Ala Lys Pro Leu Leu Ser Glu Glu Phe Phe
            100                 105                 110

Ala Thr Val Lys Glu Gly Tyr Gln Ile His Gln Asn Gln His Gln Gly
        115                 120                 125

Gln Ile Ile His Gly Asp Arg His Cys Arg Trp Gln Phe Thr Val Glu
    130                 135                 140

Pro Glu Val Thr Trp Gly Ser Pro Asn Arg Phe Pro Arg Ala Thr Ala
145                 150                 155                 160

Gly Trp Leu Ser Phe Leu Pro Leu Phe Asp Pro Gly Trp Gln Ile Leu
                165                 170                 175

Leu Ala Gln Gly Arg Ala His Gly Trp Leu Lys Trp Gln Arg Glu Gln
            180                 185                 190

Tyr Glu Phe Asp His Ala Leu Val Tyr Ala Glu Lys Asn Trp Gly His
        195                 200                 205

Ser Phe Pro Ser Arg Trp Phe Trp Leu Gln Ala Asn Tyr Phe Pro Asp
    210                 215                 220

His Pro Gly Leu Ser Val Thr Ala Ala Gly Gly Glu Arg Ile Val Leu
225                 230                 235                 240

Gly Arg Pro Glu Glu Val Ala Leu Ile Gly Leu His His Gln Gly Asn
                245                 250                 255

Phe Tyr Glu Phe Gly Pro Gly His Gly Thr Val Thr Trp Gln Val Ala
```

```
            260                265                270
Pro Trp Gly Arg Trp Gln Leu Lys Ala Ser Asn Asp Arg Tyr Trp Val
        275                280                285

Lys Leu Ser Gly Lys Thr Asp Lys Lys Gly Ser Leu Val His Thr Pro
    290                295                300

Thr Ala Gln Gly Leu Gln Leu Asn Cys Arg Asp Thr Thr Arg Gly Tyr
305                310                315                320

Leu Tyr Leu Gln Leu Gly Ser Val Gly His Gly Leu Ile Val Gln Gly
                325                330                335

Glu Thr Asp Thr Ala Gly Leu Glu Val Gly Gly Asp Trp Gly Leu Thr
                340                345                350

Glu Glu Asn Leu Ser Lys Lys Thr Val Pro Phe
            355                360

<210> SEQ ID NO 40
<211> LENGTH: 56
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 40
cgcgatttaa atggcgcgcc ctgcaggcgg ccgcctgcag ggcgcgccat ttaaat          56

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 41
tcgaggatcc gcggccgcaa gcttcctgca gg                                   32

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 42
tcgacctgca ggaagcttgc ggccgcggat cc                                   32

<210> SEQ ID NO 43
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 43
tcgacctgca ggaagcttgc ggccgcggat cc                                   32

<210> SEQ ID NO 44
<211> LENGTH: 32
<212> TYPE: DNA
<213> ORGANISM: Artificial Sequence
<220> FEATURE:
<223> OTHER INFORMATION: Description of Artificial Sequence:
```

```
                                  Oligonucleotide

<400> SEQUENCE: 44
tcgaggatcc gcggccgcaa gcttcctgca gg                                32

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 45
tcgaggatcc gcggccgcaa gcttcctgca ggagct                            36

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 46
cctgcaggaa gcttgcggcc gcggatcc                                     28

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 47
tcgacctgca ggaagcttgc ggccgcggat ccagct                            36

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 48
ggatccgcgg ccgcaagctt cctgcagg                                     28

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 49
gatcacctgc aggaagcttg cggccgcgga tccaatgca                         39

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide
```

<400> SEQUENCE: 50
ttggatccgc ggccgcaagc ttcctgcagg t					31

<210> SEQ ID NO 51
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 51
ggatccgcgg ccgcacaatg gagtctctgc tctctagttc t					41

<210> SEQ ID NO 52
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 52
ggatcctgca ggtcacttca aaaaggtaa cagcaagt					38

<210> SEQ ID NO 53
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 53
ggatccgcgg ccgcacaatg gcgtttttg ggctctcccg tgttt					45

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 54
ggatcctgca ggttattgaa aacttcttcc aagtacaact					40

<210> SEQ ID NO 55
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 55
ggatccgcgg ccgcacaatg tggcgaagat ctgttgtt					38

<210> SEQ ID NO 56
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide

```
<400> SEQUENCE: 56
ggatcctgca ggtcatggag agtagaagga aggagct                                37

<210> SEQ ID NO 57
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 57
ggatccgcgg ccgcacaatg gtacttgccg aggttccaaa gcttgcctct                  50

<210> SEQ ID NO 58
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 58
ggatcctgca ggtcacttgt ttctggtgat gactctat                               38

<210> SEQ ID NO 59
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 59
ggatccgcgg ccgcacaatg acttcgattc tcaacact                               38

<210> SEQ ID NO 60
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 60
ggatcctgca ggtcagtgtt gcgatgctaa tgccgt                                 36

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 61
taatgtgtac attgtcggcc tc                                                22

<210> SEQ ID NO 62
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 62
```
gcaatgtaac atcagagatt ttgagacaca acgtggcttt ccacaattcc ccgcaccgtc      60

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 63
aggctaataa gcacaaatgg ga                                              22

<210> SEQ ID NO 64
<211> LENGTH: 63
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 64
ggtatgagtc agcaacacct tcttcacgag gcagacctca gcggaattgg tttaggttat     60
ccc                                                                   63

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 65
ggatccatgg ttgcccaaac cccatc                                          26

<210> SEQ ID NO 66
<211> LENGTH: 61
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 66
gcaatgtaac atcagagatt ttgagacaca acgtggcttt gggtaagcaa caatgaccgg     60
c                                                                     61

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 67
gaattctcaa agccagccca gtaac                                           25

<210> SEQ ID NO 68
<211> LENGTH: 63
<212> TYPE: DNA
<213> ORGANISM: Artificial Sequence
<220> FEATURE:
<223> OTHER INFORMATION: Description of Artificial Sequence:

-continued

Oligonucleotide

<400> SEQUENCE: 68
ggtatgagtc agcaacacct tcttcacgag gcagacctca gcgggtgcga aaagggtttt      60
ccc                                                                   63

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 69
ccagtggttt aggctgtgtg gtc                                             23

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 70
ctgagttgga tgtattggat c                                               21

<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 71
ggatccatgg ttacttcgac aaaaatcc                                        28

<210> SEQ ID NO 72
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 72
gcaatgtaac atcagagatt ttgagacaca acgtggcttt gctaggcaac cgcttagtac      60

<210> SEQ ID NO 73
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 73
gaattcttaa cccaacagta aagttccc                                        28

<210> SEQ ID NO 74
<211> LENGTH: 63
<212> TYPE: DNA
<213> ORGANISM: Artificial Sequence
<220> FEATURE:

<223> OTHER INFORMATION: Description of Artificial Sequence:
      Oligonucleotide

<400> SEQUENCE: 74
ggtatgagtc agcaacacct tcttcacgag gcagacctca gcgccggcat tgtcttttac    60
atg                                                                  63

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 75 ggaaccctttg cagccgcttc                                                20

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 76
gtatgcccaa ctggtgcaga gg                                              22

<210> SEQ ID NO 77
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 77
ggatccatgt ctgacacaca aaataccg                                        28

<210> SEQ ID NO 78
<211> LENGTH: 62
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 78
gcaatgtaac atcagagatt ttgagacaca acgtggcttt cgccaatacc agccaccaac    60
ag                                                                   62

<210> SEQ ID NO 79
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 79
gaattctcaa atccccgcat ggcctag                                         27

<210> SEQ ID NO 80
<211> LENGTH: 65

```
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 80
ggtatgagtc agcaacacct tcttcacgag gcagacctca gcggcctacg gcttggacgt    60
gtggg                                                                65

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 81
cacttggatt ccctgatct g                                               21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 82
gcaatacccg cttggaaaac g                                              21

<210> SEQ ID NO 83
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 83
ggatccatga ccgaatcttc gcccctagc                                      29

<210> SEQ ID NO 84
<211> LENGTH: 61
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 84
gcaatgtaac atcagagatt ttgagacaca acgtggcttt caatcctagg tagccgaggc    60
g                                                                    61

<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 85
gaattcttag cccaggccag cccagcc                                        27
```

```
<210> SEQ ID NO 86
<211> LENGTH: 66
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 86
ggtatgagtc agcaacacct tcttcacgag gcagacctca gcggggaatt gatttgttta    60
attacc                                                                66

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 87
gcgatcgcca ttatcgcttg g                                               21

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 88
gcagactggc aattatcagt aacg                                            24

<210> SEQ ID NO 89
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 89
ccatggattc gagtaaagtt gtcgc                                           25

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 90
gaattcactt caaaaaaggt aacag                                           25

<210> SEQ ID NO 91
<211> LENGTH: 4550
<212> TYPE: DNA
<213> ORGANISM: Arabidopsis sp

<400> SEQUENCE: 91
attttacacc aatttgatca cttaactaaa ttaattaaat tagatgatta tcccaccata     60
tttttgagca ttaaaccata aaaccatagt tataagtaac tgttttaatc gaatatgact    120
```

-continued

```
cgattaagat taggaaaaat ttataaccgg taattaagaa acattaacc gtagtaaccg    180 taaatgccga ttcctcccctt gtctaaaaga cagaaaacat atattttatt ttgccccata   240
tgtttcactc tatttaattt caggcacaat acttttggtt ggtaacaaaa ctaaaaagga   300
caacacgtga tacttttcct cgtccgtcag tcagattttt tttaaactag aaacaagtgg   360
caaatctaca ccacattttt tgcttaatct attaacttgt aagttttaaa ttcctaaaaa   420
agtctaacta attcttctaa tataagtaca ttccctaaat ttcccaaaaa gtcaaattaa   480 taatttcaa aatctaatct aaatatctaa taattcaaaa tcattaaaaa gacacgcaac    540
aatgacacca attaatcatc ctcgacccac acaattctac agttctcatg ctaaaccata   600
ttttttgctc tctgttcctt caaaatcatt tctttctctt ctttgattcc caagatcac    660 ttctttgtct ttgatttttg attttttttc tctctggcgt gaaggaagaa gctttatttc   720
atggagtctc tgctctctag ttcttctctt gtttccgctg gtaaatctcg tcctttttctg   780 gtttcaggtt ttatttgttg tttaggtttc gttttttgtga ttcagaacca tacaaaaagt   840
ttgaactttt ctgaatataa aataaggaaa aagtttcgat ttttataatg aattgtttac   900
tagatcgaag taggtgacaa aggttattgt gtggagaagc ataatttctg ggcttgactt   960
tgaattttgt ttctcatgca tgcaactttat caatcagctg gtgggttttg ttggaagaag  1020
cagaatctaa agctccactc tttatcaggt tcgttagggt tttatgggtt tttgaaatta   1080
aatactcaat catcctagtc tcattattct attggttgaa tcacattttc taatttggaa   1140
tttatgagac aatgtatgtt ggacttagtt gaagttcttc tctttggtta tagttgaagt   1200
gttactgatg ttgtttagct ctttacacca atatatacac ccaattttgc agaaatccga   1260
gttctgcgtt gtgattcgag taaagttgtc gcaaaaccga agtttaggaa caatcttgtt   1320
aggcctgatg gtcaaggatc ttcattgttg ttgtatccaa acataagtc gagatttcgg    1380 gttaatgcca ctgcgggtca gcctgaggct ttcgactcga atagcaaaca gaagtctttt   1440
agagactcgt tagatgcgtt ttacaggttt tctaggcctc atacagttat tggcacagtt   1500
aagtttctct ttaaaaatgt aactcttta aaacgcaatc tttcagggtt ttcaaggaga   1560
taacattagc tctgtgattg gatttgcagg tgcttagcat tttatctgta tctttcttag   1620
cagtagagaa ggtttctgat atatctcctt tacttttcac tggcatcttg gaggtaatga   1680
atatataaca cataatgacc gatgaagaag atacattttt ttcgtctctc tgttaaaaca   1740
attgggtttt gttttcaggc tgttgttgca gctctcatga tgaacattta catagttggg   1800
ctaaatcagt tgtctgatgt tgaaatagat aaggtaacat gcaaattttc ttcatatgag   1860
ttcgagagac tgatgagatt aatagcagct agtgcctaga tcatctctat gtgggttttt   1920
gcaggttaac aagccctatc ttccattggc atcaggagaa tattctgtta acaccggcat   1980
tgcaatagta gcttccttct ccatcatggt atggtgccat tttcacaaaa tttcaacttt   2040
tagaattcta taagttactg aaatagtttg ttataaatcg ttatagagtt tctggcttgg   2100
gtggattgtt ggttcatggc cattgttctg ggctcttttt gtgagtttca tgctcggtac   2160
tgcatactct atcaatgtaa gtaagtttct caatactaga atttggctca atcaaaatc    2220 tgcagttct agtttaggt taatgaggtt ttaataactt acttcactat caaacagttg    2280
ccacttttac ggtggaaaag atttgcattg gttgcagcaa tgtgtatcct cgctgtccga   2340
gctattattg ttcaaatcgc cttttatcta catattcagg tactaaacca ttttccttat   2400
gttttgtagt tgttttcatc aaaatcactt ttatattact aaagctgtga aactttgttg   2460
cagacacatg tgtttggaag accaatcttg ttcactaggc ctcttatttt cgccactgcg   2520
```

-continued

```
tttatgagct ttttctctgt cgttattgca ttgtttaagg taaacaaaga tggaaaaaga      2580
ttaaatctat gtatacttaa agtaaagcat tctactgtta ttgatgagaa gttttctttt      2640
ttggttggat gcaggatata cctgatatcg aagggggataa gatattcgga atccgatcat     2700
tctctgtaac tctgggtcag aaacgggtac gatatctaaa ctaaagaaat tgttttgact      2760
caagtgttgg attaagatta cagaagaaag aaaactgttt ttgtttcttg caaaattcag      2820
gtgttttgga catgtgttac actacttcaa atggcttacg ctgttgcaat tctagttgga      2880
gccacatctc cattcatatg gagcaaagtc atctcggtaa caatctttct ttacccatcg      2940
aaaactcgct aattcatcgt ttgagtggta ctggtttcat tttgttccgt tctgttgatt      3000
ttttttcagg ttgtgggtca tgttatactc gcaacaactt tgtgggctcg agctaagtcc      3060
gttgatctga gtagcaaaac cgaaataact tcatgttata tgttcatatg gaaggttaga      3120
ttcgtttata aatagagtct ttactgcctt tttatgcgct ccaatttgga attaaaatag      3180
cctttcagtt tcatcgaatc accattatac tgataaattc tcatttctgc atcagctctt      3240
ttatgcagag tacttgctgt taccttttt gaagtgactg acattagaag agaagaagat       3300
ggagataaaa gaataagtca tcactatgct tctgtttta ttacaagttc atgaaattag        3360
gtagtgaact agtgaattag agttttattc tgaaacatgg cagactgcaa aaatatgtca      3420
aagatatgaa tttctgttgg gtaaagaagt ctctgcttgg gcaaaatctt aaggttcggt      3480
gtgttgatat aatgctaagc gaagaaatcg attctatgta gaaatttccg aaactatgtg      3540
taaacatgtc agaacatctc cattctatat cttcttctgc aagaaagctc tgtttttatc      3600
acctaaactc tttatctctg tgtagttaag atatgtatat gtacgtgact acatttttt       3660 gttgatgtaa tttgcagaac gtatggattt tgttagaaa gcatgagttc gaaagtatat        3720
gtttatatat atggataatt cagacctaac gtcgaagctc acaagcataa attcactact      3780
atagtttgct ctgtaataga tagttccatt gatgtcttga aactgtacgt aactgcctgg      3840
gcgttttgtg gttgatactg actactgagt gttcttttgtg agtgttgtaa gtatacaaga    3900
agaagaatat aggctcacgg gaacgactgt ggtggaagat gaaatggaga tcatcacgta     3960
gcggctttgc caaagaccga gtcacgatcg agtctatgaa gtctttacag ctgctgatta      4020
tgattgacca ttgcttagag acgcattgga atcttactag ggacttgcct gggagtttct      4080
tcaagtacgt gtcagatcat acgatgtagg agatttcacg gctttgatgt gtttgtttgg     4140
agtcacaatg cttaatgggc ttattggccc aataatagct agctctttg ctttagccgt      4200 ttcgtttgtc ccctggtggt gagtattatt agggtatggt gtgaccaaag tcaccagacc     4260
tagagtgaat ctagtagagt cctagaccat ggtccatggc ttttatttgt aatttgaaaa     4320
atgaacaatt cttttttgtaa ggaaaacttt tatatagtag acgtttacta tatagaaact   4380
agttgaacta acttcgtgca attgcataat aatggtgtga aatagagggt gcaaaactca      4440
ataacatttt cgacgtacca agagttcgaa acaataagca aaatagattt ttttgcttca     4500
gactaatttg tacaatgaat ggttaataaa ccattgaagc ttttattaat                 4550
```

<210> SEQ ID NO 92
<211> LENGTH: 4450
<212> TYPE: DNA
<213> ORGANISM: Arabidopsis sp

<400> SEQUENCE: 92

```
tttaggttac aaaatcaatg atattgcgta tgtcaactat aaaagccaaa agtaaagcct        60
```

-continued

| | |
|---|---|
| cttgtttgac cagaaggtca tgatcattgt atacatacag ccaaactacc tcctggaaga | 120 |
| aaagacatgg atcccaaaca caacaatag cttcttttac aagaaccagt agtaactagt | 180 |
| cactaatcta aaagagttaa gtttcagctt ttctggcaat ggctccttga tcatttcaat | 240 |
| cctgaaggag acccactttg tagcaagacc atgtcctctg tttcacttac agtgtgtctc | 300 |
| aaaagtctac ttcaattctt catatatagg ttcctcacac tacagcttca tcctcattcg | 360 |
| ttgacagaga gagagtcttt attgaaaact tcttccaagt acaactccac taaatataat | 420 |
| agcaccaaac cacttgttcg acacaaatct gtacagatat aaaaacacta ttaggttttc | 480 |
| caaggcaaat cacataattg gattgtgaaa gagtacaaaa gataaaccca aattttcata | 540 |
| ctttctactg cagtcagcac cagatgataa gtcagctgtc cctatttgcc atcctaactg | 600 |
| tcctgatgca gcggccagtg atgcgtaata ttgccaccct taatcattag agcgagaaac | 660 |
| aaaaagaatc aaaagacagt aaatggaatt aggaatcaca aatgagtcct tgtaaagttt | 720 |
| attgagtacc gagatctgca ctgaatccag aaagtgcaag aaaacctatg gatgctgtgc | 780 |
| caaatccagt taaccaaagc tttgtattat caccgaatct aagggctgtt gacttaacac | 840 |
| caactttttac atcatcttct ttgtcctgga gacacaatat attagacatt agtccatgga | 900 |
| aaaaaaatga tttaacctag aatatctcaa aattacttgc ataaaaactg aacttgagct | 960 |
| gaaattttgg gttcgtagct tgtggcatat actatttcat tttcaatggg ccacaaaggt | 1020 |
| aactttcttt tctcacttct gttgcaaacg ggaagacttt tatggggcta actcttcact | 1080 |
| taaagtatag aaatcagatg gaaaggtgg gagatcaggg taattttctt ctttatgatt | 1140 |
| gacaaaagtc gaacatcgaa atggatgcat ttgcatgaga catgaaacaa aagctgaaaa | 1200 |
| agaaatctgt ggtggtgaag ctagaaaaag aaaacaaagc aagcaatatg cacacattga | 1260 |
| gattaactac tttgctactg gtcataatca aatagatttt gaagctaaaa ataaaaagt | 1320 |
| gaatatacct gatgtgcata aatagtatca taaacaaggg tccagcagac tccggagaga | 1380 |
| tagagaggga gtacaataga tggtgctatg cttccttaa ctgcagtcca tcctaacaat | 1440 |
| gctccccagt ttatggtcaa acctaaaaag gcttgaggct gcaattataa aaacgaatca | 1500 |
| atcataagaa aatcagaaaa tatataatgt ctaactttga aagccagaa tagatttaaa | 1560 |
| ttacccaaaa tgtaaacctc ttcataagtg ggtaggaaaa gacaagtaac aaagatgaag | 1620 |
| cccctaaaac acggctgcag aatatacata ctgaaatgag ctcaagtaga aaagaatttg | 1680 |
| atcacaaaac taaagacaag acctgagaac atatcttcag aatttgggcc aactacataa | 1740 |
| gggtgaacca tatgtgtatg tgaattttta acaaacact tgcaaatacg cgactttagg | 1800 |
| gcaagtaaaa aatccaaaca aacctgtaat tgttaagttg gagaagaatc cctaagccta | 1860 |
| aaagcaactg cagcccgaga atccaatcc cttgaaatgg tgtcaaaaga ccactggcga | 1920 |
| taggtcttag ttttgtacga tcaacctgga tataaaagaa atttgtaaga caacataatc | 1980 |
| taaaacaaaa caaccataca aaatcttgag ctttacatac aagcaaccca tctttgttta | 2040 |
| tggaagaatg aatccagtta catgaatgct gtgtatctac cctaactact aaacacatat | 2100 |
| ttcaatcgaa aaacatattc caccttcacc atatctaaca cctgaagtct ttcactttt | 2160 |
| gaacgaagtc atcagaacat gcagataagc tattacccaa aacagagata tgactggaaa | 2220 |
| tgttgtcgta aattgatcca acatagaaaa atcaagacca gttccagatg tcaaagcaat | 2280 |
| aacactttcc caccatggtt acagaaacca tagttacaca aaacatgttt cctaaaccaa | 2340 |
| catactaaag ggatatataa atttgacatc actttatcac cataccataa gatagcttaa | 2400 |
| aaacaaactg acctttgtat ctatgtcctg atcaagcaga tcatttatag tacaaccagc | 2460 |

```
acctctaaga agtaatgctc cgcaaccaaa taaagccata tatttaaaac ttggaaggct      2520
tccaggatca gcagccaacg caatcgacct atacaacaat gatggagatt cagagtatcg      2580
atctatttac atagctctgg aactagatcc atgacgaaac atggaacatc gttataatat      2640
ctaaagactt ccaaacagat tcctgagtaa gaaacccagt ggaactatag tactgtaaca      2700
tatataaaat caaagaaaac tcaggtttat agcattatcc aatcctgatt tctgccaatc      2760
cttaaccact ctcccatgct atcaaaaacc tcagctcaag atcatactac ctaattgcct      2820
atgagctctt gggaagatca ttatggattt gataactgaa aaaagtaaca gagaaatagc      2880
agactgcaag aactactcca aacttctcca ctgatatgta tgtagtctaa caataataaa      2940
cagacataaa ttcttttatc aagcttcaag agcaagttag tcagaaaaca tcacagccaa      3000
accaaccagg aaaacacata actttatcac ataaaactaa atttaatgta atctgactta      3060
acataaacca tcctttggga cgaaaggaaa ctatataaac atgcagtctt tctttccctc      3120
agctattctt tcggatggat tataatgaat ctcaaaagtg aaatgtcttg attctcagct      3180
acattactca aaggcgaaga taaacttacc acatacaagg ccacgcaagc aaccaagttc      3240
caatgggttt atccaatcga gcaagcttag cataacctct aacttcttct ggtaaataca      3300
aatctatcca agaagcttcc ttaacaacaa caccatcact cttctcctta tcatctttct      3360
tcggctttcc ctccaaaacc gaagaagacg acgacattcc acaaattaat ctgtaattcc      3420
aaccaacacc aaaaaacttc tcctgatgca attctcttcc tttactccat acttggtaat      3480
tatcattcca tgaaggataa cacttagtga aaggatttgt gtaatgggta gtcacaggat      3540
tggacaagga tttatgttgt gattgcaaaa gagcagagga agaagatgga gttacggaga      3600
cggaagattt caacaaccgt cttgaaacac gggagagccc aaaaaacgcc atctttgaga      3660
gaaattgttg cctggaagaa acaaagactt gagatttcaa acgtaagtga attcttacga      3720
acgaaagcta acttctcaag agaatcagat tagtgattcc tcaaaaacaa acaaaactat      3780
ctaatttcag tttcgagtga tgaagcctta agaatctaga acctccatgg cgtttctaat      3840
ctctcagaga taatcgaatt ccttaaacaa tcaaagctta gaaagagaag aacaacaaca      3900
acaacaaaaa aaatcagatt aacaaccgac cagagagcaa cgacgacgcc ggcgagaaag      3960
agcacgtcgt ctcggagcaa gacttcttct ccagtaaccc ggatggatcg ttaatgggcc      4020
tgtagattat tatatttggg ccgaaacaat tgggtcagca aaaacttggg ggataatgaa      4080
gaaacacgta cagtatgcat ttaggctcca aattaattgg ccatataatt cgaatcagat      4140
aaactaatca acccctacct tacttatttc tcactgtttt tatttctacc ttagtagttg      4200
aagaaacact tttatttatc ttttcgggac ccaaatttga taggatcggg ccattactca      4260
tgagcgtcag acacatatta gccttatcag attagtgggg taaggttttt ttaattcggt      4320
aagaagcaac aatcaatgtc ggagaaatta agaatctgc atgggcgtgg cgtgatgata      4380
tgtgcatatg gagtcagttg ccgatcatat ataactattt ataaactaca tataaagact      4440
actaatagat                                                             4450

<210> SEQ ID NO 93
<211> LENGTH: 2850
<212> TYPE: DNA
<213> ORGANISM: Arabidopsis sp

<400> SEQUENCE: 93
aattaaaatt tgagcggtct aaaccattag accgtttaga gatccctcca acccaaaata       60
```

-continued

| | | | | |
|---|---|---|---|---|
| gtcgattttc | acgtcttgaa | catatattgg | gccttaatct | gtgtggttag taaagactttt | 120 |
| tattggtcaa | agaaaaacaa | ccatggccca | acatgttgat | acttttatttt aattatacaa | 180 |
| gtacccctga | attctctgaa | atatatttga | ttgacccaga | tattaatttt aattatcatt | 240 |
| tcctgtaaaa | gtgaaggagt | caccgtgact | cgtcgtaatc | tgaaaccaat ctgttcatat | 300 |
| gatgaagaag | tttctctcgt | tctcctccaa | cgcgtagaaa | attctgacgg cttaacgatg | 360 |
| tggcgaagat | ctgttgttta | tcgtttctct | tcaagaatct | ctgtttcttc ttcgttacca | 420 |
| aaccctagac | tgattccttg | gtcccgcgaa | ttatgtgccg | ttaatagctt ctcccagcct | 480 |
| ccggtctcga | cggaatcaac | tgctaagtta | gggatcactg | gtgttagatc tgatgccaat | 540 |
| cgagttttg | ccactgctac | tgccgccgct | acagctacag | ctaccaccgg tgagatttcg | 600 |
| tctagagttg | cggctttggc | tggattaggg | catcactacg | ctcgttgtta ttgggagctt | 660 |
| tctaaagcta | aacttaggta | tgtgtttact | tttcttttct | catgaaaaat ctgaaaattt | 720 |
| ccaattgttg | gattcttaaa | ttctcatttg | ttttatggtt | gtagtatgct tgtggttgca | 780 |
| acttctggaa | ctgggtatat | tctgggtacg | ggaaatgctg | caattagctt cccgggggctt | 840 |
| tgttacacat | gtgcaggaac | catgatgatt | gctgcatctg | ctaattcctt gaatcaggtc | 900 |
| attgaaatgt | tgagaagttc | ataaatttcg | aatccttgtt | gtgtttatgt agttgatctt | 960 |
| gcttgcttat | gtttatgtag | ttgaaaagtt | taaaaatttc | taatccttgg tagttgatct | 1020 |
| cgcttgtttg | tttttcatt | ttctagattt | ttgagataag | caatgattct aagatgaaaa | 1080 |
| gaacgatgct | aaggccattg | ccttcaggac | gtattagtgt | tccacacgct gttgcatggg | 1140 |
| ctactattgc | tggtgcttct | ggtgcttgtt | tgttggccag | caaggtgaat gtttgttttt | 1200 |
| ttatatgtga | tttctttgtt | ttatgaatgg | gtgattgaga | gattatggat ctaaactttt | 1260 |
| gcttccacga | caaggttatt | gcagactaat | atgttggctg | ctggacttgc atctgccaat | 1320 |
| cttgtactttt | atgcgtttgt | ttatactccg | ttgaagcaac | ttcaccctat caatacatgg | 1380 |
| gttggcgctg | ttgttggtgc | tatcccaccc | ttgcttgggt | aaatttttgt tccttttctt | 1440 |
| ctttattta | gcagattctg | ttttgttgga | tactgctttt | aattcaaaat gtagtcatgg | 1500 |
| ttcaccaatt | ctatgcttat | ctatttttgtg | tgttgtcagg | tgggcggcag cgtctggtca | 1560 |
| gatttcatac | aattcgatga | ttcttccagc | tgctctttac | ttttggcaga tacctcatttt | 1620 |
| tatggccctt | gcacatctct | gccgcaatga | ttatgcagct | ggagggtaag accatatggt | 1680 |
| gtcatatgag | attagaatgt | ctccttccat | gtagtgttga | tcttgaacta gttcaatttc | 1740 |
| gtggaatgat | cagagtgtcc | tagatagtgt | cacagcagtc | gacattttag tggctagata | 1800 |
| atgagttctt | tccgttagag | ataaacattc | gcgaacattg | tttccagctt ccgcgaccca | 1860 |
| acttctgatt | ttgtttcttg | gtaccttgtt | ttcagttaca | agatgttgtc actctttgat | 1920 |
| ccgtcaggga | agagaatagc | agcagtggct | ctaaggaact | gcttttacat gatccctctc | 1980 |
| ggtttcatcg | cctatgactg | tgagtcttgt | agattcatct | ttttttttgta gtttattgac | 2040 |
| tgcattgctg | tatctgattt | ttgctgttcc | ttccaatttt | tgtgacaggg gggttaacct | 2100 |
| caagttggtt | ttgcctcgaa | tcaacacttc | tcacactagc | aatcgctgca acagcatttt | 2160 |
| cattctaccg | agaccggacc | atgcataaag | caaggaaaat | gttccatgcc agtcttctct | 2220 |
| tccttcctgt | tttcatgtct | ggtcttcttc | tacaccgtgt | ctctaatgat aatcagcaac | 2280 |
| aactcgtaga | agaagccgga | ttaacaaatt | ctgtatctgg | tgaagtcaaa actcagaggc | 2340 |
| gaaagaaacg | tgtggctcaa | cctccggtgg | cttatgcctc | tgctgcaccg tttcctttcc | 2400 |
| tcccagctcc | ttccttctac | tctccatgat | aacctttaag | caagctattg aattttttgga | 2460 |

-continued

| aacagaaatt | aaaaaaaaaa | tctgaaaagt | tcttaagttt | aatctttggt | taataatgaa | 2520 |
| gtggagaacg | catacaagtt | tatgtatttt | ttctcatctc | cacataattg | tatttttttct | 2580 |
| ctaagtatgt | ttcaaatgat | acaaaataca | tactttatca | attatctgat | caaattgatg | 2640 |
| aattttttgag | ctttgacgtg | ttaggtctat | ctaataaacg | tagtaacgaa | tttggttttg | 2700 |
| gaaatgaaat | ccgataaccg | atgatggtgt | agagttaaac | gattaaaccg | ggttggttaa | 2760 |
| aggtctcgag | tctcgacggc | tgcggaaatc | ggaaaatcac | gattgaggac | tttgagctgc | 2820 |
| cacgaagatg | gcgatgaggt | tgaaatcaat | | | | 2850 |

<210> SEQ ID NO 94
<211> LENGTH: 3660
<212> TYPE: DNA
<213> ORGANISM: Arabidopsis sp

<400> SEQUENCE: 94

| tatttgtatt | tttattgtta | aattttatga | tttcacccgg | tatatatcat | cccatattaa | 60 |
| tattagattt | attttttggg | ctttatttgg | gttttcgatt | taaactgggc | ccattctgct | 120 |
| tcaatgaaac | cctaatgggt | tttgtttggg | cttttggattt | aaaccgggcc | cattctgctt | 180 |
| caatgaaggt | cctttgtcca | acaaaactaa | catccgacac | aactagtatt | gccaagagga | 240 |
| tcgtgccaca | tggcagttat | tgaatcaaag | gccgccaaaa | ctgtaacgta | gacattactt | 300 |
| atctccggta | acggacaacc | actcgtttcc | cgaaacagca | actcacagac | tcacaccact | 360 |
| ccagtctccg | gcttaactac | caccagagac | gattctctct | tccgtcggtt | ctatgacttc | 420 |
| gattctcaac | actgtctcca | ccatccactc | ttccagagtt | acctccgtcg | atcgagtcgg | 480 |
| agtcctctct | cttcggaatt | cggattccgt | tgagttcact | cgccggcgtt | ctggtttctc | 540 |
| gacgttgatc | tacgaatcac | ccggtagtta | gcattctgtt | ggatagattg | atgaatgttt | 600 |
| tcttcgattt | tttttttttact | gatcttgttg | tggatctctc | gtagggcgga | gatttgttgt | 660 |
| gcgtgcggcg | gagactgata | ctgataaagg | tatgattttt | tagttgtttt | tattttctct | 720 |
| ctcttcaaaa | ttctcttttc | aaacactgtg | gcgtttgaat | ttccgacggc | agttaaatct | 780 |
| cagacacctg | acaaggcacc | agccggtggt | tcaagcatta | accagcttct | cggtatcaaa | 840 |
| ggagcatctc | aagaaactgt | aattttgttc | atctcctcag | aatcttttaa | attatcatat | 900 |
| ttgtggataa | tgatgtgtta | gtttaggaat | tttcctacta | aaggtaatct | cttttgagga | 960 |
| caagtcttgt | ttttagctta | gaaatgatgt | gaaaatgttg | tttgttagct | aaaaagagtt | 1020 |
| tgttgttata | ttctgtattc | agaataaatg | gaagattcgt | cttcagctta | caaaaccagt | 1080 |
| cacttggcct | ccactggttt | ggggagtcgt | ctgtggtgct | gctgcttcag | gtaatcatac | 1140 |
| gaacctcttt | tggatcatgc | aatactgtac | agaaagtttt | ttcattttcc | ttccaattgt | 1200 |
| ttcttctggc | agggaacttt | cattggaccc | cagaggatgt | tgctaagtcg | attctttgca | 1260 |
| tgatgatgtc | tggtccttgt | cttactggct | atacacaggt | ctggttttac | acaacaaaaa | 1320 |
| gctgacttgt | tcttattcta | gtgcatttgc | ttggtgctac | aataacctag | acttgtcgat | 1380 |
| ttccagacaa | tcaacgactg | gtatgataga | gatatcgacg | caattaatga | gccatatcgt | 1440 |
| ccaattccat | ctggagcaat | atcagagcca | gaggtaactg | agacagaaca | ttgtgagctt | 1500 |
| ttatctcttt | tgtgattctg | atttctcctt | actccttaaa | atgcaggtta | ttacacaagt | 1560 |
| ctgggtgcta | ttattgggag | gtcttggtat | tgctggaata | ttagatgtgt | gggtaagttg | 1620 |
| gcccttctga | cattaactag | tacagttaaa | gggcacatca | gatttgctaa | aatcttccct | 1680 |

```
tatcaggcag ggcataccac tcccactgtc ttctatcttg ctttgggagg atcattgcta   1740
tcttatatat actctgctcc acctcttaag gtaagtttta ttcctaactt ccactctcta   1800
gtgataagac actccatcca agttttggag ttttgaatat cgatatctga actgatctca   1860
ttgcagctaa aacaaaatgg atgggttgga aattttgcac ttggagcaag ctatattagt   1920
ttgccatggt aagatatctc gtgtatcaat aatatatggc gttgttctca tctcattgat   1980
ttgtttcttg ctcacttgac tgataggtgg gctggccaag cattgtttgg cactcttacg   2040
ccagatgttg ttgttctaac actcttgtac agcatagctg gggtactctt ttggcaaacc   2100
ttttatgttg cttttttcgt tatctgttgt aatatgctct tgcttcatgt tgtacctttg   2160
tgataatgca gttaggaata gccattgtta acgacttcaa aagtgttgaa ggagatagag   2220
cattaggact tcagtctctc ccagtagctt ttggcaccga aactgcaaaa tggatatgcg   2280
ttggtgctat agacattact cagctttctg ttgccggtat gtactatcca ctgttttttgt   2340 gcagctgtgg cttctatttc ttttccttga tcttatcaac tggatattca ccaatggtaa   2400
agcacaaatt aatgaagctg aatcaacaaa ggcaaaacat aaaagtacat tctaatgaaa   2460
tgagctaatg aagaggaggc atctactttt atgtttcatt agtgtgattg atggattttc   2520
atttcatgct tctaaaacaa gtattttcaa cagtgtcatg aaataacaga acttatatct   2580
tcatttgtac ttttactagt ggatgagtta cacaatcatt gttatagaac caaatcaaag   2640
gtagagatca tcattagtat atgtctattt tggttgcagg atatctatta gcatctggga   2700
aaccttatta tgcgttggcg ttggttgctt tgatcattcc tcagattgtg ttccaggtaa   2760
agacgttaac agtctcacat tataattaat caaattcttg tcactcgtct gattgctaca   2820
ctcgcttcta taaactgcag tttaaatact ttctcaagga ccctgtcaaa tacgacgtca   2880
agtaccaggt aagtcaactt agtacacatg tttgtgttct tttgaaatat ctttgagagg   2940
tctcttaatc agaagttgct tgaaacactc atcttgatta caggcaagcg cgcagccatt   3000
cttggtgctc ggaatatttg taacggcatt agcatcgcaa cactgaaaaa ggcgtatttt   3060
gatggggttt tgtcgaaagc agaggtgttg acacatcaaa tgtgggcaag tgatggcatc   3120
aactagttta aaagattttg taaaatgtat gtaccgttat tactagaaac aactcctgtt   3180
gtatcaattt agcaaaacgg ctgagaaatt gtaattgatg ttaccgtatt tgcgctccat   3240
ttttgcattt cctgctcata tcgaggattg gggtttatgt tagttctgtc acttctctgc   3300
tttcagaatg tttttgtttt ctgtagtgga ttttaactat tttcatcact ttttgtattg   3360
attctaaaca tgtatccaca taaaaacagt aatatacaaa aatgatactt cctcaaactt   3420
tttataatct aaatctaaca actagctagt aacccaacta acttcataca attaatttga   3480
gaaactacaa agactagact atacatatgt tatttaacaa cttgaaactg tgttattact   3540
acctgatttt tttctattct acagccattt gatatgctgc aatcttaaca tatcaagtct   3600
cacgttgttg gacacaacat actatcacaa gtaagacacg aagtaaaacc aaccggcaac   3660
```